US011185656B2

(12) United States Patent
Oddo et al.

(10) Patent No.: US 11,185,656 B2
(45) Date of Patent: Nov. 30, 2021

(54) PULSED PRESSURE SWING ADSORPTION SYSTEM AND METHOD

(71) Applicant: Aires Medical LLC, Mooresville, NC (US)

(72) Inventors: Nicholas L. Oddo, Hilton Head Island, SC (US); Peter D. Fitchen, Ann Arbor, MI (US); Eugene H. Breniman, San Antonio, TX (US)

(73) Assignee: Aires Medical LLC, Ann Arbor, MI (US)

( * ) Notice: Subject to any disclaimer, the term of this patent is extended or adjusted under 35 U.S.C. 154(b) by 0 days.

(21) Appl. No.: 17/200,109

(22) Filed: Mar. 12, 2021

(65) Prior Publication Data
US 2021/0196918 A1 Jul. 1, 2021

Related U.S. Application Data

(63) Continuation of application No. 16/704,413, filed on Dec. 5, 2019, now Pat. No. 10,946,161.
(Continued)

(51) Int. Cl.
*B01D 53/04* (2006.01)
*A61M 16/10* (2006.01)
(Continued)

(52) U.S. Cl.
CPC ...... *A61M 16/101* (2014.02); *A61M 16/0003* (2014.02); *A61M 16/0063* (2014.02);
(Continued)

(58) Field of Classification Search
CPC .. B01D 53/04; B01D 53/047; B01D 53/0454; B01D 53/0476; B01D 2257/102;
(Continued)

(56) References Cited

U.S. PATENT DOCUMENTS

| 5,048,515 A | * | 9/1991 | Sanso | A61M 16/00 128/204.26 |
| 6,484,721 B1 | * | 11/2002 | Bliss | A61M 16/00 128/204.18 |

(Continued)

*Primary Examiner* — Frank M Lawrence, Jr.
(74) *Attorney, Agent, or Firm* — Caldwell Intellectual Property Law, LLC

(57) ABSTRACT

A pressure swing adsorption (PSA) system and methods for controlling each PSA cycle performed by the PSA system to produce oxygen enriched gas during productive portions of a user breathing cycle, and to cease production of oxygen enriched gas during non-productive portions of the user breathing cycle, is provided. The PSA system synchronizes PSA cycle phases including adsorption and desorption phases with a user's individual inhalation and exhalation phases, on a breath by breath basis, such that each PSA cycle can be dynamically varied from a succeeding PSA cycle, in real time in response to variations in the user's breathing cycle. An oxygen delivery device including a breathing cycle sensor provides breathing cycle inputs to a controller for use with at least one algorithm to detect breathing flow phases during each user breath, and to synchronize each PSA cycle to the user's breathing flow phases, on a breath-by-breath basis.

15 Claims, 36 Drawing Sheets

Related U.S. Application Data

(60) Provisional application No. 62/775,733, filed on Dec. 5, 2018.

(51) Int. Cl.
*A61M 16/00* (2006.01)
*B01D 53/047* (2006.01)
*A61M 16/20* (2006.01)

(52) U.S. Cl.
CPC ........ *A61M 16/0093* (2014.02); *A61M 16/20* (2013.01); *B01D 53/047* (2013.01); *B01D 53/0454* (2013.01); *B01D 53/0476* (2013.01); *B01D 2257/102* (2013.01); *B01D 2259/40009* (2013.01)

(58) Field of Classification Search
CPC ...... B01D 2259/40009; A61M 16/101; A61M 16/0003; A61M 16/0063; A61M 16/0093; A61M 16/20
USPC .......... 95/1, 8, 11, 19, 23, 96, 130; 96/109–111, 113, 121; 128/204.18, 128/204.21, 204.22, 204.26, 205.24, 128/205.12, 205.27
See application file for complete search history.

(56) References Cited

U.S. PATENT DOCUMENTS

| | | | | |
|---|---|---|---|---|
| 10,799,663 | B1* | 10/2020 | Oddo | A61M 16/026 |
| 10,946,161 | B2* | 3/2021 | Oddo | A61M 16/125 |
| 2008/0105258 | A1* | 5/2008 | Deane | A61M 16/101 |
| | | | | 128/204.21 |
| 2009/0229460 | A1* | 9/2009 | McClain | B01D 53/0446 |
| | | | | 95/96 |
| 2014/0137744 | A1* | 5/2014 | Wilkinson | B01D 53/047 |
| | | | | 96/152 |
| 2014/0216453 | A1* | 8/2014 | Whitcher | A61M 16/204 |
| | | | | 128/202.26 |

\* cited by examiner

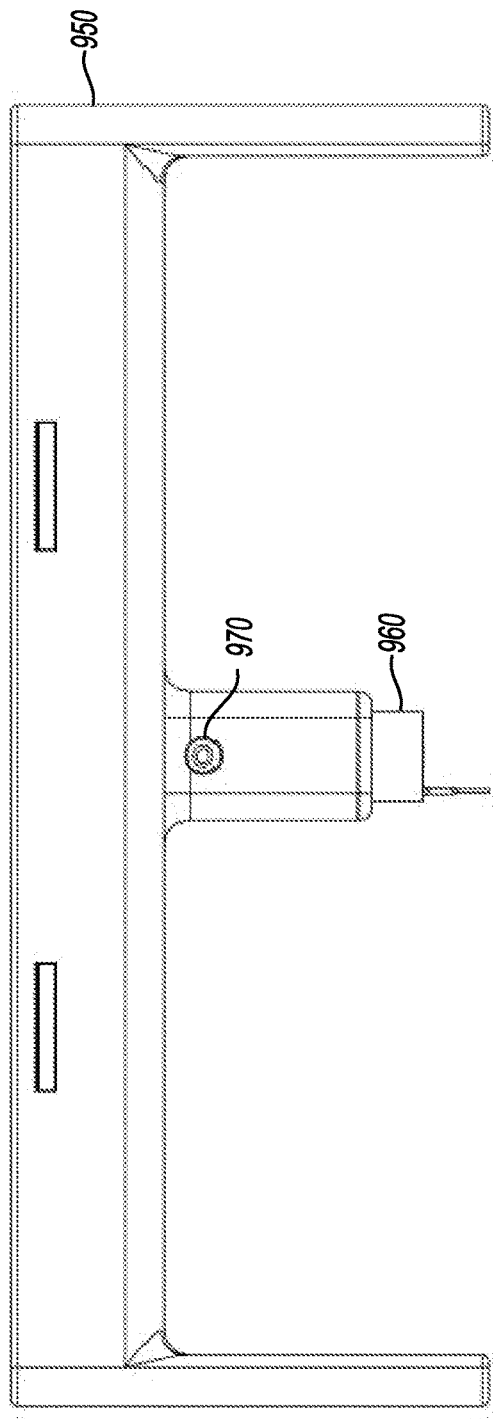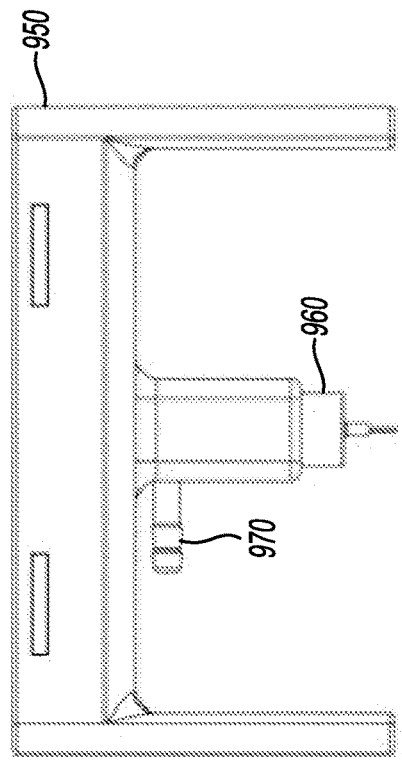
FIG. 9C
FIG. 9D

PULSED PRESSURE SWING ADSORPTION SYSTEM AND METHOD

CROSS REFERENCES TO RELATED APPLICATIONS

This Application claims priority to and the benefit of U.S. patent application Ser. No. 16/704,413 filed Dec. 5, 2019, and U.S. Provisional Patent Application 62/775,733 filed Dec. 5, 2018, which is hereby incorporated by reference in its entirety.

TECHNICAL FIELD

The present disclosure relates generally to an oxygen concentrator, and more particularly to oxygen concentrators including pulsed pressure swing adsorption systems and methods for outputting oxygen enriched gas from the oxygen concentrator.

BACKGROUND

Typical atmospheric air consists of two primary types of molecules, nitrogen and oxygen, and lower concentrations of many other substances. Human lungs extract oxygen from atmospheric air via breathing. The human respiratory cycle alternates between inhalation, wherein air and hence oxygen is uptake into the lungs, and exhalation, wherein carbon dioxide is expelled from the lungs through a gas exchange process. At rest, this cycle typically repeats 15-20 times per minute, or every 3 to 4 seconds. During more intense activity, the cycle is repeated more frequently. Humans extract oxygen from the air that flows into the lungs during inhalation. The vast majority of the oxygen intake is drawn from the volume of air from roughly the first approximately 70% of the inhalation, however during the final approximately 30% of the inhalation there is a volume of air in the nose, trachea, and bronchi that although inhaled, is exhaled from the human body without gas exchange. This last volume of air in each inhalation provides very little to no useful oxygen to the human body.

Some medical conditions, such as chronic obstructive pulmonary disease (COPD), make human lungs less efficient at extracting oxygen from atmospheric air. One treatment for these medical conditions is to increase the fraction of oxygen in the air that the individual breathes. Supplemental oxygen may also be used in other applications, such as in aircraft at high altitude and for athletes recovering from particularly strenuous activities. Supplemental oxygen may be provided by storing oxygen in a tank which delivers highly concentrated oxygen to cannulas that connect to the individual's nose. Mobility is improved somewhat by using a portable oxygen concentrator that produces oxygen from the ambient air as opposed to an oxygen storage tank. However, such oxygen concentrators still impair the individual's mobility due to their physical size and weight and limited battery life.

Pressure swing adsorption (PSA) is a cyclical adsorption process wherein inlet gas is pressurized and separated to produce a raffinate product. This adsorption process occurs when pressurized inlet gas interacts with a molecular sieve such as zeolite. Air is pressurized, and the nitrogen gas component of the inlet air is selectively adsorbed by the molecular sieve compared to the oxygen. This adsorbed gas is then desorbed by depressurizing the adsorbent bed, therein regenerating the adsorbent bed, allowing for additional product gas such as oxygen to be produced. This product gas production rate depends on several factors such as oxygen recovery and productivity, which are influenced by the cycle time of the pressure swing adsorption system as well as many other factors.

Portable oxygen concentrators utilize a selectively adsorbent media, such as zeolite. The selective nature means that certain gas components, like nitrogen, are more likely to be adsorbed than other gas components, like oxygen. Furthermore, adsorption varies based on the gas pressure. When air at elevated pressure is passed through a bed containing adsorbent material such as zeolite, the nitrogen in the air is adsorbed into the zeolite and air with a dramatically higher percentage of oxygen emerging from the zeolite bed. The zeolite's ability to adsorb nitrogen is limited. As the quantity of nitrogen in the zeolite increases, the adsorption rate generally decreases. The zeolite can be "regenerated" by lowering the pressure in the system. At lower pressure, the adsorbed nitrogen is desorbed (released) from the zeolite bed. The desorbed nitrogen can be vented from the zeolite bed, in some embodiments of the invention via a different opening. The process of separating oxygen gas from nitrogen gas by alternately pressurizing and depressurizing a zeolite bed is called Pressure Swing Adsorption (PSA). Since PSA produces concentrated oxygen only during the adsorption (high pressure) phase, current oxygen concentrators typically utilize multiple zeolite beds such that at least one adsorbent bed is producing oxygen at all times. During one phase, a first bed will be adsorbing while a second bed is desorbing. During the next phase, the first bed is desorbing, and the second bed is adsorbing. Each phase typically lasts about 2-4 seconds. These devices not only require multiple beds, but also require a multitude of valves, contributing to their size, weight, power consumption, and cost.

Skarstrom cycle pressure swing adsorption systems utilize two adsorbent beds, a surge tank, and a series of valves to switch between the adsorbent beds. Such pressure swing adsorption systems generate continuous output, wherein one adsorbent bed producing raffinate product while at the same time the other adsorbent bed is regenerating, switching from adsorption to desorption after a fixed predetermined period of time, also referred to as the cycle time.

SUMMARY

The present disclosure relates generally to systems and methods for pressure swing adsorption systems and oxygen concentrators. Other embodiments are directed to systems and computer readable media associated with control methods described herein.

An oxygen concentrator system and method for providing oxygen enriched gas to a user of the oxygen concentrator are described herein. In an illustrative example, the oxygen concentrator includes a pressure swing adsorption (PSA) system including an adsorption column, an air compressing device configured to output pressurized air, and a gas outlet configured to flow a first output gas to a user of the oxygen concentrator. The gas outlet, the air compressing device, and the adsorption column are in fluid communication via a plurality of valves. The PSA system is configured to perform a PSA cycle by selective opening and closing of the plurality of valves, where the PSA cycle includes a plurality of PSA phases including an adsorption phase and a desorption phase. In one example, the PSA system is configured to produce the oxygen enriched gas during the adsorption phase, and to cease the production of the oxygen enriched gas during the desorption phase. The oxygen concentrator further includes a controller configured to control execution of the PSA cycle by selectively actuating the plurality of valves to perform the plurality of PSA phases, and to control the flow of the first output gas through the gas outlet, where the first output gas is the oxygen enriched gas produced by the adsorption column. The oxygen concentrator includes a sensor in communication with the gas outlet and the controller, which is configured to sense a breathing parameter of a breathing cycle of the user. The user's breathing cycle includes a plurality of breaths, with each respective breath of the plurality of breaths including an inhalation phase and an exhalation phase. In one example, the controller is further configured to receive, from the sensor, a breathing input defined by the breathing parameter, and to determine, for each respective breath, using the breathing input and one or more algorithms, the beginning of the inhalation phase of the respective breath and the beginning of the exhalation phase of the respective breath. The controller is further configured to synchronize execution of the PSA cycle with each respective breath such that the adsorption phase is actuated at the beginning of the inhalation phase of the respective breath, the desorption phase is actuated at the beginning of the exhalation phase of the respective breath, and the flow of the enriched oxygen gas via the gas outlet is actuated at the beginning of the inhalation phase of the respective breath.

The inhalation phase of the user's breath includes a useful period and a dead space period, where the dead space period occurs between the useful period and the exhalation phase of the respective breath. In one example, the controller is further configured to determine for each respective breath, using the breathing input, the beginning of the dead space period of the inhalation phase, and to synchronize execution of the PSA cycle with each respective breath such that the adsorption cycle is ceased at the beginning of the dead space period of the respective breath and the flow of oxygen enriched gas via the gas outlet is ceased at the beginning of the dead space period of the respective breath.

In a non-limiting example, the gas outlet of the oxygen concentrator system is configured to flow a second output gas to a user of the oxygen concentrator, where the second output gas is the pressurized air outputted from the air compression device and/or a blower included in the oxygen concentrator system. The controller is further configured to synchronize execution of each respective PSA cycle with each respective breath such that the flow of pressurized air via the gas outlet is actuated at the beginning of the dead space period of the inhalation phase.

In one example, the oxygen concentrator system and/or the controller is configured to control the flow of the pressurized air via the outlet such that the pressured air provides a positive end expiratory pressure (PEEP) to the user. In one example, the controller is configured to actuate the oxygen concentrator to function as one of a continuous positive airway pressure (CPAP) device and a bilevel airway pressure (BiPAP) device.

In an illustrative example, each respective breath of a user's breathing cycle is immediately preceded in the breathing cycle by a preceding breath and is immediately succeeded in the breathing cycle by a succeeding breath. Each breath can be described as having an exhalation phase includes a non-useful period and a pre-inhalation period, where the pre-inhalation period occurs between the non-useful period of the respective breath and the inhalation phase of the succeeding breath. In one example, the oxygen concentrator system and/or the controller is further configured to determine for each respective breath, using the breathing input, the beginning of the pre-inhalation period of the exhalation phase, and to synchronize execution of the respective PSA cycle with each respective breath such that the adsorption phase of the PSA cycle for the succeeding breath is actuated at the beginning of the pre-inhalation period of the exhalation phase, the flow of the pressurized air via the gas outlet is ceased at the beginning of the pre-inhalation period of the exhalation phase, and the flow of the enriched oxygen gas via the gas outlet is actuated at the beginning of the pre-inhalation period of the exhalation phase.

In one example, the oxygen concentrator system further includes an oxygen delivery device connected to the gas outlet and in communication with the controller. The oxygen delivery device can include a cannula operatively connected to the gas outlet via the oxygen delivery device, where the user received the output gas from the PSA system via the gas outlet and the cannula, and a breathing cycle sensor in communication with at least one of the cannula and the gas outlet. The cannula can be, for example, a nasal cannula configured to be worn by the user. The breathing cycle sensor is configured to sense at least one of a breathing pressure, breathing flowrate, EtCO2, CO2 concentration, and O2 concentration of the user, which is outputted to the controller, where the controller is further configured to receive, from the breathing cycle sensor, a sensor input, and using the sensor input, determine at least one of the breathing cycle and an oxygen requirement of the user.

In one example, the PSA system is configured as a pulsed pressure swing adsorption (PPSA) system. In one example, the air compressing device includes at least one microblower. In one example, the oxygen concentrator system further includes a vacuum device in fluid communication with the adsorption column, where the vacuum device is selectively actuable by the controller during the desorption phase to assist in performance of the desorption phase, for example, by flowing gaseous nitrogen desorbed from the adsorption bed out of the adsorption column and/or PSA system.

The above features and advantages, and other features and advantages, of the present disclosure are readily apparent from the following detailed description of some of the best modes and other particular embodiments for carrying out the invention, as defined in the appended claims, when taken in connection with the accompanying drawings.

BRIEF DESCRIPTION OF THE DRAWINGS

FIGS. 9A-D show schematic diagrams of an exemplary Pressure Swing Adsorption system according to the Pressure Swing Adsorption system of FIGS. 7A-B;

DETAILED DESCRIPTION

Figure 1A:
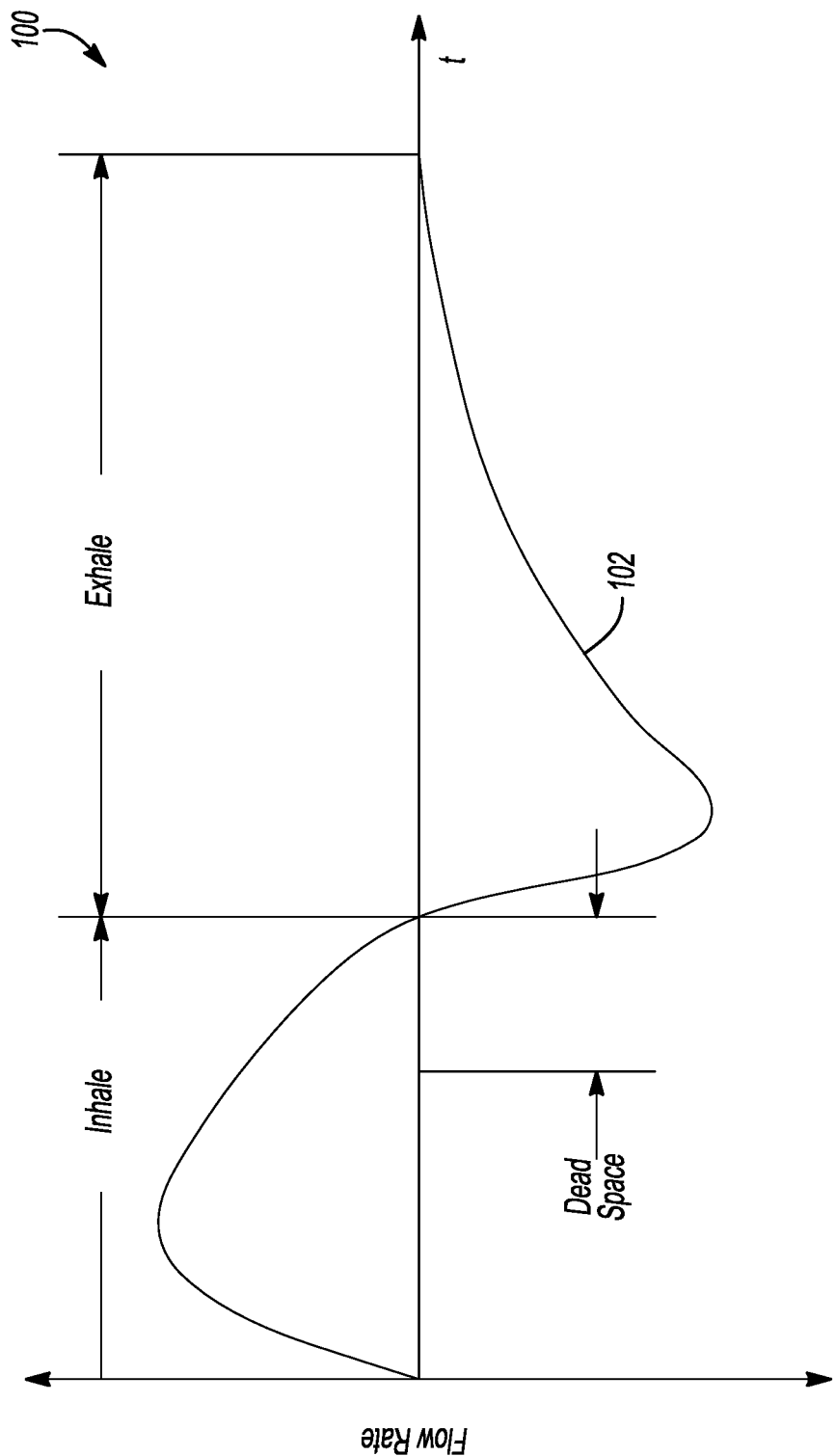
FIG. 1A shows a phase graph illustrating the flow phases of a human breathing cycle including inhalation and exhalation phases.

Referring to the drawings, wherein like reference numbers correspond to like or similar components throughout the several figures, methods and systems are disclosed herein, relating to pressure swing adsorption systems and oxygen concentrators.

I. Exemplary Breathing Cycle and Prior Art Oxygen Concentrators

FIG. 1A shows a phase graph 100 which illustrates an example human breathing cycle 102 comprising an inhalation phase and an exhalation phase. Typically, the majority of oxygen intake delivered to a human body is drawn from the volume of air inhaled from roughly the first 67% of the inhalation phase. A portion of the air drawn by the human during the inhalation phase will not reach the human body. This portion of the air, the last volume, is known as anatomical dead space or dead space air, illustrated in FIG. 1A, and provides very little to no useful oxygen to the human body.

Figure 1B:
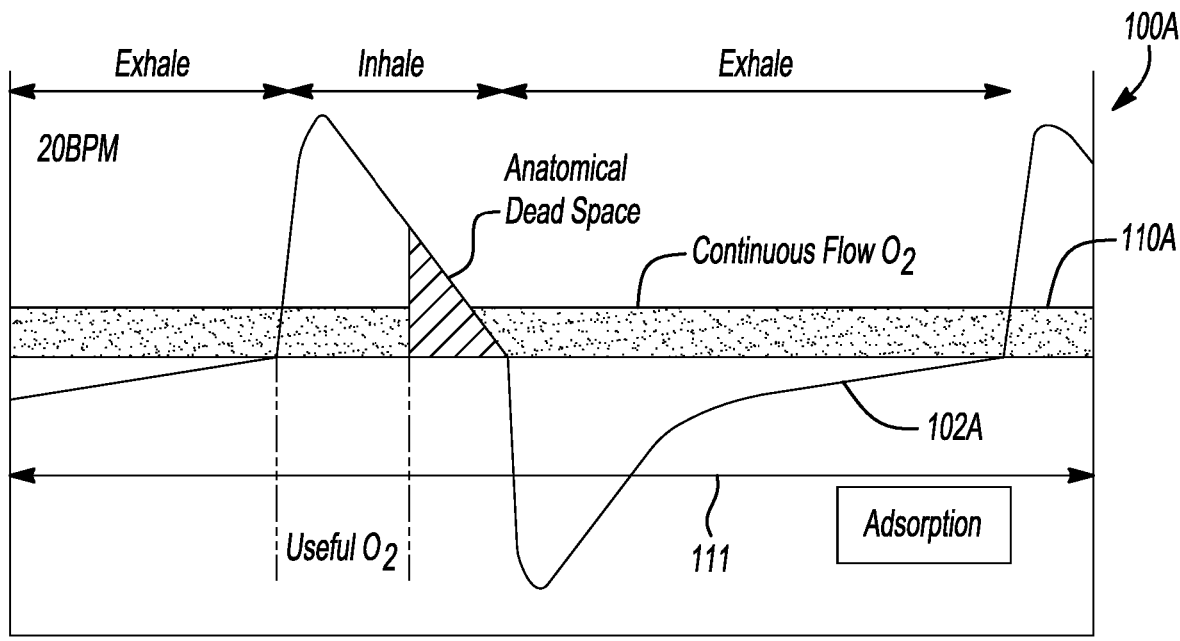
FIG. 1B (prior art) shows a phase graph illustrating flow phases of breathing cycles in conjunction with PSA phases of a PSA cycle of a prior art oxygen concentrator.

Previous oxygen concentrators are comprised of a two-bed pressure swing adsorption (PSA) system that continuously produces an oxygen enriched gas output product 110A. The oxygen enriched gas outputted from a PSA system can be referred to herein as oxygen output, as oxygen gas, as oxygen concentrated gas, as oxygen product gas, as oxygen, as enriched oxygen, as oxygen enriched gas, and/or as oxygen enriched product. As illustrated by the phase graph 100A shown in FIG. 1B (prior art), oxygen output 110A is continuously produced during the entire breathing cycle, e.g., during both the inhalation and exhalation phases, of a user of an oxygen concentrator including the PSA system illustrated by phase graph 100A, whether or not the user actually demands the oxygen. In this configuration, the continuous output of oxygen 110A will be provided even if the user is in the exhalation phase of the user's breathing cycle 102A, which is wasteful and unnecessary since oxygen is for the most part only required by the user during the inhalation phase of the breathing cycle 102A. Further, the adsorption phase 111 of the pressure swing adsorption cycle of the prior art oxygen concentrator illustrated by the phase graph 110A of FIG. 1B is continuous throughout and irrespective of changes in the user breathing cycle 102A. This is because with two-bed pressure swing adsorption, one adsorbent bed is always adsorbing while the other is regenerating. These individual adsorbent beds switch from adsorption to regenerating after predetermined fixed periods of time, also referred to as PSA cycle times. Continuous flow product gas output (oxygen output) 110A is always produced when the PSA system is operational since there is always one adsorbent bed that is always in the adsorption phase 111 of the PSA cycle. Thus, neither the oxygen output 110A nor the adsorption phase 111 of the prior art continuous flow oxygen concentrator illustrated by FIG. 1B is synchronized with the inhalation phase of the user breathing cycle 102A.

Figure 1C:
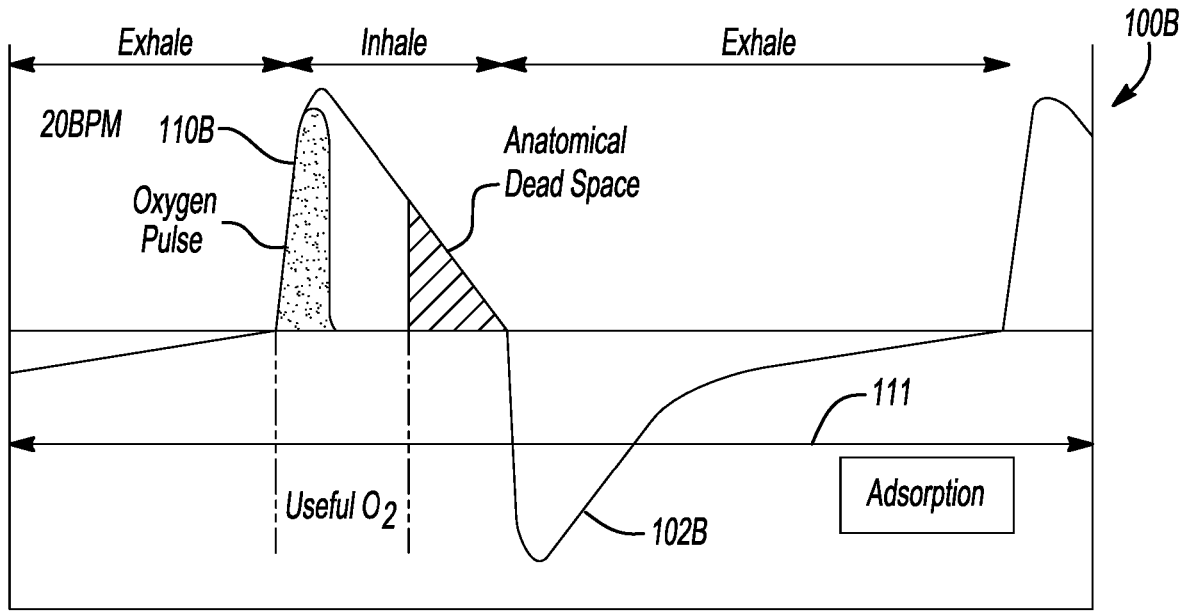
FIG. 1C (prior art) shows a phase graph illustrating flow phases of breathing cycles in conjunction with PSA phases of a PSA cycle of a prior art oxygen concentrator.

As illustrated in the phase graph 100B shown in FIG. 1C (prior art), some oxygen concentrators are configured to release an oxygen pulse dosage 110B, to conserve the oxygen product output generated by a PSA system of the oxygen concentrator, only releasing the oxygen gas to the user during the inhalation phase in short 200 to 400 millisecond bursts (pulses) using an oxygen conserving device. This prior art oxygen conserving system includes a pressurized oxygen tank at the outlet of the pressure swing adsorption system that primarily delivers oxygen only at the initial stage of inhalation, by detecting a drop in pressure as sensed by inhalation of a user. This configuration reduces the size of oxygen concentrators, since more than 67% of continuous flow oxygen is delivered when the user is not inhaling. However, the prior art pulse dose oxygen output 110B and methods of detection and/or delivery do not match a user's oxygen demand as determined by the user's breathing cycle 102B, resulting in lower fractions of inspired oxygen (FiO2) as compared to continuous flow output 110A with equivalent oxygen volumes inspired. Thus, neither the oxygen output 110B nor the adsorption phase 111 of the prior art pulse dose oxygen concentrator illustrated by FIG. 1C is synchronized with the inhalation phase of the user breathing cycle 102B. Further, pulse dose oxygen output 110B and current oxygen concentrators have several key issues including bulky and energy inefficient oxygen production systems, lag times of over 100 milliseconds for oxygen delivery, and fixed volume oxygen output that does not match user demand or adjust breath by breath. The present invention seeks to solve these problems in the prior art through on-demand oxygen production using a pulsed pressure swing adsorption system as described herein which is configured to and/or controlled by methods described herein such that oxygen enriched gas can be delivered to the user at variable times and at variable and/or in selectable doses automatically determined by the user's breathing cycle, as illustrated in FIGS. 1D through 15, described in further detail herein.

There are other drawbacks to pulse dose oxygen output systems such as the systems illustrated by the phase graphs 110A and 110B of FIGS. 1B and 1C. For example, if the user inhales at a rate faster than the rate at which pressure swing adsorption system continuously produces oxygen, these prior art oxygen concentrators will not output oxygen at all or will simply output compressor air (non-oxygen enriched) as a fail-safe. This can be harmful to the user in situations where an oxygen user needs large amounts of oxygen in a short amount of time or breathes at a high number of breaths per minute. Some oxygen users must use continuous flow oxygen 110A rather than pulse dose 110B during sleep due to the longer shallowing inhalation and exhalation phases of breathing during sleep. In this situation, pulse dose 110B is inadequate compared to continuous flow 110A. Further, for many oxygen users, a setting of "1 LPM" pulse dosage 110B provides less actual oxygenation to the user than 1 LPM of continuous flow oxygen 110A due to the discrepancy between oxygen pulse dosage delivery and actual user oxygen demand. This means that many oxygen users demand more oxygen than can be provided by pulse dosage. In prior art pulse dose oxygen concentrators, the oxygen output is synchronized with the inhalation phase of the breathing cycle, however continuous flow oxygen is not output, but rather a short burst or pulse of oxygen 110B.

Further, in previous pulse dose oxygen concentrators, two bed pressure swing adsorptions are used to continuously produce the oxygen and then pulsed out by an oxygen conservator during a user inhalation. In these previous pulse dose oxygen concentrators, the adsorption phase 111 is continuous as shown in FIG. 1C, with cycle times of the PSA system being fixed and irrespective of the user breathing pattern, e.g., the user breathing cycle 102. Thus, the system is producing oxygen continuously, even though the output of oxygen is only outputted to the user in doses 110B. While the oxygen output is synchronized with the inhalation phase of the user breathing cycle 102B, the PSA adsorption phase 111 is not synchronized with the inhalation phase of the user breathing cycle 102B.

II. Exemplary Oxygen Output Synchronized with Breathing Cycle

The following invention describes an example of a pressure swing adsorption (PSA) system 10 with one or more adsorbent beds that continuously produces oxygen during the inhalation phase of a user's breathing cycle 202, e.g., when the user inhales and which does not produce oxygen during the exhalation phase of a user's breathing cycle 202, e.g., when the user exhales. As used herein, a user's breathing cycle 202 includes a plurality of breaths, each breath includes an inhalation phase and an exhalation phase. In a breathing cycle 202 including a plurality of breaths, it would be appreciated that each breath can vary from another breath in duration, flow rate, flow volume, flow pressure, etc. Likewise, each inhalation phase can vary in duration, pressure, volume, etc. from each other inhalation phase, and each exhalation phase can vary in duration, pressure, volume, etc. from each other exhalation phase. With the disclosed invention, continuous flow oxygen production performance of the pressure swing adsorption system 10 can be optimized such that the PSA system 10 described herein can be made smaller and be more energy efficient as compared with prior art PSA systems, while enabling controlled changes, e.g., variation, in an amount and timing of oxygen flow output to the user, where the amount and timing of oxygen flow output to the user is determined by, e.g., defined by and synchronized to the specific user's breathing cycle 202 using control methods described herein. As such, the oxygen flow output 216 can be varied from breath to breath and within an inhalation phase, where the variable oxygen output can be synchronized to each breath of the user's breathing cycle 202. Accordingly, the oxygen concentrator system and associated control methods disclosed herein are advantaged by being configured to adapt and modify the oxygen output on a breath by breath basis, to output the oxygen enriched gas to the user during the useful period of the breathing cycle, and to conserve and/or not produce oxygen enriched gas during the non-useful period of the breathing cycle. Synchronizing oxygen output to the useful period of the breathing cycle, and ceasing oxygen production during the non-useful period of the breathing cycle, eliminates and/or minimizes the amount of waste oxygen which must be generated to ensure minimum oxygen gas requirements are met for the user of the oxygen concentrator. Waste oxygen, as that term is used herein, refers to oxygen which is outputted by a PSA system 10 however is not received by the user, e.g., not exchanged by the user during respiration. By minimizing and/or eliminating waste oxygen production, the amount of oxygen which must be produced by the PSA system 10 at any time, e.g., the PSA system capacity, is reduced, allowing for a PSA system of decreased size, weight and content, thus reducing the cost of the system and increasing the convenience and portability of the PSA system to the user.

Figure 1D:
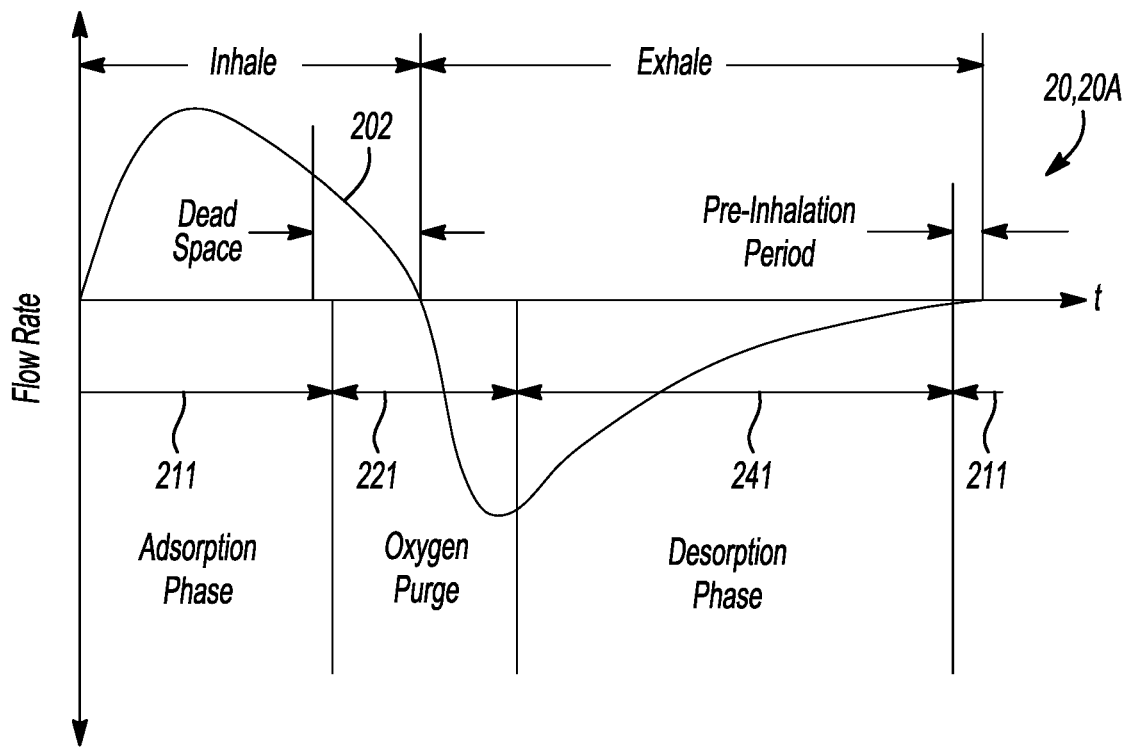
FIG. 1D-E show example phase graphs illustrating flow phases of a breathing cycle in conjunction with PSA phases of a PSA cycle of an oxygen concentrator system of the present invention.
Figure 1E:
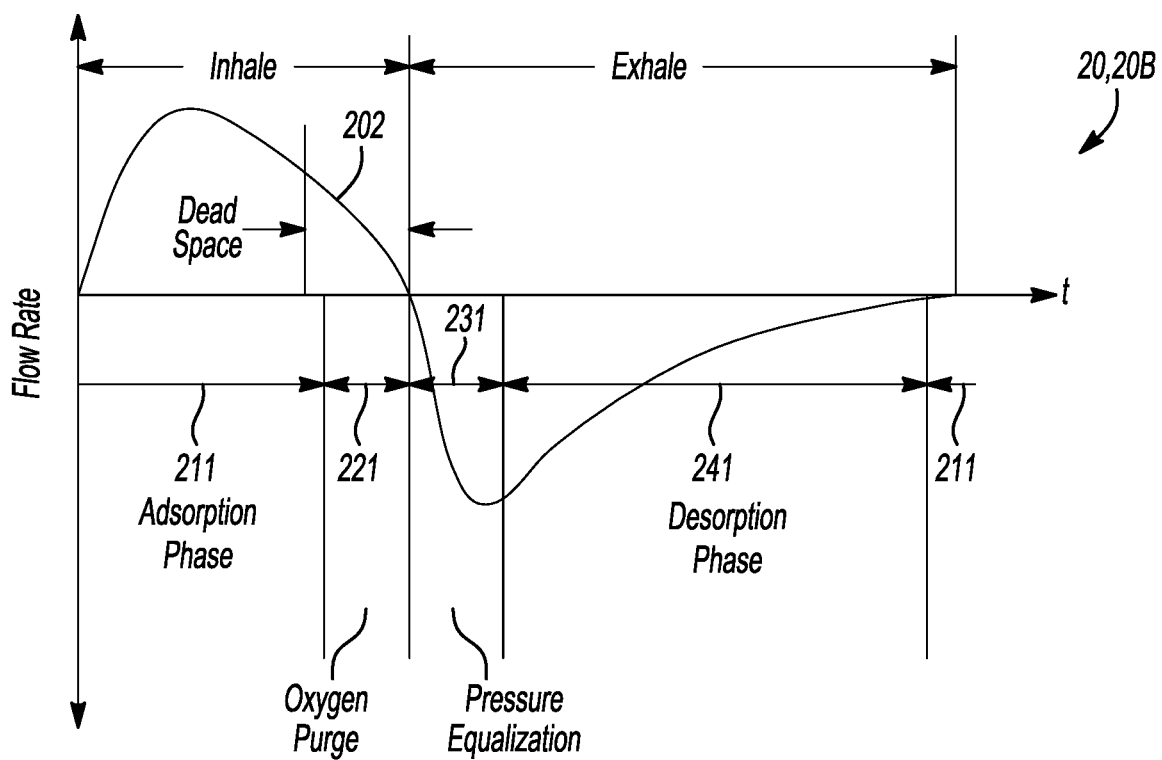

FIGS. 1D-E illustrate example flow phase graphs 20 of breathing flow phases during user breathing cycles 202 in conjunction with PSA phases 211, 221, 231, 241 of PSA cycles of a PSA system 10 included in an oxygen concentrator as described herein, where the oxygen concentrator is configured to provide enriched oxygen product to a user, and where the flowrate of the enriched oxygen provided to a user is synchronized with the breathing cycle 202 of that specific user. Various embodiments of a PSA system 10 (see FIG. 1M), such as PSA systems 300, 301, 302, 303, 304, 305, 306, 307, 500, 600, 700, 850, 860, 870, 880, 900 described herein and illustrated in the figures, are configured to provide enriched oxygen product to a user at a flowrate which is synchronized to and/or defined by that user's breathing cycle 202, and are provided herein as non-limiting examples. The example PSA systems 300, 301, 302, 303, 304, 305, 306, 307, 500, 600, 700, 850, 860, 870, 880, 900 may be collectively referred to herein as a PSA system 10, and/or may be referred to as a PSA system 10, for example, when describing features of a PSA system 10 which can be incorporated into one or more of the example PSA systems 300, 301, 302, 303, 304, 305, 306, 307, 500, 600, 700, 850, 860, 870, 880, 900. As illustrated by the phase graph 20A shown in FIG. 1D, only a portion of the enriched oxygen provided during the initial period of the inhalation phase will reach (be received by) the user. This initial period of the inhalation phase is referred to as the useful period of the inhalation phase, such that each inhalation phase of a user's breathing cycle is characterized by a useful period followed by a dead space period. When the dead space period begins toward the end of the inhalation phase, very little oxygen is received by the user. In some examples herein, the useful period of the inhalation phase can be referred to as the productive portion of the inhalation phase, and the dead space period can be referred to herein the non-production portion of the inhalation phase. In one embodiment, as illustrated by the adsorption phase 211 of the PSA cycle shown in FIG. 1D, the oxygen concentrator can provide enriched oxygen to the user beginning from the end of the user's exhalation phase, also referred to herein as a pre-inhalation period of the exhalation phase, and/or beginning at the start of the user's inhalation phase, and can continue to provide enriched oxygen up to the beginning of the dead space period of the inhalation phase, instead of providing enriched oxygen for the full inhalation phase, thus avoiding the waste of provide enriched oxygen during the non-productive dead space period and non-useful portion of the exhalation phase. In this example shown in FIG. 1D, the period during which the oxygen concentrator is providing enriched oxygen to the user is the adsorption phase 211, which is actuated by a controller 380 of the PSA system 10 to begin at the pre-inhalation period of the exhalation phase and to continue through the useful period of the inhalation phase which succeeds the exhalation phase in the user's breathing cycle 202. In some embodiments, when the dead space period of the user's inhalation phase is detected or triggered, the oxygen concentrator can switch to an oxygen purge phase 221 in which the oxygen concentrator is continuing to collect and produce enriched oxygen but is not providing the user with the enriched oxygen being collected during the dead space period. At a later point when the user is exhaling, the oxygen concentrator can switch to a desorption phase 241 where the release of adsorbed gases collected from the atmospheric air by the adsorption bed of the PSA system 10 can be synchronized with the user's exhalation phase.

The phase graph 20B shown in FIG. 1E illustrates another example of the PSA phases 211, 221, 231, 241 of the oxygen concentrator in sync with the user's breathing cycle 202. The PSA phases of the oxygen concentrator PSA cycle, including an adsorption phase 211, an oxygen purge phase 221, a pressure equalization phase 231, and a desorption phase 241 will be discussed in greater detail in the discussion below of later figures.

Figure 1F:
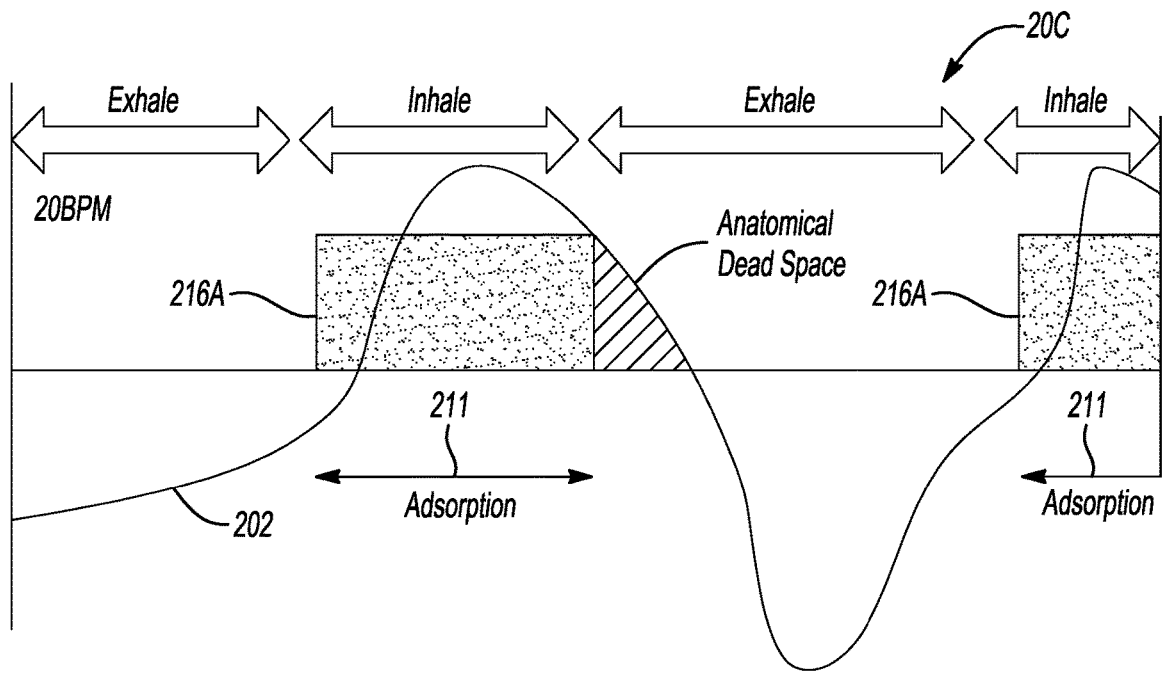
FIG. 1F shows a phase graph illustrating flow phases of breathing cycles in conjunction with PSA phases of a PSA cycle of an oxygen concentrator system of the present invention.
Figure 3A:
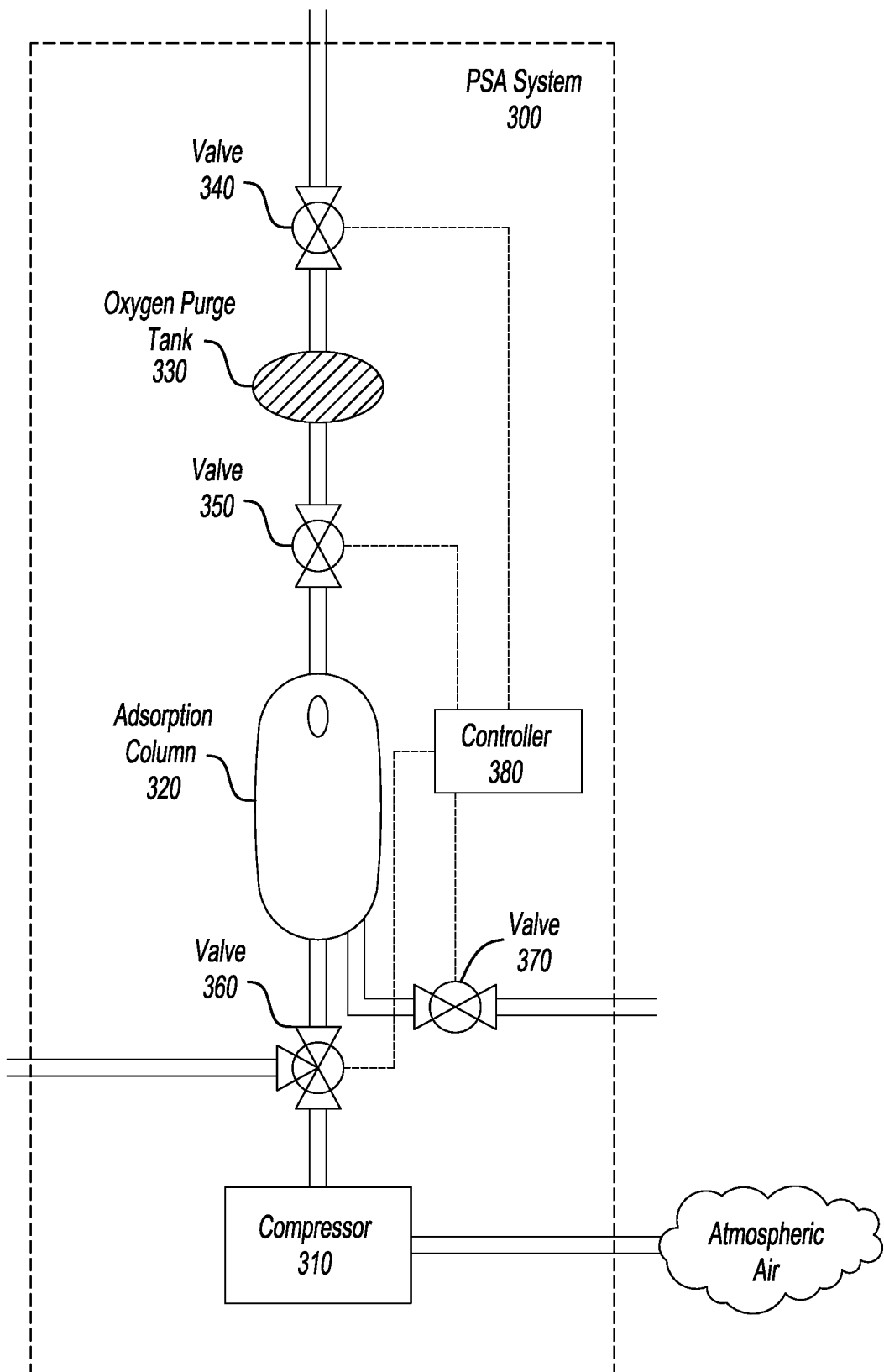
FIG. 3A shows a schematic diagram of a first example Pressure Swing Adsorption system, including a controller, according to some embodiments.
Figure 3B:
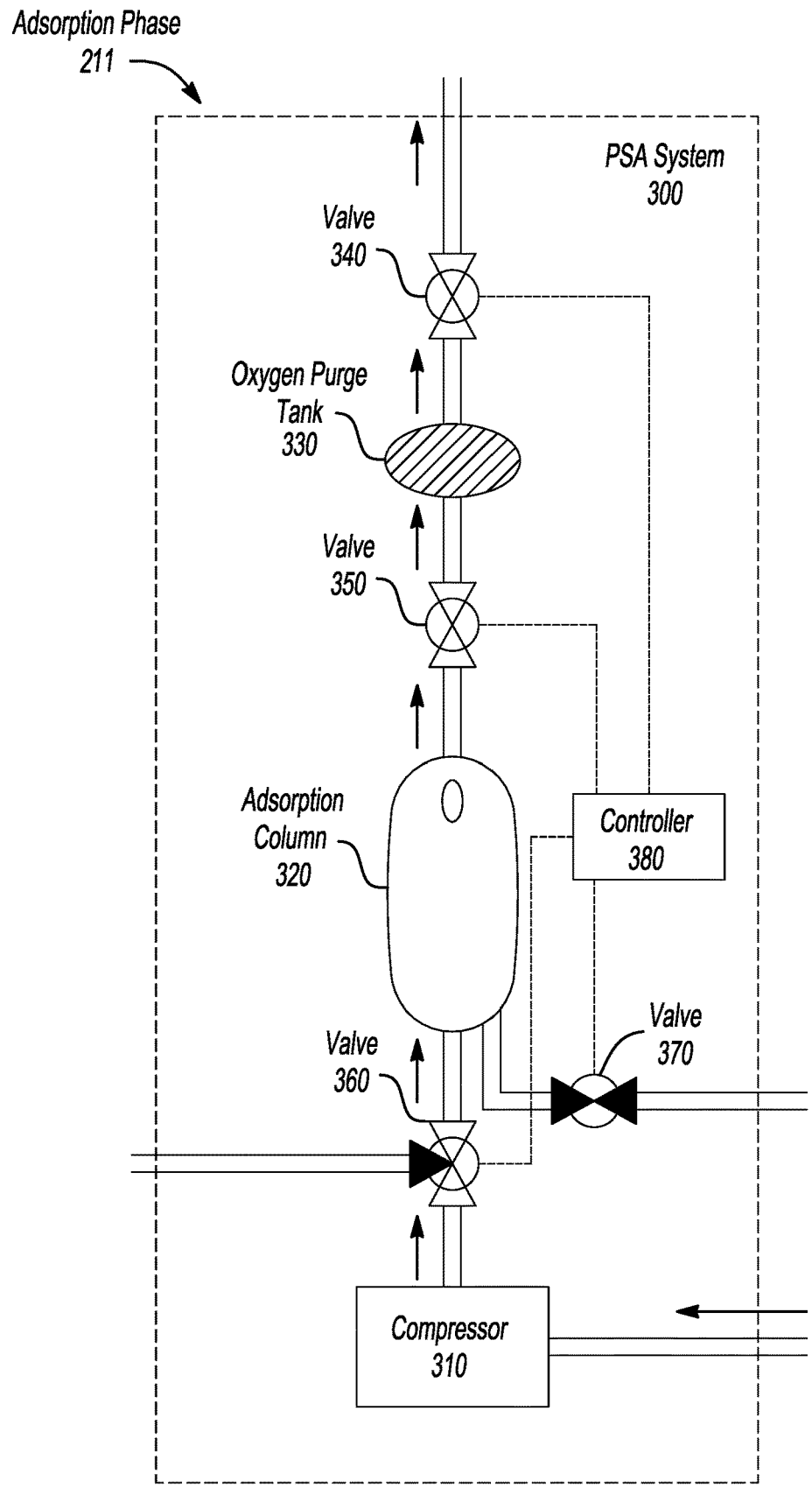
FIGS. 3B-3E show schematic diagrams illustrating exemplary valve states and flow directions of air in a breathing cycle as according to the schematic diagram of the first example Pressure Swing Adsorption system illustrated in FIG. 3A.
Figure 3C:
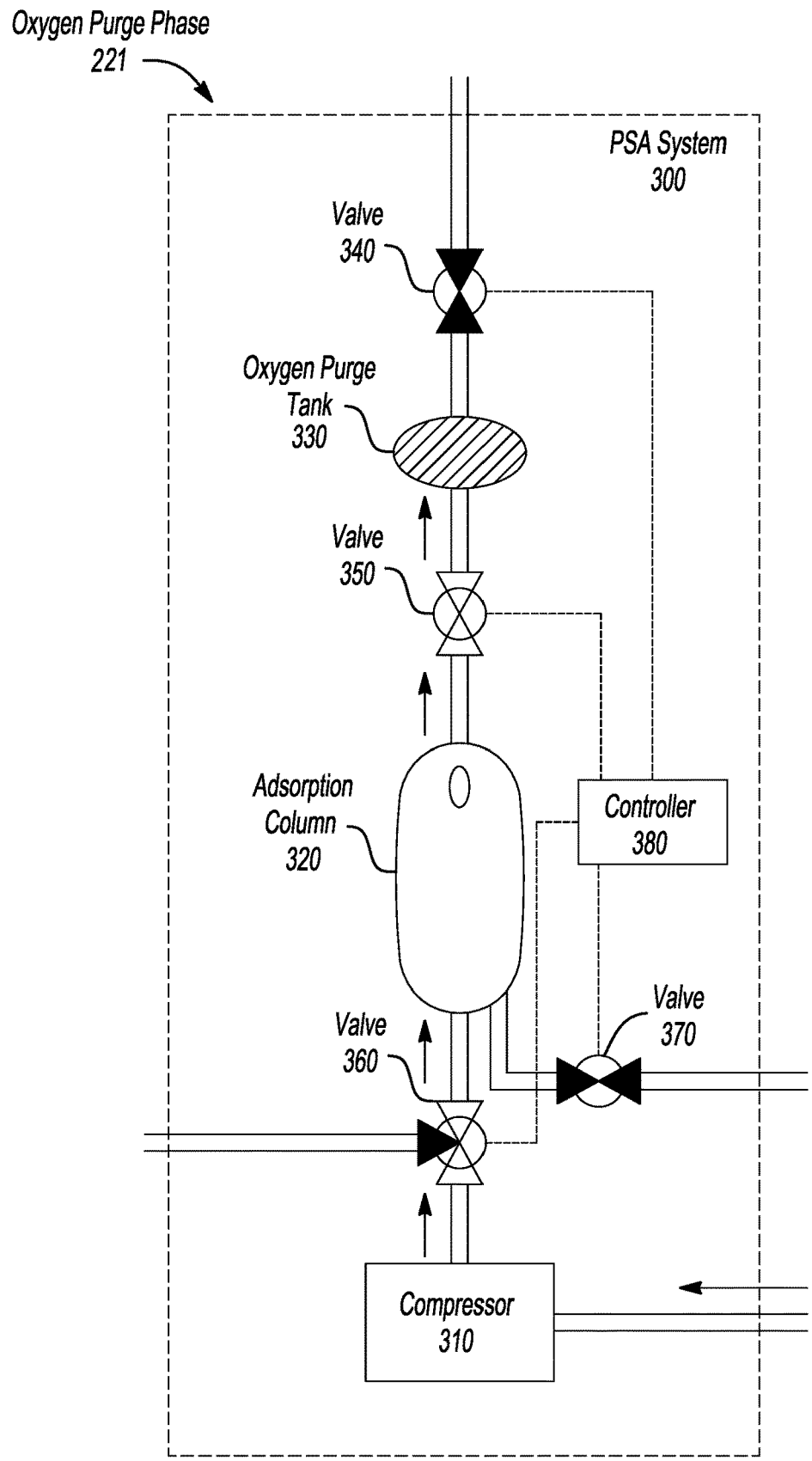
Figure 3D:
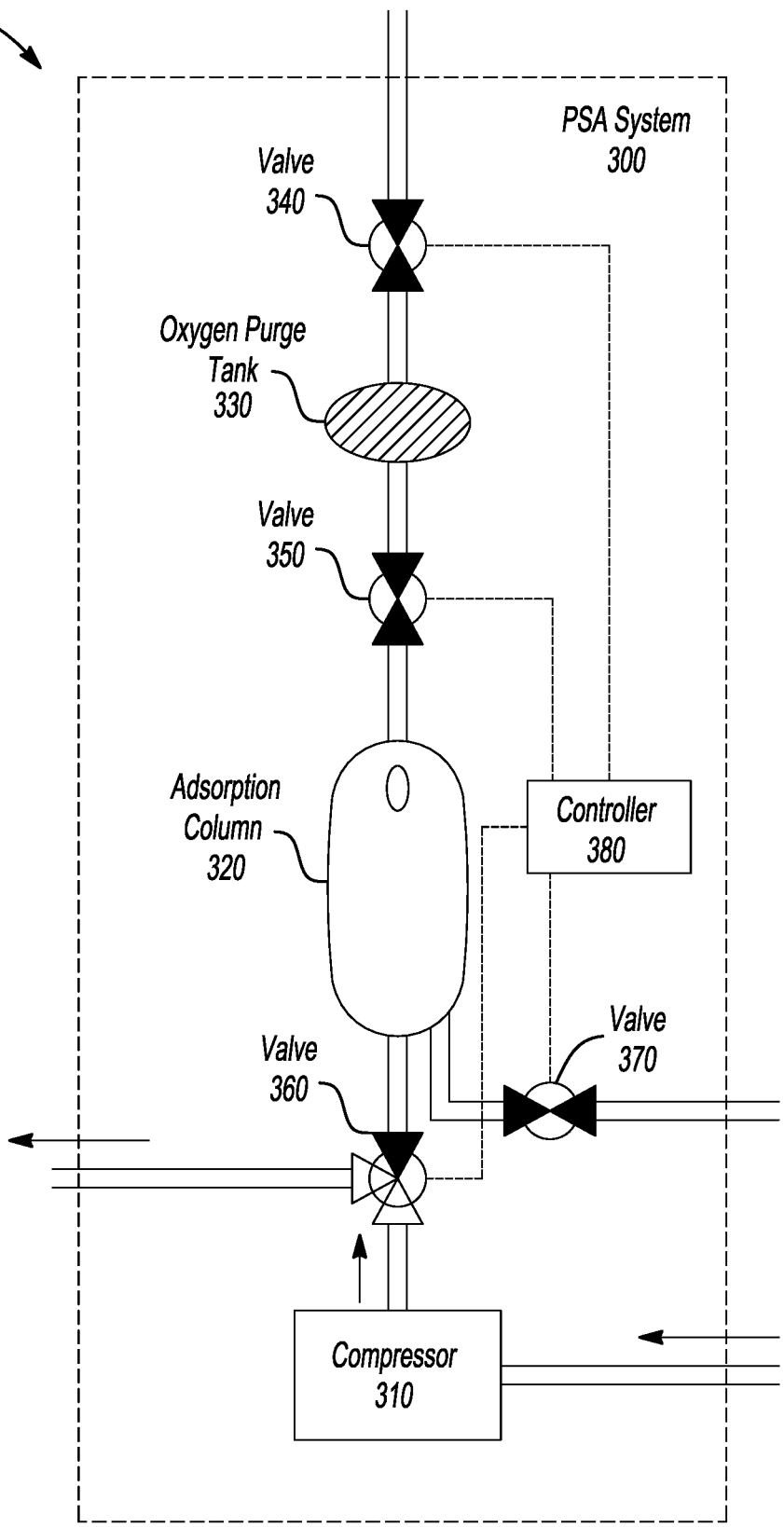
Figure 3E:
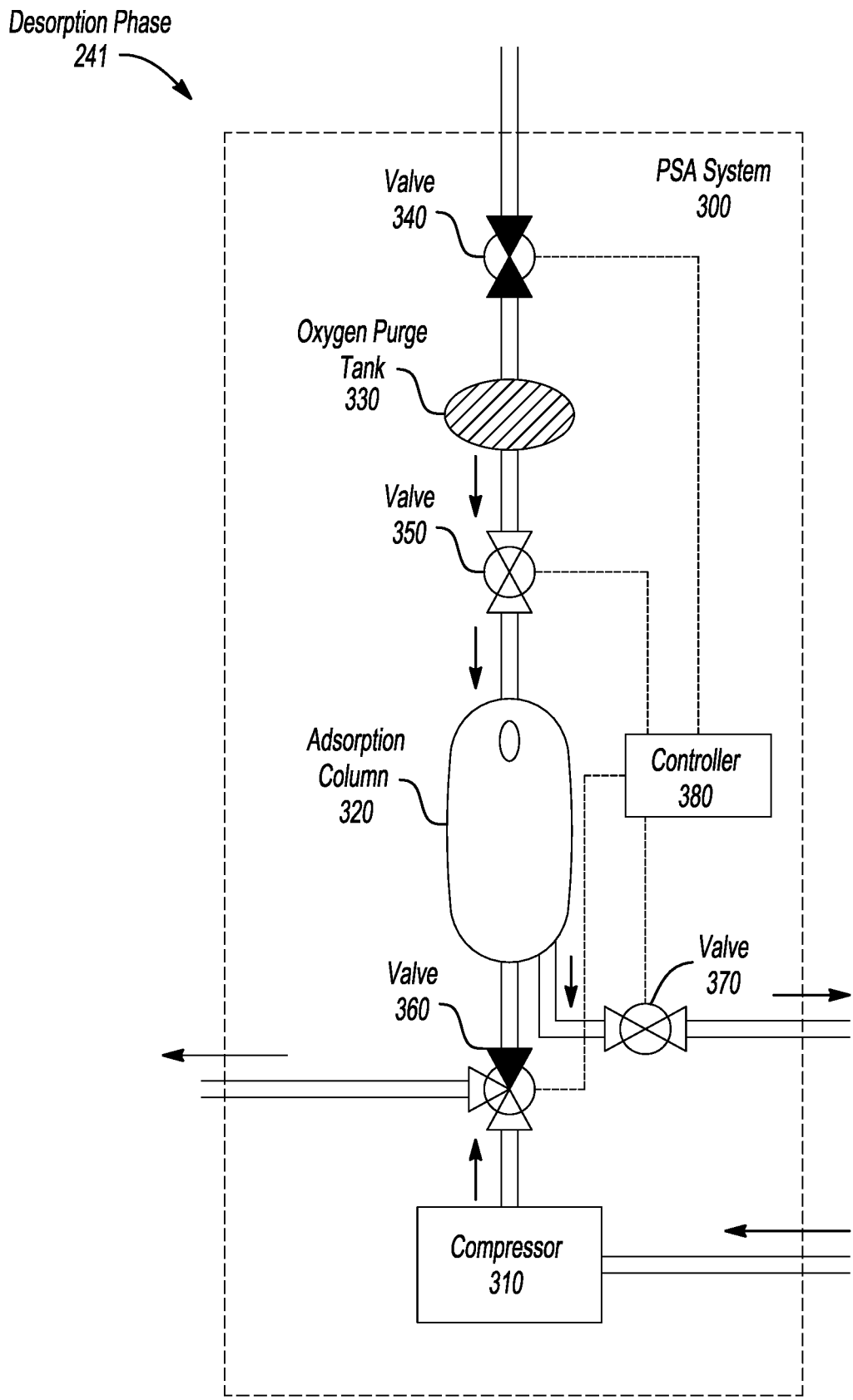
Figure 3F:
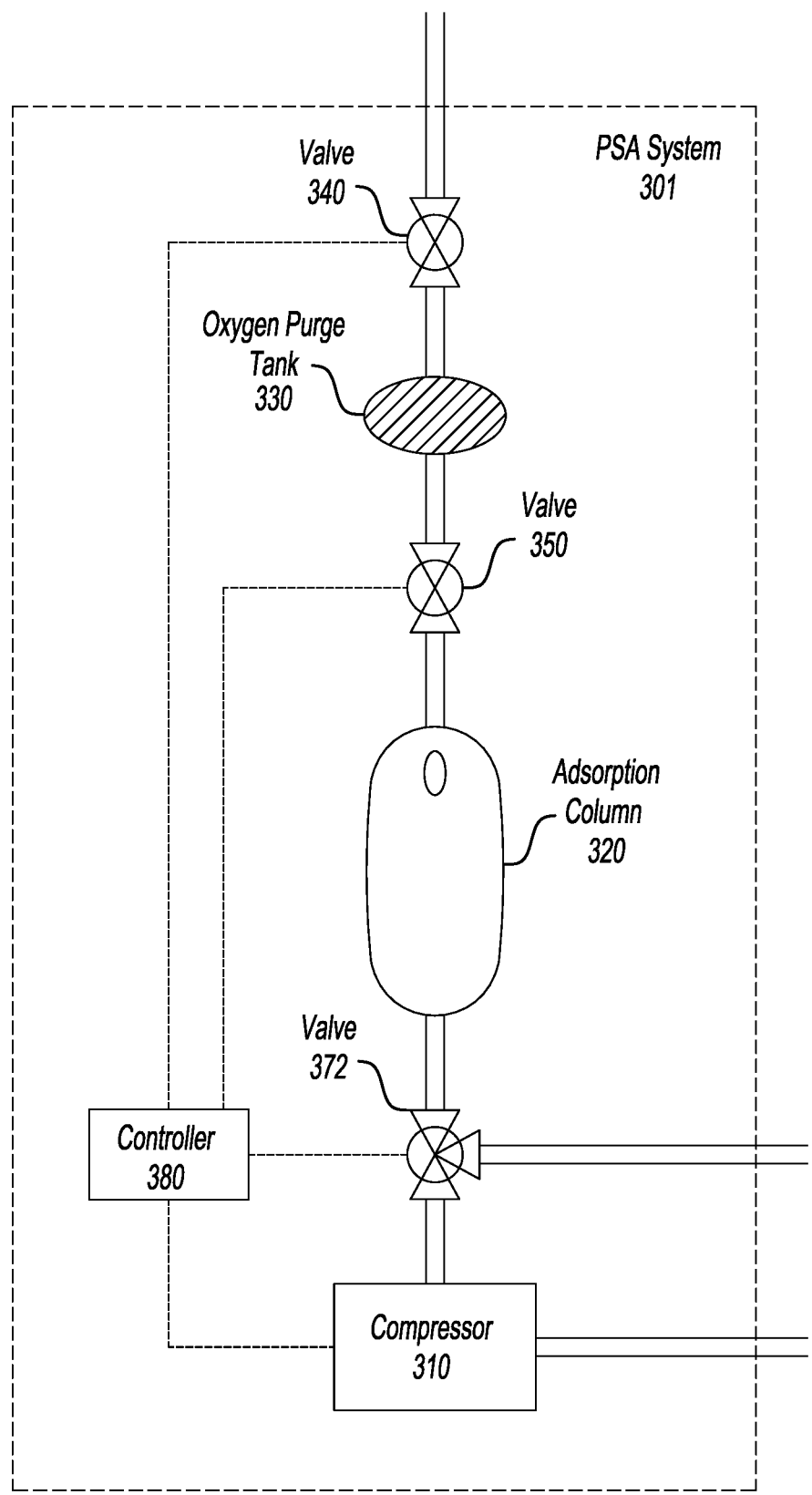
FIGS. 3F-3L shows schematic diagrams of additional examples of the first example Pressure Swing Adsorption system illustrated in FIG. 3A.
Figure 3G:
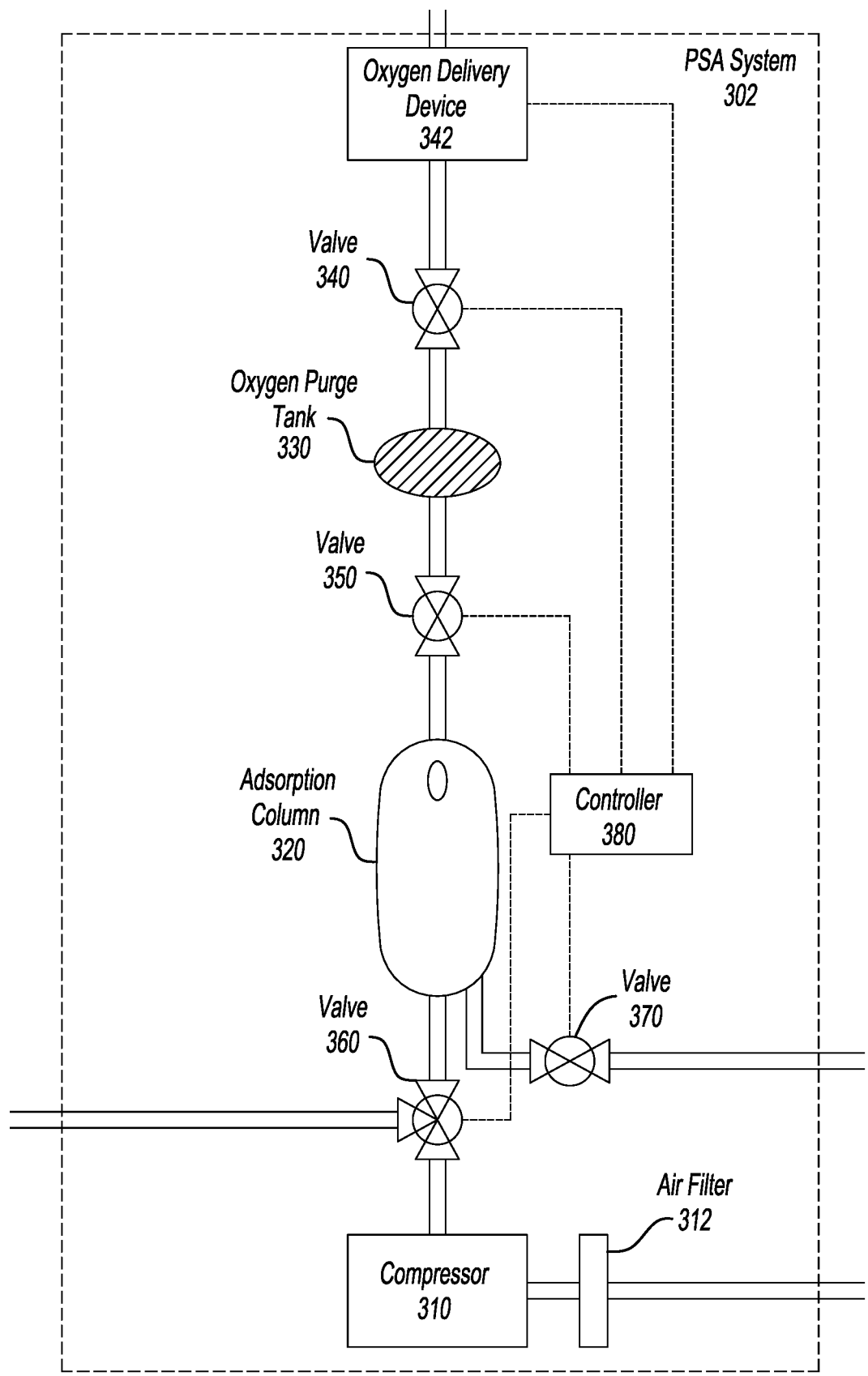
Figure 3H:
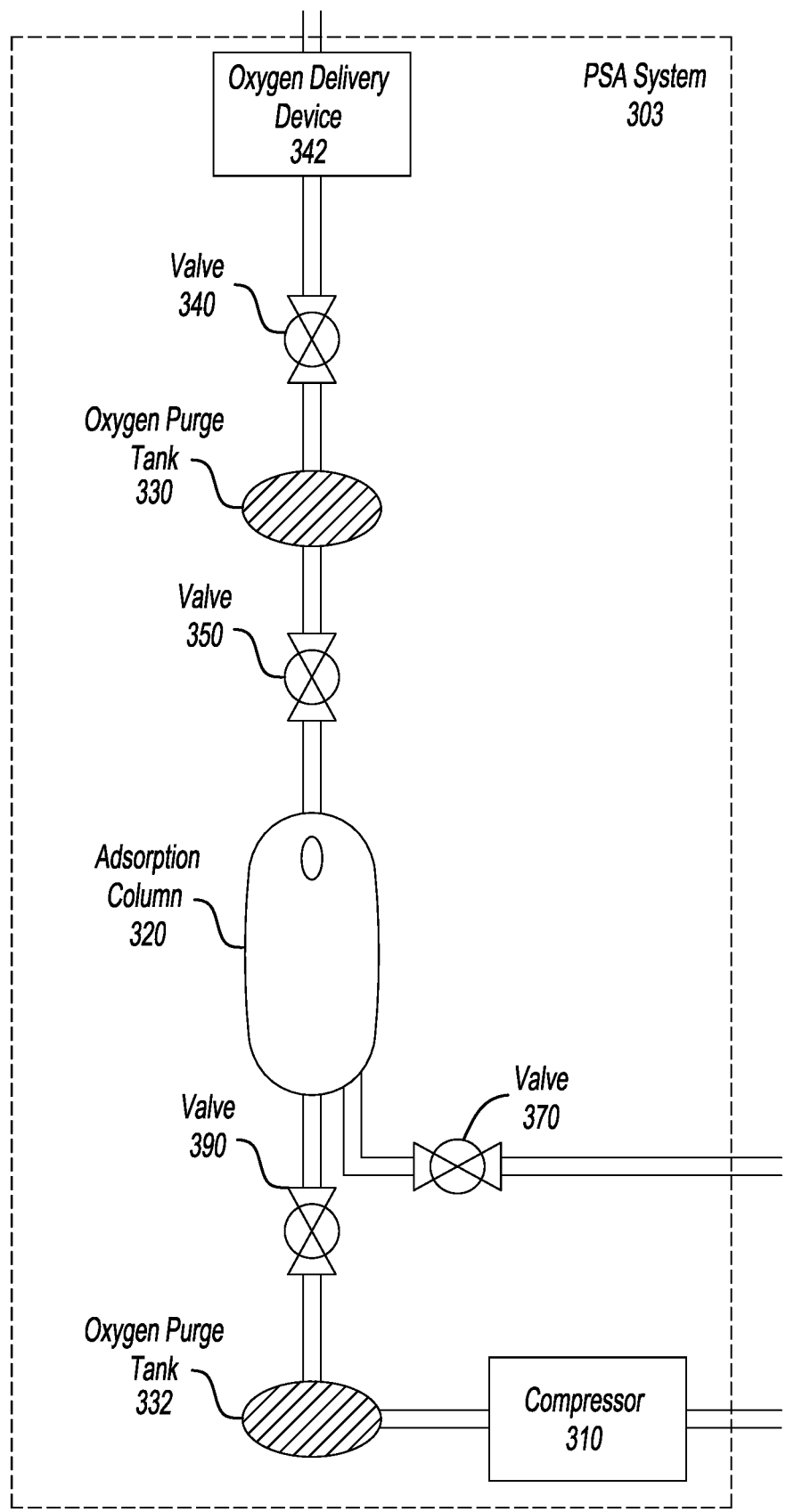
Figure 3I:
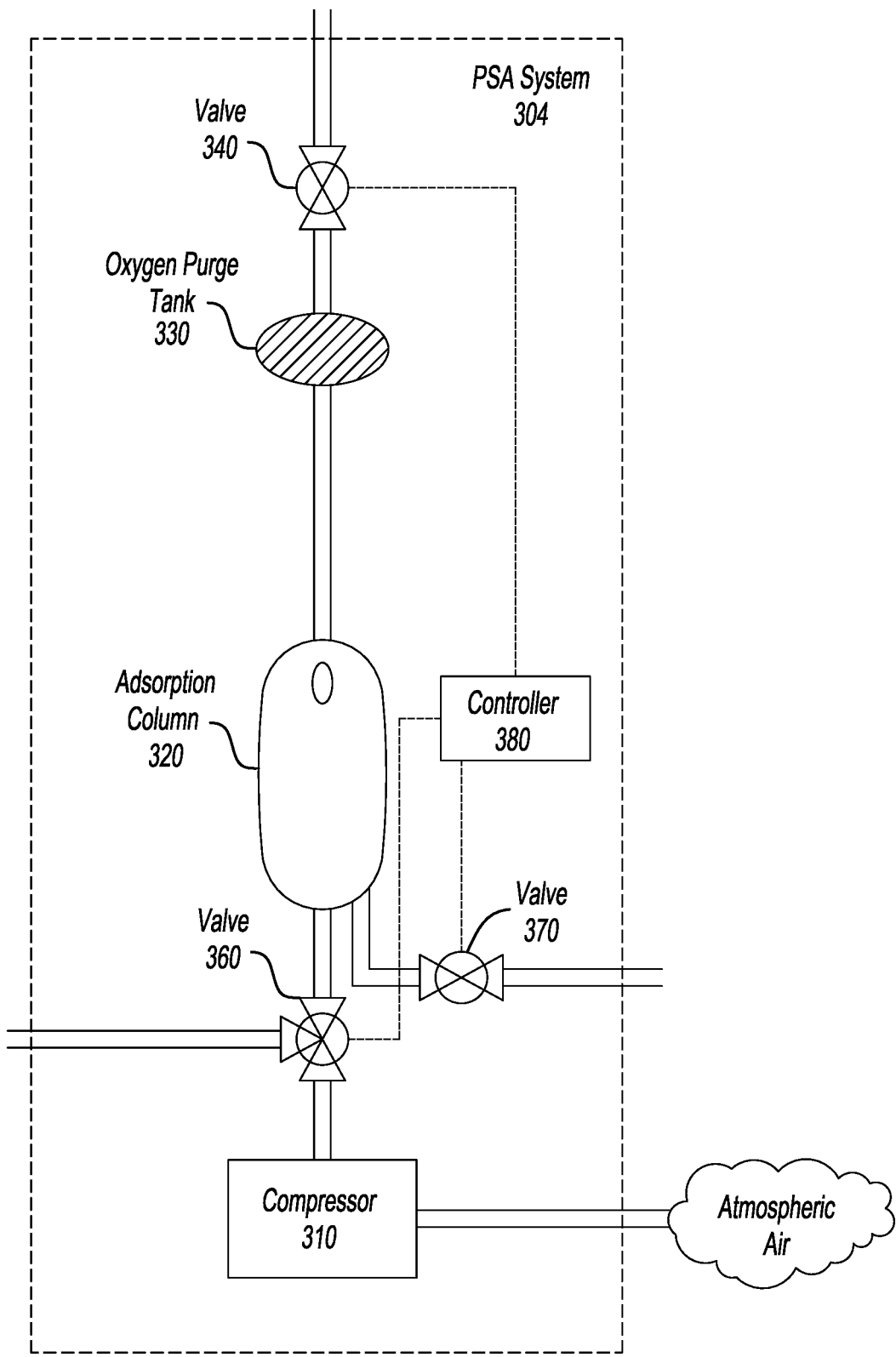
Figure 3J:
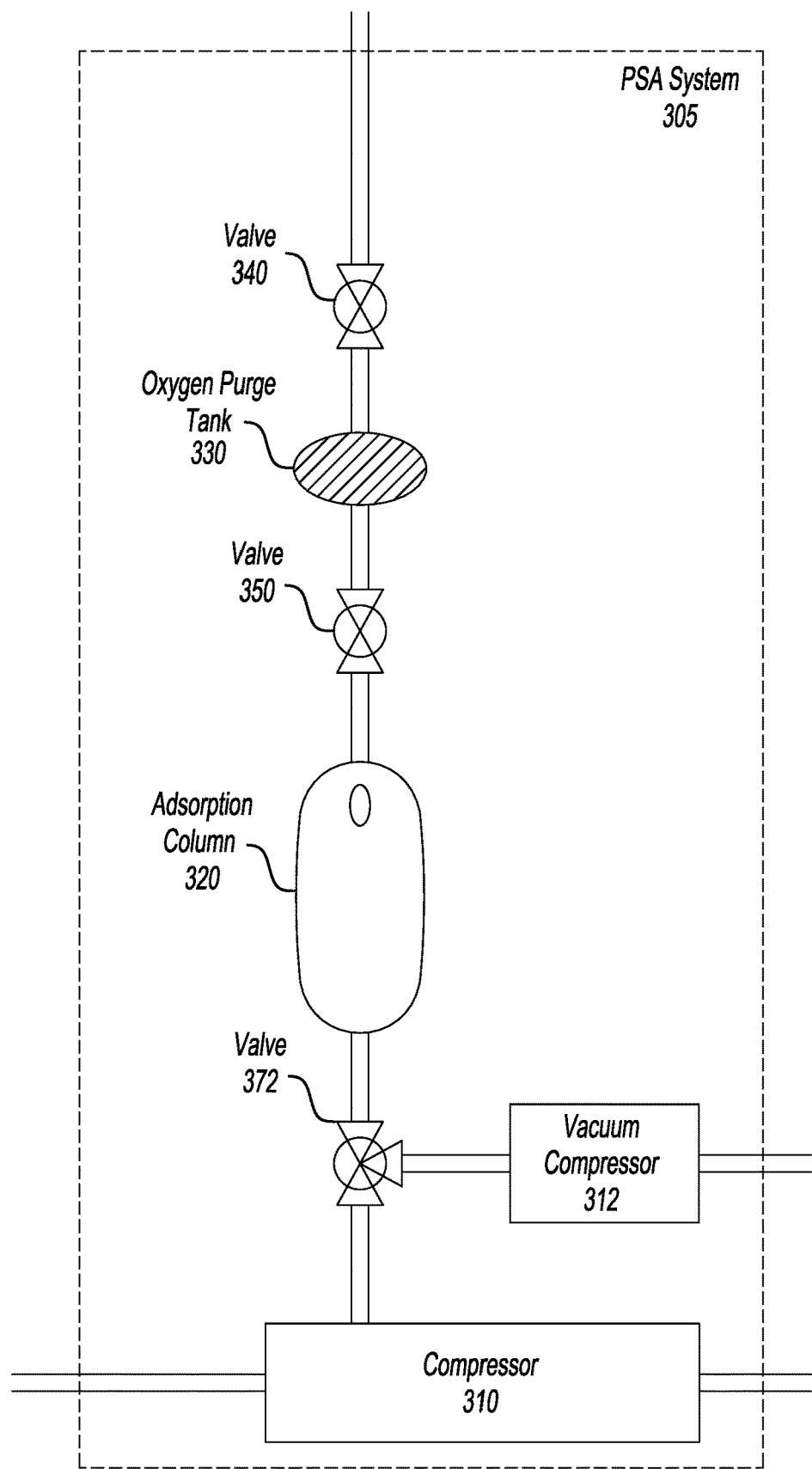
Figure 3K:
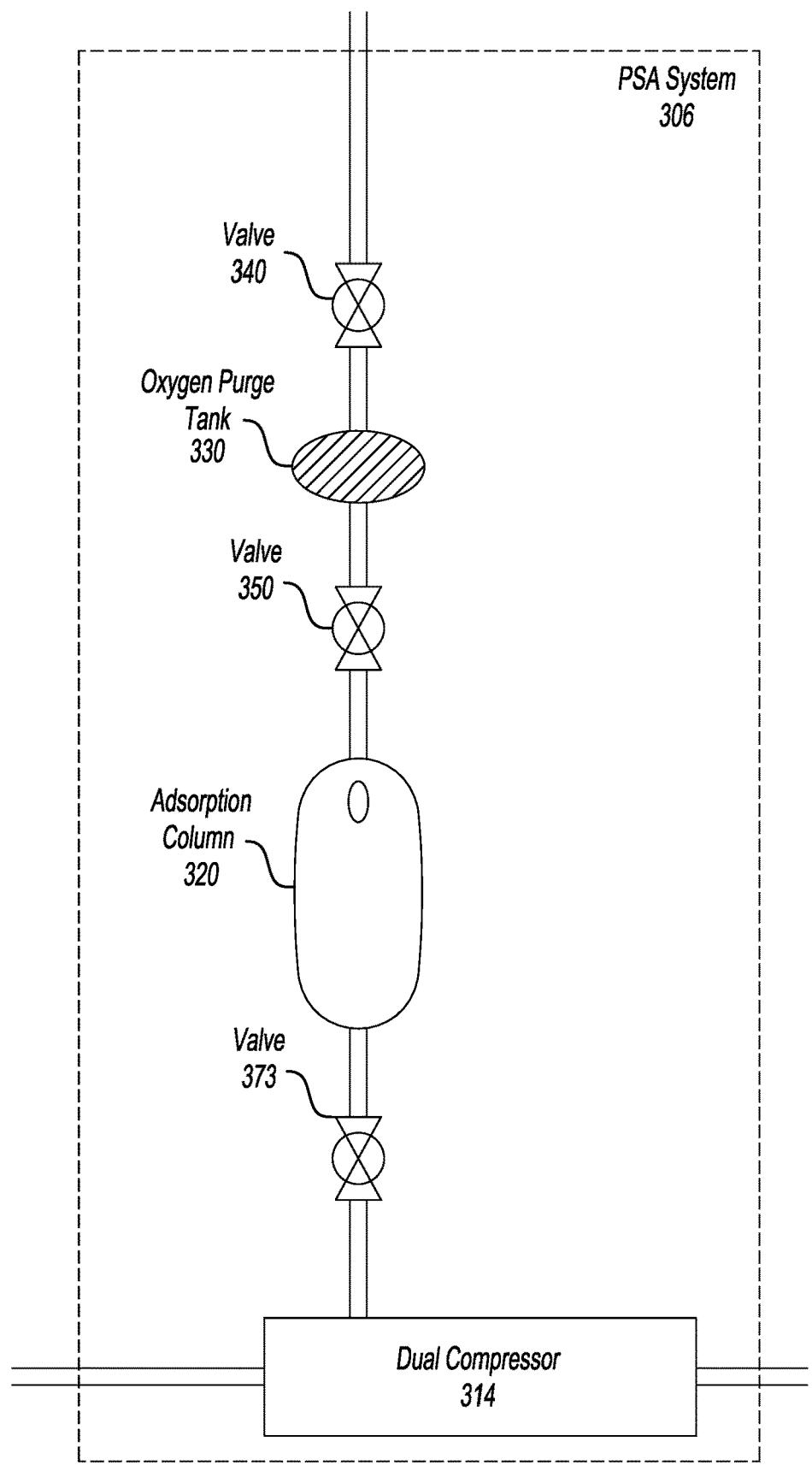
Figures 3L, 4:
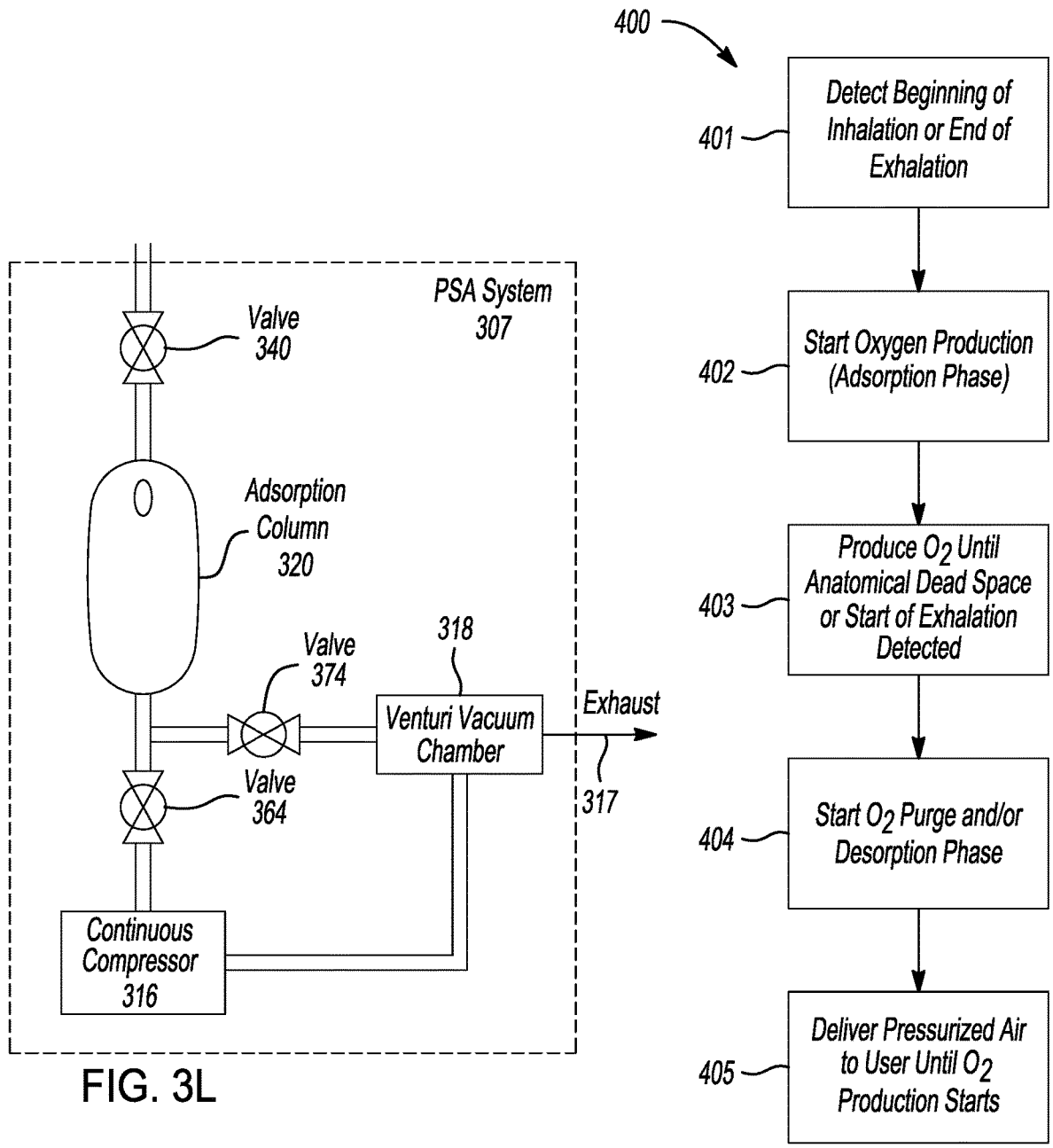
FIG. 4 shows a flowchart describing the PSA phases of a PSA cycle of a Pressure Swing Adsorption system corresponding to the inhalation and exhalation cycles of a breathing cycle.

In the example phase graph 20C illustrated in FIG. 1F, oxygen enriched gas 216A can be delivered to the user automatically at variable times and at variable and/or in selectable doses of the user's breathing cycle 202, as defined by user's breathing cycle 202, using a PSA system 10 and/or a control method, such as the control method 400 shown in FIG. 4, and as described in further detail herein. In some embodiments, the PSA cycle times and/or the duration of the adsorption phase of the pressure swing adsorption system are variable based on the user's specific breathing pattern, which can include variability between subsequent inhalation and exhalation breathing phases of the user's breathing cycle 202. Hence, with the PSA system and/or oxygen concentrator 10 disclosed herein, the oxygen product gas is produced to the user selectively, e.g., on demand only during the useful oxygen period of the user's breathing cycle 202, such as the first 70% of the inhalation phase and near the end of the exhalation phase, such as the final 10% of the exhalation phase, also referred to herein as the pre-inhalation period of the exhalation phase. Further, the adsorption phase 211 is synchronized with the useful oxygen period of the user's breathing cycle 202, rather than the adsorption phase 211 occurring continuously throughout and irrespective of changes in the user breathing cycle 202 as seen in prior art (see FIGS. 1B, 1C).

Figure 1G:
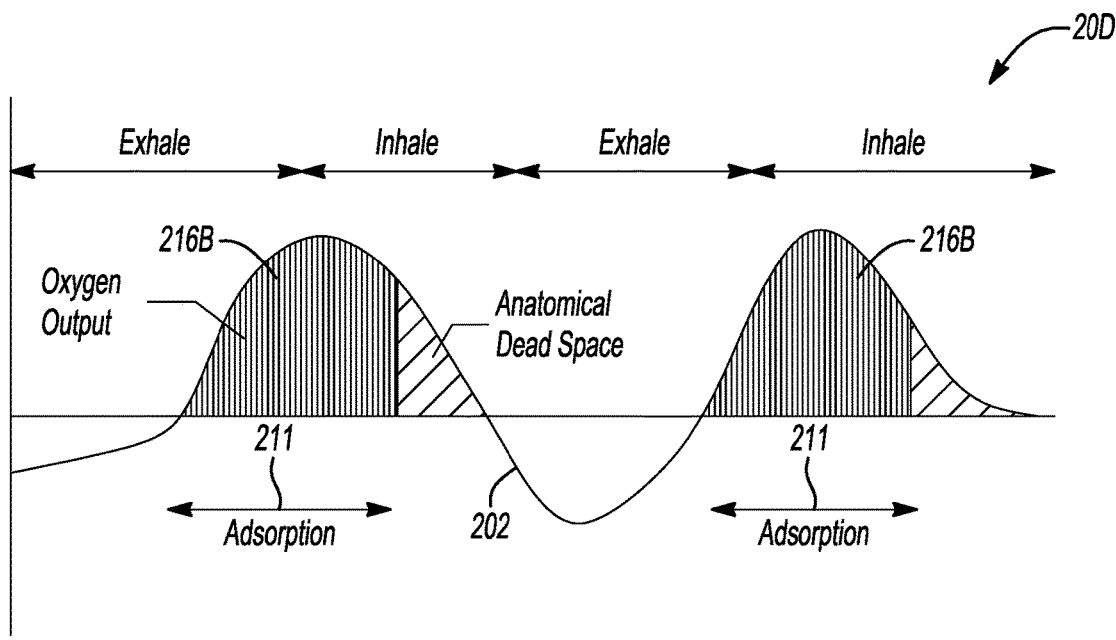
FIG. 1G shows a phase graph illustrating the flow phases of a breathing cycle in conjunction with PSA phases of a PSA cycle of an oxygen concentrator system of the present invention.

As illustrated in the phase graph 20D shown in FIG. 1G, oxygen concentrated gas 216B can be delivered to the user automatically at variable times and at variable doses. In this example, the amount of oxygen output 216B matches the demand of oxygen from the user. The oxygen demand is graphically represented by the shaded area under the user breathing rate curve shown in the phase graph 20D representing volumetric oxygen output 216B, representing the calculated tidal volumes of the inhalation and exhalations of the user. In this example, the volumetric oxygen flowrate output is dynamically adjusted using motor and flowrate control in the PSA system 10, synchronized with the changing oxygen demand of the user. The oxygen output 216B and the adsorption phase 211 of the pressure swing adsorption system 10 are in sync with the inhalation and exhalation phases of the user's breathing cycle 202. This could allow for oxygen concentrators that maintain fixed fraction of inspired oxygen (FiO2) ratios for users regardless of their changing breathing conditions, improving the clinical efficacy of long term oxygen therapy for patients with chronic lung diseases such as COPD.

Figure 1H:
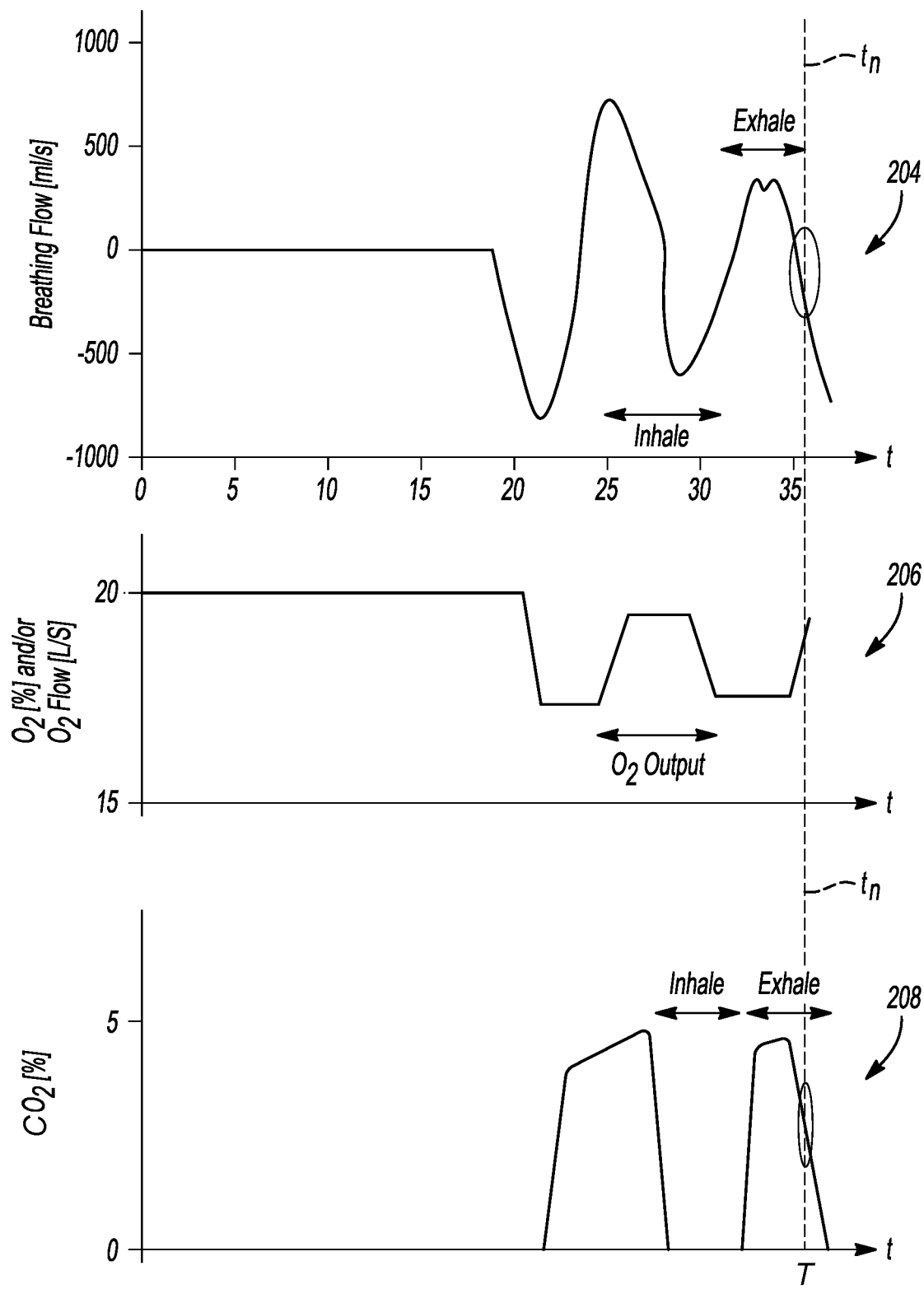
FIG. 1H shows example graphs illustrating breathing flow phases, CO2 concentration, and oxygen concentration over time, as related to a synchronization algorithm used for control of the PSA phases of a PSA cycle in some embodiments.

In the example illustrated in FIG. 1H, in some embodiments of the oxygen concentrator described herein, one or more sensors are included in the oxygen concentrator for measuring various parameters of the user's breathing cycle 202 and/or characteristics of the user's air flow during the breathing cycle 202. As shown in an example flowrate graph 204 illustrated in FIG. 1H, a user's breathing flowrate values are measured using one or more sensors, to compile digital voltage values that represent the flowrate of that user's breathing cycle over time t. These breathing flowrate values are used to determine the different phases of that user's breathing cycle, such as the inhalation phase (inhale) and exhalation phase (exhale), as well as determine the time when a user's breathing is about to switch from an inhalation phase to an exhalation phase, for example. As illustrated in the flowrate graph 204, during inhalation the flowrate values are generally negative, while during exhalation the flowrate values are generally positive. In addition to measuring the user's breathing flow 204, and as shown in graph 206, oxygen gas flowrate ($O_2$ Flow) and/or oxygen concentration ($O_2$ [%]) of the oxygen gas output 216 generated by the PSA system 10 during the adsorption phase 211 of the PSA cycle are also measured. The concentrated oxygen gas flowrate and/or oxygen concentration is measured in order to verify that the PSA adsorption cycle 211 both starts at the correct time as well as lasts an appropriate or programmably predetermined duration, to verify during the control method described herein, that the PSA adsorption cycle 211 is in sync with the user's breathing cycle 202. In one embodiment, a carbon dioxide (CO2) concentration sensor is used to measure and verify the user's exhalation, as shown in the $CO_2$ concentration ($CO_2$[%]) graph 208 of FIG. 1H. As shown in the CO2 concentration graph 208, the concentration of carbon dioxide gas ($CO_2$[%]) in the gas composition of a user's breathing flow will increase during the exhalation phase, whereas during the user's inhalation phase, no or only trace amounts of carbon dioxide will be measured. These different sensor data 204, 206, 208 are measured at a high frequency, such as 200 Hz, to dynamically and substantially continuously detect changes in the measured parameters during the user's breathing cycle 202. During the measurement period, a synchronization algorithm is used to match the user's breathing pattern data with the pulsed PSA oxygen output, to control the PSA system 10 such that the enriched oxygen product 216 is produced and/or outputted to the user precisely when physiologically most useful. A non-limiting example of one embodiment of the synchronization algorithm is illustrated by the control method 400 shown in FIG. 4, where oxygen output 216 is provided by an adsorption phase 211 initiated, for example, by a controller included in the PSA system 10 or oxygen concentrator, at a time when the end of the user's exhalation phase and/or the beginning of the user's inhalation phase is detected and/or determined using one or more, or a combination of, the sensor outputs 204, 206, 208. This synchronization algorithm could utilize proportional-integral (PI) control or various other control algorithms based on measured and/or compiled sensor data. Further, this synchronization algorithm may utilize a circular buffer data structure to read/write digital sensor values 204, 206, 208 onto a removable memory device installed to the PSA system 10 and/or the oxygen concentrator including the PSA system 10, such as an SD card, and/or to store the digital sensor values 204, 206, 208 to a read only memory (RAM) storage of the microprocessor of the PSA system 10 (see, for example, microcontroller 814 shown in FIG. 8). Data stored to the removable memory device, including, for example, digital sensor values 204, 206, 208, can be selectively read (collected) from the removable memory device for data processing, for example, by server including one or more algorithms configured to perform predictive analysis of the user's breathing, such that the collected data and predictive analysis generated using the collected data can be user to improve the accuracy of the synchronization algorithm based on the cumulative collected data and user's breathing cycle history derived therefrom.

Figure 1I:
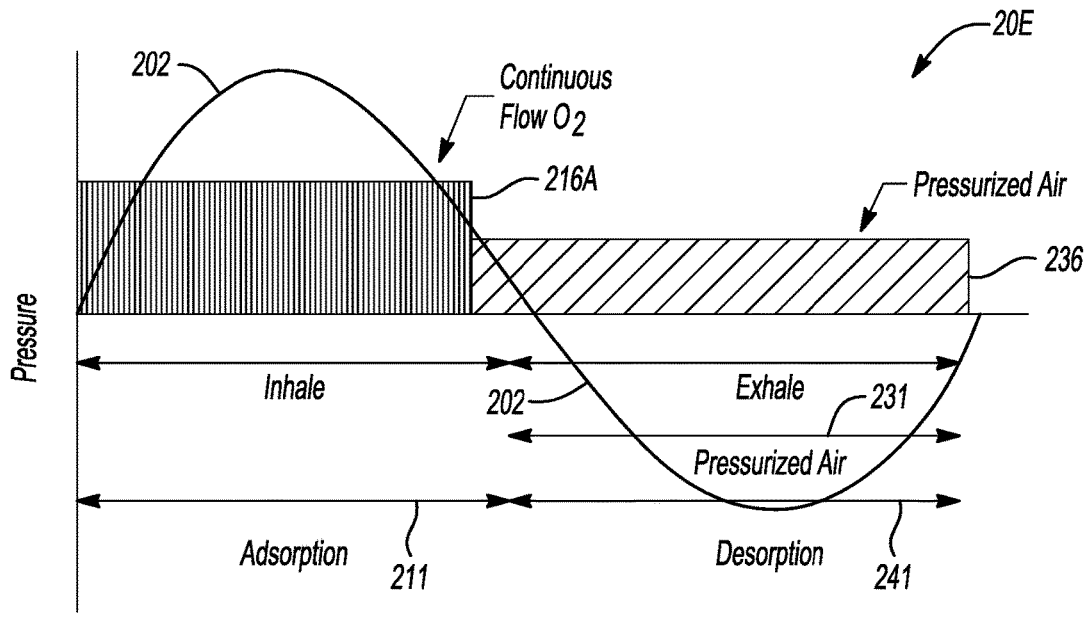
FIG. 1I shows a graph illustrating the user breathing flow phases during a breathing cycle in conjunction with PSA phases of a PSA cycle of an oxygen concentrator system of the present invention.

In the example illustrated by the phase graph 20E shown in FIG. 1I, continuous flow oxygen concentrated gas 216A can be delivered by the PSA system 10 to the user as determined by the control algorithm 400 and/or using sensor outputs 204, 206, 208, such that the oxygen output 216A is delivered to the user automatically at variable selectable times and at variable and/or selectable doses during inhalation/exhalation period of the user's breathing cycle 202. The cycle time of the pressure swing adsorption system, including the time that the PSA cycle is in the adsorption phase 211 and the time that the PSA cycle is in the desorption phase 241, is variable from one inhalation/exhalation period of the user's breathing cycle 202 to the next inhalation/exhalation period of the user's breathing cycle 202, and determined based on the user breathing pattern and the control algorithm of the PSA system 10. Hence, with the present invention, the oxygen product gas 216A is produced during only the useful periods of the breathing cycle, such as the first 70% of the inhalation phase, also referred to herein as the useful period of the inhalation phase, and the end of the exhalation phase, also referred to herein as the pre-inhalation period of the exhalation phase. In some embodiments of the PSA system 10, when oxygen gas 216A is not being produced by the PSA system 10, such as during a desorption phase 241 activated during most of the exhalation phase of a user's breathing cycle, pressurized air 236 is outputted from the PSA system 10 and/or the oxygen concentrator, to the user. In one example, the pressurized air 236 is outputted during a pressurized air phase 231 which corresponds in time with the desorption phase 241. This pressurized air output 236 helps keep the user's airways open during exhalation by providing a positive end expiratory pressure (PEEP) and could be psychologically useful in improving user comfort with their oxygen concentrator or by allowing the oxygen concentrator to function as an integrated CPAP or BiPAP device, or mechanical ventilator. This pressurized air 236 can also be used to flush out dead space in a CPAP mask or other masks for breathing therein.

Figure 1J:
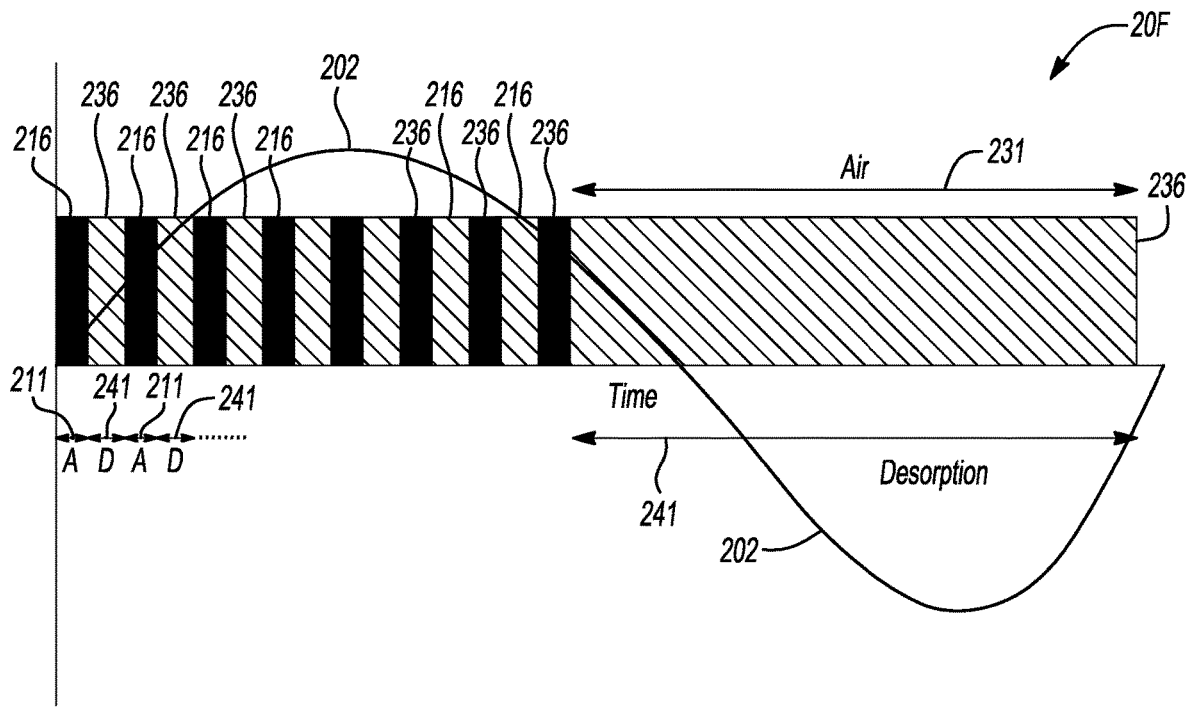
FIG. 1J shows a graph illustrating the user breathing flow phases during a breathing cycle in conjunction with PSA phases of a PSA cycle of an oxygen concentrator system of the present invention.

In another example illustrated by the phase graph 20F shown in FIG. 1J, an algorithm is illustrated which controls the delivery of oxygen concentrated gas 216 to the user of an oxygen concentrator at variable selectable times and at variable and/or selectable doses, where in the present example, alternating volumes of oxygen concentrated gas 216 and pressurized air 236 are delivered to the user during the productive portion of the breathing cycle 202, beginning at a pre-inhalation period at the end of the exhalation phase and/or beginning at the onset of the inhalation phase, and continuing to the beginning of the dead space period of the inhalation phase. A non-productive portion of the breathing cycle 202 can be described herein as including the dead space period of the inhalation phase and the non-useful period of the exhalation phase.

The cycle times of the alternating adsorption (A) phases 211 and the desorption (D) phases 241 executed by the PSA system during the productive portion of the breathing cycle 202 are variable based on the user breathing pattern 202, however the PSA cycle time, of each pair of adsorption and desorption phases 211, 241 defining a PSA cycle, is much faster than standard inhalation and exhalation time periods. Hence, with the present invention, the oxygen product gas 216 is produced intermittently during the inhalation phase due to the rapid PSA cycle time and the multiple PSA cycles which are executed during the inhalation phase, as shown in FIG. 1J. In the example shown, the PSA cycle time can be determined as the time elapsed from the start of one adsorption phase 211 to the start of the subsequent (next) adsorption phase 211, which includes the duration of the desorption phase 241 occurring between the adsorption phases 211. During the desorption (D) phase 241 of each of these rapid PSA cycles, pressurized air 236 can be outputted in order to maintain positive pressure to the user, and to allow at least some useful gas exchange while oxygen concentrated gas 216 is not being produced. This rapid PSA cycle can operate such that miniature pulses of oxygen concentrated gas 216 and pressurized air 236 are intermittently produced only during the useful period of the breathing cycle 202, where the useful period in the illustrative example includes the first 70% of the duration of an inhalation phase and the end period of the exhalation phase preceding the inhalation phase. In one example, approximately the last 10% of the preceding exhalation phase is included in the useful period. In the present example, during the non-useful periods of the breathing cycle, where the non-useful periods can include most of the exhalation phase of a user's breathing cycle and/or the anatomical dead space period of a user's inhalation phase, pressurized air 236 can be output to the user and a longer duration PSA desorption phase can occur, as shown in FIG. 1J. This longer duration output of pressurized air 236 during the non-useful period including most of the exhalation phase helps to keep airways open during exhalation by providing a positive end expiratory pressure (PEEP) to the user, which can be an advantage of the PSA system described herein, where the PEEP provided by the longer duration of pressurized air 236 output during the non-useful period(s) is psychologically useful in improving user comfort with their oxygen concentrator and/or by allowing the oxygen concentrator to function as an integrated CPAP or BiPAP device. Alternatively, with a rapid PSA system 10, two adsorbent beds can be alternately cycled with rapid PSA cycle times to produce miniature pulses of oxygen, creating a continuous flow of oxygen on demand when physiologically useful. As used herein, the term "miniature pulses of oxygen" in intended to mean that more than one oxygen pulse is output per period of respiration, e.g., each of the more than one pulses of oxygen gas outputted per breath consisting of an inhalation phase and an adjacent (either preceding or succeeding) exhalation phase is considered a miniature pulse. In this configuration, when oxygen is not being produced, the oxygen generator ceases operation, saving approximately 70% on energy. In some embodiments, the oxygen concentrator operating in the rapid cycle PSA mode shown in FIG. 1J, could store some non-outputted oxygen volume in a reserve tank, for release to the user during higher peak oxygen demand periods occurring during the breathing cycle 202. In instances of non-spontaneous user breathing, the oxygen output 216 can be set at a certain breathing frequency, for example 12 breaths per minute, and the pressurized air 236 can be used to provide a PEEP during exhalation, allowing the oxygen concentrator to provide ventilatory support and/or function as a mechanical ventilator where no oxygen-air blending is required, but rather where both the PEEP air pressure 236 from an air blower and oxygen output 236 from the oxygen source such as an oxygen concentrator as described herein are produced and dynamically adjusted on demand for the user.

Figure 1K:
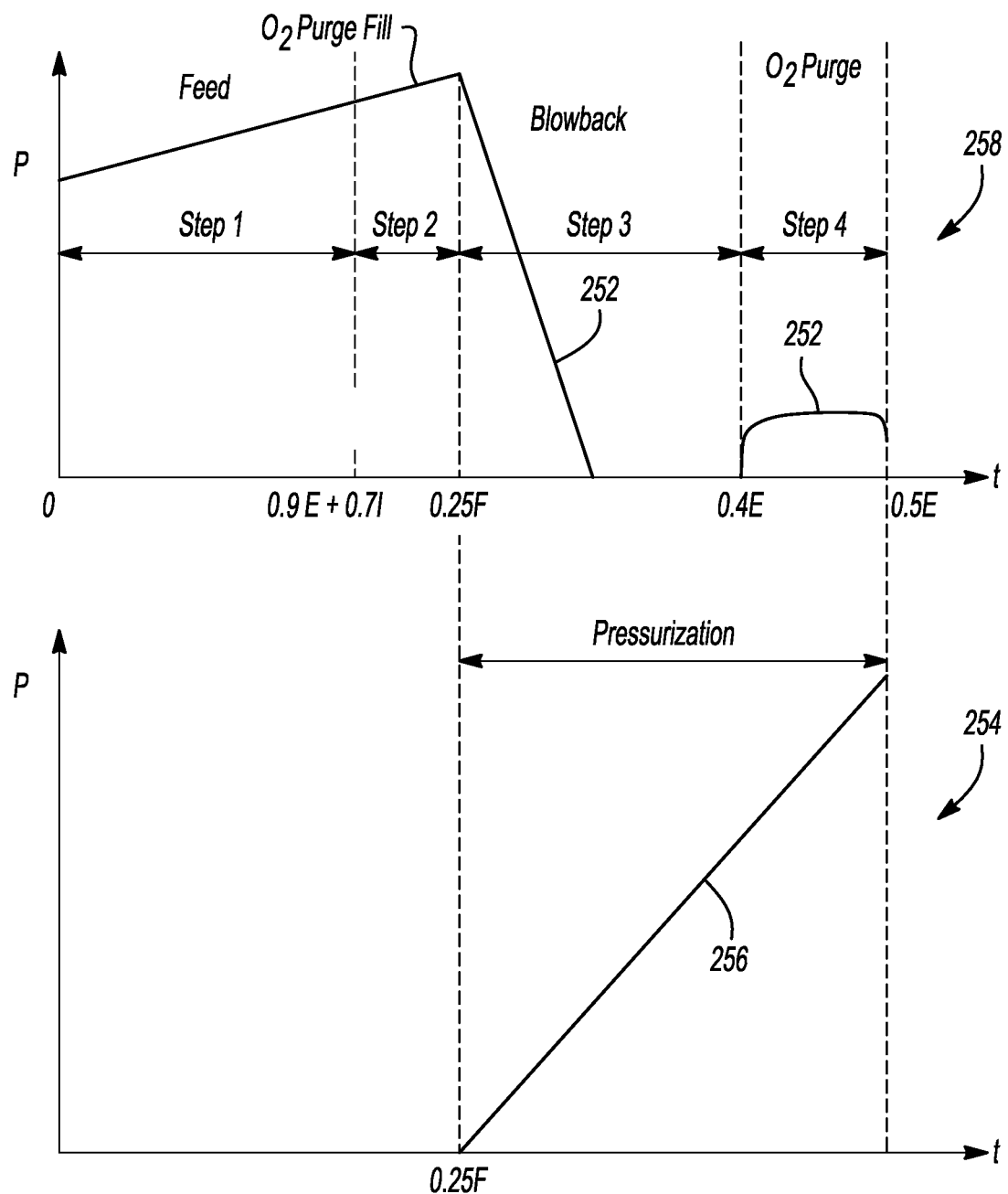
FIG. 1K shows a graph illustrating the pressure phases of the adsorption column of a PSA system of the present invention.
Figure 1L:
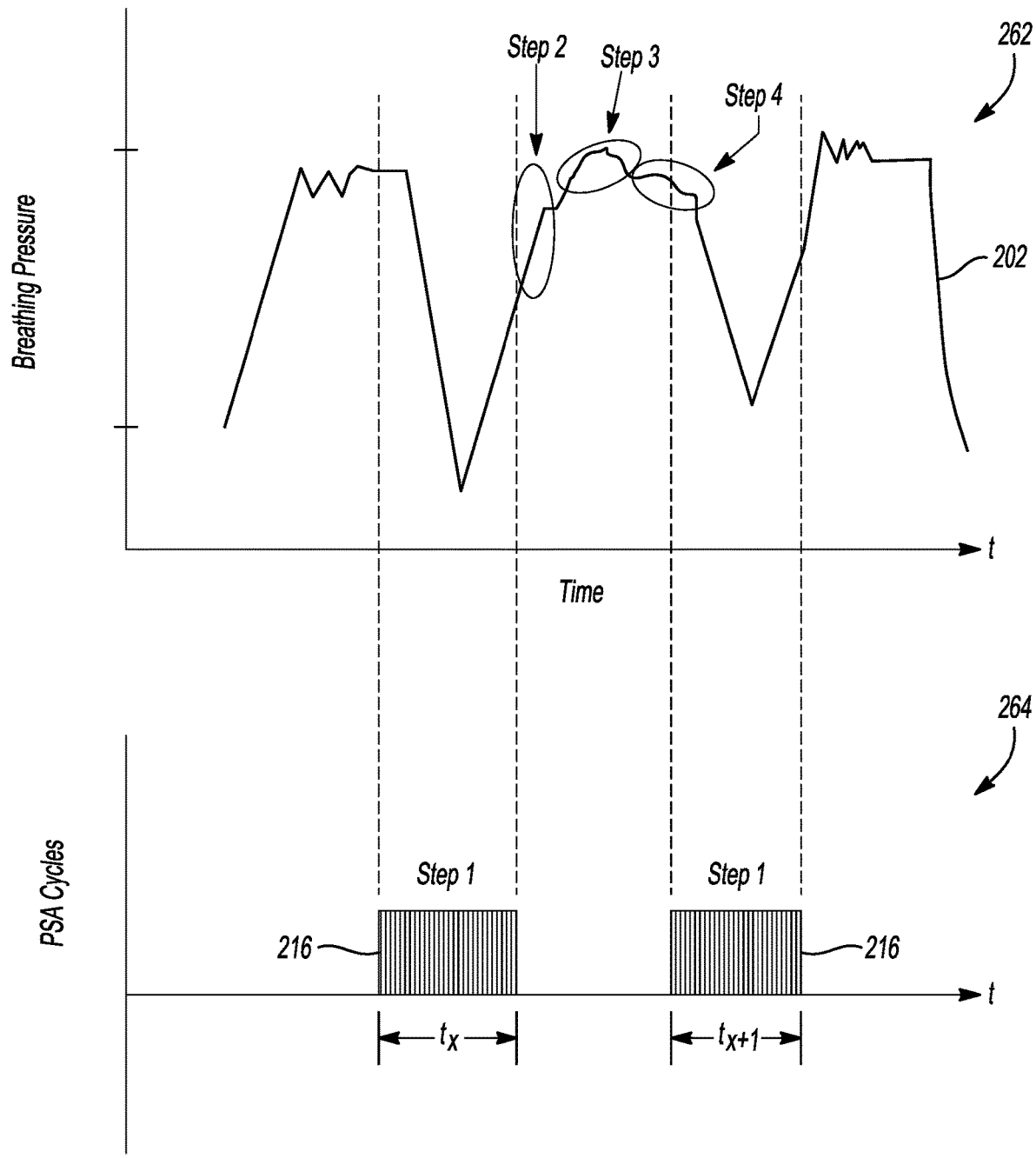
FIG. 1L shows a graph illustrating breathing pressure using the flow phases of user breathing cycles in conjunction with oxygen output from an oxygen concentrator in the present invention.

As illustrated in FIG. 1K, viewed in conjunction with the example breathing cycle shown in FIG. 1L, the steps of the pressure swing adsorption system 10 are synchronized with different pressure phases of a user breathing cycle 202. Some of these PSA steps could has a fixed duration, e.g., be performed in a fixed amount of time, whereas other steps may have a variable duration, e.g., be performed in an amount of time which may vary from one breath to another in the breathing cycle. In the example illustrated by FIG. 1K, in graph 258, the air pressure 252 in an adsorbent column 220, 320 of the PSA system 10 is shown, in conjunction with the air pressure 256 in an inlet air volume tank of the PSA system 10 shown in graph 254, where the variation in the pressures 252, 256 is shown over time and during steps of the PSA system 10. For example, in one embodiment the pressurization step of the PSA cycle is the fixed amount of time required to pressurize the adsorbent column with X cubic inches of air at X liter per minute (LPM) flowrate. In some embodiments, the inlet air volume tank is accumulating pressurized air during the blowback and O2 purge stages of the PSA cycle, at an inlet air volume tank pressure 256. Hence, during the pulsed PSA cycle in this example, the pressurization step would occur at the same time as the blowback and O2 purge steps as shown in FIG. 1K. In some embodiments, the pressurization and feed steps of the PSA cycle are the same (STEP 1). In one embodiment, the feed step would be a variable amount of time for adsorption/oxygen production. This feed step would be synchronized with user breathing such that in some embodiments the feed step begins near the end of the exhalation phase, e.g., after approximately 90% of the exhalation phase is completed (0.9E) during the pre-inhalation period of the exhalation phase, and terminates at 70-80% of the inhalation phase (0.7I), e.g., at the beginning of the anatomical dead space period (0.7I). In one embodiment, the O2 purge fill step (STEP 2) is a variable amount of time based on O2 production during feed as well as the purge to feed volume desired. The purge to feed ratio is generally a fixed ratio, and affects the purity of the raffinate product, in this case oxygen. In some instances, this purge to feed ratio is determined based on flowrates and not on volumes. In a preferred embodiment, the O2 purge tank is sized so that the tank volume is filled or nearly filled at a certain purge to feed ratio at most (typical) user breathing rates. In one embodiment, blowback (STEP 3) occurs over a fixed amount of time based on the time required to depressurize the adsorbent column of X volume. In another embodiment, the purge step (STEP 4) is a variable amount of time based on when the end time of the exhalation phase is nearing and/or when oxygen production starts (see graph 264). In one embodiment, the blowback and purge steps are a fixed ratio of one another. In another embodiment, the blowback and purge steps may be combined as one step. Referring to the breathing cycle 202 shown in FIG. 1L, during rise in rate of breathing pressure (during exhalation) 262, after a certain threshold value of breathing pressure 262 is met, STEP 2 starts (see FIGS. 1K and 1L). When slope of breathing pressure rise starts falling (see FIGS. 1K and 1L), STEP 3 starts and lasts until after local maxima value reached. When breathing pressure 262 starts falling or flatlines, both in value and rate of change, Step 4 starts (see FIGS. 1K and 1L. Step 4 terminates near end of the exhalation phase, then STEP 1 starts for the subsequent inhale/exhale phases of the user's next breath flow. STEP 1 continues through the fall in breathing pressure (inhalation) 262 and then ends when a certain pressure threshold is reached as determined by rise in the breathing pressure value 262 and rate of change. These threshold values and rates of change could be experimentally determined or computed based on mathematical formulas or different control schema, such as multi-predictive control. To make the prediction of timing of inhalation versus exhalation phases more accurate, as well as determining when to switch PSA steps, a plurality of sensors could be used to correlate data, for example, as described related to FIG. 1H. These different types of sensors can include mass air flow sensors, O2 concentration sensors, and CO2 concentration sensors. Capnography with CO2 concentration sensor could be used to determine, e.g., diagnosis lung obstructions and/or user oxygen saturation on a breath by breath basis, allowing for the automatic adjustment of oxygen flowrate and volume output from PSA system 10 to the user on a breath by breath basis. This data allows for dynamic air compressor output feedback control, which would allow the oxygen output 216 from the oxygen concentrator to be adjusted at a very fast rate, for example, in a rapid PSA cycle configuration. In some embodiments, fraction of inspired oxygen (FiO2) sensors can also be used to measure the amount of oxygen inspired per breath and to output a volume/flowrate of oxygen per breath that keeps the FiO2 level constant in accordance with recognized clinical standards. In other embodiments, a pulse oximeter can be connected to the oxygen concentrator device via a connector or remotely connected to the oxygen concentrator via a near field communication method such as Bluetooth in order to provide the oxygen concentrator control system with blood oxygen saturation, SpO2 or PaO2, data. This could allow for the on demand production of oxygen wherein the oxygen flowrate and/or oxygen gas volume produced is dynamically adjusted via feedback control or other control algorithm on a breath by breath basis to dynamically maintain constant blood oxygen saturations within recognized clinical standards, without users being required to manually and/or continually adjust the flowrate of their oxygen concentrator. Dynamic adjustment of the oxygen flowrate and/or volume outputted to the user on a breath by breath basis present the advantage of improving the clinical efficacy of long term oxygen therapy during situations such as sleep or exercise where users have a limited ability to manually adjust their oxygen flowrate settings on their oxygen concentrator machine.

In other embodiments, the oxygen output from the oxygen concentrator can be dynamically adjusted during exercise based on other sensor measurements such as the volume of oxygen consumed per minute (VO2), which can be measured using an oxygen concentration sensor and calculated by taking the volume of oxygen inspired per minute and subtracting it from the volume of oxygen expired per minute. This VO2 value over time can be used to determine whether the body is oxygen deficient in the beginning of exercise, for example when the rate of VO2 is increasing. This means that the volume of oxygen naturally inspired was unable to meet the human body's biochemical ATP (Adenosine 5'-triphosphate) demands at the beginning of exercise. The volume of CO2 produced per minute (VCO2) can be measured using a CO2 concentration sensor and calculated by finding the volume of CO2 expired per minute and subtracting the volume of CO2 inspired per minute. These VO2 and VCO2 values can be used to calculate respiratory exchange ratio (RER), which can be used to determine cardiovascular performance and changing environmental conditions related to user exercise and fat oxidation that are important in athletics. Supplemental oxygen could be useful to athletes or even those with chronic lung diseases in situations where there is an oxygen deficit at the beginning of exercise as well as excess post-oxygen consumption after the exercise has ended. The present disclosure details a method of identifying these changes in user breathing conditions during exercise using sensor(s) and compensating with additional supplemental oxygen in a manner that is most beneficial for the user and efficient for the oxygen production system, while wasting as little oxygen as possible.

As illustrated in FIG. 1L, a pressure versus time graph 262 of a user breathing cycle 202 is shown. In this illustration, STEP 1 is a combined pressurization and feed step wherein oxygen output 216 is produced. This oxygen output time tx in STEP 1 corresponds to certain times/portion(s) of the breathing pressure curve 262 therein. STEP 2 represents the O2 purge fill phase of the PSA cycle, and corresponds to certain times/portion(s) of the breathing pressure curve 262 therein. STEP 3 represents the blowback step in the PSA cycle, and corresponds to certain times/portion(s) of the breathing pressure data therein. STEP 4 represents the O2 purge phase 221 in the PSA cycle, and corresponds to certain times/portion(s) of the breathing pressure curve therein. As shown in FIG. 1L, the PSA cycle repeats, beginning again with STEP 1, where oxygen output 216 is produced for an oxygen output time tx+1. In one example, oxygen concentrator and/or PSA system 10 is configured such that the oxygen output times tx and tx+1 are equal and constant for each inhalation/exhalation phase pair of the breathing cycle 202. In some embodiments, the oxygen concentrator and/or PSA system 10 is configured such that the oxygen output times tx and tx+1 are determined by the user's breathing cycle 202 using sensor inputs from one or more breathing cycle sensors 16, 18 (see FIG. 1M), which may include breathing pressure input 262 received from the pressure sensor 16, and/or an algorithm for determining the duration of the oxygen output time for each inhalation/exhalation phase pair, where the duration of oxygen output time may be variable from each inhalation/exhalation phase pair to the next, for example, during a period of erratic user breathing as shown by the variation in breathing pressure 262 in FIG. 1L, such that tx and tx+1 may have different durations. In some embodiments, the onset of the oxygen output times tx, tx+1 may be determined based on the user's breathing cycle 202 using sensor inputs from one or more breathing cycle sensors 16, 18 (see FIG. 1M), which may include breathing pressure 262, and/or an algorithm for determining the time to initiate oxygen output 216 (onset time) for each inhalation/exhalation phase pair, where the onset time for each cycle of oxygen output 216 may be variable from each inhalation/exhalation phase pair to the next.

Figure 1M:
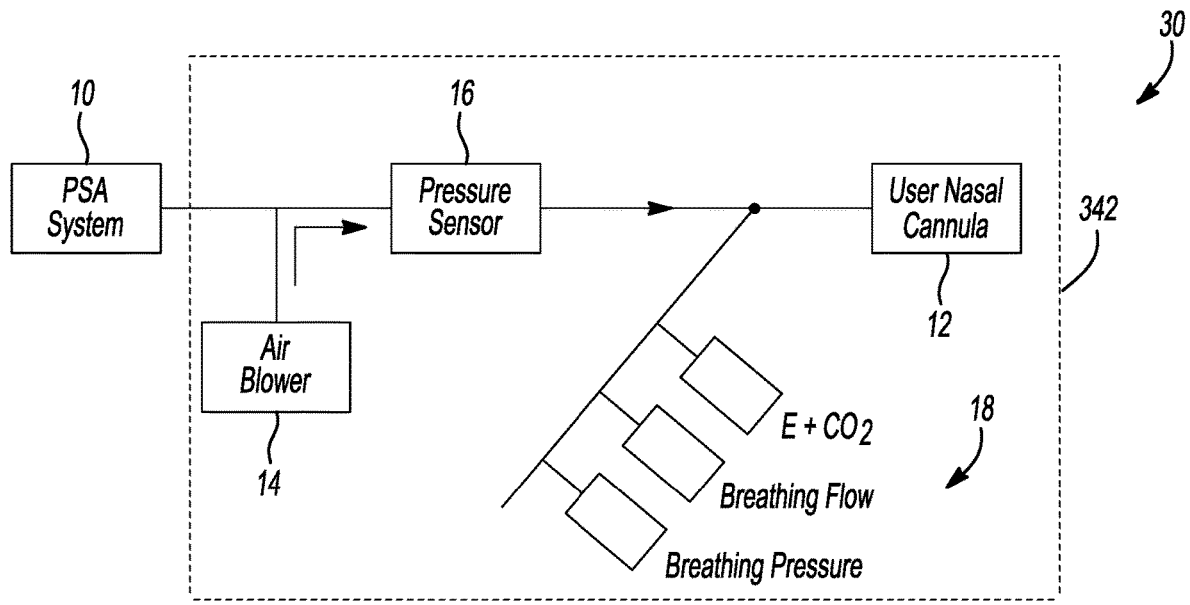
FIG. 1M shows a schematic diagram of an oxygen concentrator breathing circuit for use with an oxygen delivery device.

Referring to FIG. 1M, a non-limiting example of an oxygen concentrator is shown, including a breathing circuit 30 a PSA system 10 in fluid communication with a cannula 12, such that the PSA system 10 can selectively provide an outputted gas to the cannula 12, where the outputted gas can be an oxygen enriched gas 216 and/or pressurized air 236. The oxygen concentrator and/or breathing circuit 30 includes one or more breathing cycle sensors 16, 18 which are in fluid communication with the cannula 12, and configured to sense and/or measure data values and rates of change thereof to allow the determination of various phases of a user's breathing cycle 202, such as exhalation and inhalation, by a controller in communication with the breathing cycle sensors 16, 18, when the oxygen concentrator is in use by the user. In one example, the breathing circuit 30 optionally includes an air blower 14 which can be actuated to output pressurized air 236 to the cannula 12, for output to the user. The controller can be a controller 380 of the PSA system 10, which may be in communication with one or more of the air blower 14, the breathing pressure sensor 16, and/or the breathing cycle sensors 18. In one example, the breathing pressure sensor 16, the breathing cycle sensors 18, and/or the air blower 14 can be arranged to define an oxygen delivery device 342. The oxygen delivery device 342 can be in communication with the controller 380 of the PSA system 10, wherein in this example, the controller 380 can receive data from the sensors 16, 18 and can include one or more algorithm which can be used for determining and/or estimating the breathing cycle 202 of the user, and/or generating instructions and/or commands to the PSA system 10 and/or the air blower 14 for the selective operation of these elements. In one example, the controller 380 can be included in the oxygen delivery device 342 and/or otherwise included in the oxygen concentrator such that the controller 380 is in communication with the breathing circuit 30 to receive data therefrom and to generate instructions and/or commands for the operation thereof.

In the example shown, the PSA system 10, the air blower 14, the breathing pressure sensor 16, and the breathing cycle sensors 18 are each in fluid communication with a nasal cannula 12, wherein the nasal cannula 12 is wearable by the user to deliver the oxygen enriched gas 216 and/or pressurized air 236 from the PSA system 10 and/or air blower 14 to the user's respiratory system, for example, via the user's nasal passages. These sensor data measurements could include, but are not limited to: EtCO2, CO2 concentration, O2 concentration, breathing flowrates, breathing pressures, etc. In this diagram, any PSA system 10, including but not limited to the exemplary PSA systems 200, 300, 301, 302, 303, 304, 305, 306, 307, 500, 600, 700, 850, 860, 870, 880, 900, could be used wherein the oxygen output 216 can be continuous or intermittent. Other types of oxygen generators/storage devices could be substituted for the PSA system 10 shown in FIG. 1M, in some embodiments of this disclosure. These other types of oxygen generators/storage devices include cryogenic distillation, gaseous oxygen tanks, liquid oxygen tanks, membrane oxygen generators, thermal swing adsorption oxygen generators, chemical based oxygen generators, and hybrid systems thereof integrated with or separate from the PSA system 10. An air blower 14 can also be integrated to generate positive end expiratory pressure (PEEP) during the exhalation phases of a user's breathing cycle 202. Further, check valve(s) and wye tubing could be incorporated into the breathing circuit 30, to separate the sensors 16, 18 and output oxygen/air, allowing for more reliable data readings from the sensor(s) 16, 18 during both inhalation and/or exhalation phases of the user's breathing cycle 202. In some of the embodiments disclosed herein, the sensor outputs from sensors 16, 18 can be received by a controller, such as a controller 380, 580, 680, 814, and inputted to and/or utilized by one or more algorithms which may be stored to or accessed by the controller, to determine one or more of an oxygen output 216 duration time, onset time, etc. and/or to control operation of the PSA system 10 and/or other components of the oxygen concentrator including, for example, an air blower 14, etc. In a non-limiting example, one or more of the pressure sensor 16, air blower 14, user breathing cycle sensors 18, and/or nasal cannula 12 can be included in an oxygen delivery device 342 used in conjunction with a PSA system 10, as described further herein.

Figure 1N:
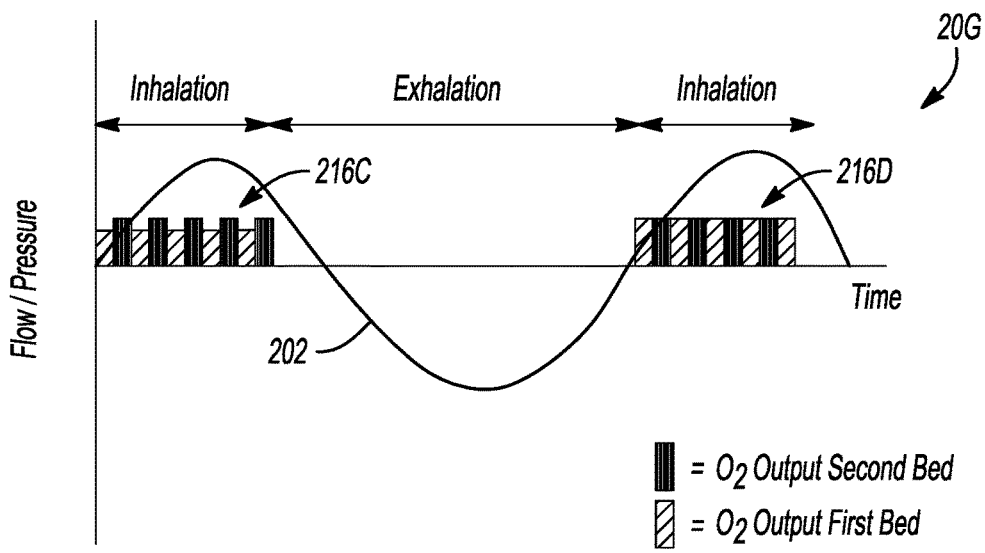
FIG. 1N shows a graph illustrating the user breathing flow phases during user breathing cycles in conjunction with that of PSA phases of a PSA cycle of an oxygen concentrator in the present invention.

As illustrated by the phase graph 20G shown in in FIG. 1N, oxygen can be output from an oxygen volume and/or flowrate can be dynamically adjusted during the physiologically useful phases of respiration during a user's breathing cycle 202. In one embodiment disclosed herein, a pressure swing adsorption system 10 with rapid PSA cycle times can output one or more pulses of oxygen of varying volumes/flowrates during a single useful phase of respiration, as illustrated by the oxygen output sequences 216C, 216D shown in FIG. 1N. In the example shown, each of the first and second oxygen output sequences 216C, 216D is comprised of alternating oxygen pulses outputted from first and second adsorbent beds of a PSA system 10. This oxygen volume and/or flowrate output can be dynamically adjusted per pulse or discrete time period (i.e. 50 milliseconds) using proportional valve control, DC motor control, air volume tanks, and/or a combination thereof. Further, during the non-useful phases of the breathing cycle 202, such as during the exhalation phase, the pressure swing adsorption system 10 may be turned OFF in order to reduce energy consumption, allowing for oxygen output to be conserved. In another embodiment, a volume of oxygen may be produced and/or accumulated and stored using an air volume tank, for example, during the non-productive portion of the breathing cycle 202 (the dead space period of the inhalation cycle and the non-useful period of the exhalation cycle), and then released during a productive portion of the breathing cycle 202, for example, during the useful period of the inhalation phase and/or during the pre-inhalation period of the exhalation phase. In some embodiments, particularly with rapid PSA cycle times, a pressure swing adsorption system 10 with two or more adsorbent columns, each including an absorbent bed, can be utilized such that each adsorbent column can have, for example, different physical characteristics such as size and oxygen output production capabilities. This could allow for more variation in oxygen concentrator flow output and could allow for the production of complex oxygen flow waveforms that are similar to, e.g., substantially duplicative of, actual user breaths, where the complex oxygen flow waveforms can be created by the controller 380 using algorithms and/or controls strategies including but not limited to: varying cycle times between the adsorbent columns per oxygen pulse, adjusting the oxygen pulse durations, controlling the input air compressor pressure, flowrates, duty cycle, and/or power consumption, storing oxygen output and/or air input in volume tanks, valve control such as proportional valve control that allows for the regulation and/or constriction of gas flowrates and/or pressures, as well as creation of gas output or input waveforms that affect oxygen production or delivery performance and/or physical characteristics. Further, these oxygen output volumes and/or flowrates may be controlled such that the oxygen output volumes and/or flowrates can be varied on a breath by breath basis, as well as on a pulse by pulse basis. The oxygen concentrator can include a controller and/or one or more algorithms that can embody a predictive control schema, which can be used, for example, in conjunction with data collected from sensors 16, 18, to measure a user's breathing flowrates and then integrate to calculate a tidal volume. In some embodiments, a fraction of inspired oxygen (FiO2) percentage, can be set or programmed into the machine in order to clinically saturate an oxygen patient (user) without requiring adjustment of oxygen settings by the user. Miniature oxygen pulses can be output for brief periods of time each, for example 10 milliseconds, such that an oxygen delivery device (see 342 at FIG. 3G) which may include one or more sensors 16, 18, in conjunction with a controller 380, can estimate the amount of oxygen that should be delivered in each oxygen pulse based on rate of change measured in user breathing flow patterns, in order to maintain the FiO2 percentage. In one example, after this O2 pulse is delivered, the control system 380, for example, via an algorithm, verifies the accuracy of the prediction, e.g., the estimate, by integrating the detected user's breathing flowrate during the time period of that oxygen pulse to calculate a tidal volume, as well as to calculate the oxygen volume produced/output during this time period. An actual FiO2 percentage during this brief time period such as 10 milliseconds is calculated, and then, via the controller 380 and/or the oxygen delivery device 342, compensated for in the next oxygen pulse using feedforward control, to bring the FiO2 to the set/programmed percentage. In some embodiments, other metrics for the breathing cycle 202, user respiration and cardiovascular health such as VCO2, VO2, SpO2, SpCO2, and/or PaO2 can be measured by the oxygen concentrator and used to adjust the oxygen volume and/or flowrate from the oxygen concentrator to the user, on a breath by breath basis, as required to maintain clinical oxygenation for the patient, e.g., the oxygen volume and/or flowrate can be adjusted by the controller 3080 and/or oxygen delivery device 342 if the FiO2 percentage maintained is not sufficient for clinical oxygenation for the patient. Further, these other respiration and cardiovascular health metrics can also be used to automatically adjust the FiO2 percentage, via the controller 380 and/or the oxygen concentrator on a breath by breath, or even intra-breath interval, based on factors estimated such as lung obstructions, level of activity, blood oxygen saturations, effectiveness of lung gas exchange, and/or anticipated future oxygen demand.

In some embodiments, one or more algorithms can embody a predictive control schema, which can be used, for example, in conjunction with data collected from the sensors 16, 18, to measure a user's breathing flowrate through one or more breaths, and then manipulate and/or otherwise analyze the collected data to predict and/or estimate the duration of each breathing cycle phase and/or period within a breathing phase, such that the prediction and/or estimation determined therefrom can be used to control initiation and cessation of outputted gas flow at certain times within the flow phases of succeeding breaths of the user. In one example, the control system 380, for example, via an algorithm and data collected during the succeeding breaths of the user, verifies the accuracy of the prediction and/or estimate, and uses the differences between the predicted and/or estimated value and the actual value to increase the accuracy of the prediction and/or estimation algorithms over time. In this example, the algorithms are configured as learning algorithms which are adapted over time and as actual user data is accumulated, to increase the accuracy of the algorithms to predict the individual user's breathing cycle 202 such that the timing, flow rate, volume, etc., of outputted oxygen gas 216 and/or pressurized air 236 can be customized with high accuracy to each breath of the user, on a breath by breath basis.

III. Exemplary Oxygen Concentrator

An exemplary oxygen concentrator including a PSA system 10, for example, a PSA system 300, 301, 302, 303, 304, 305, 306, 307, 500, 600, 700, 850, 860, 870, 880, 900 as described in multiple embodiments, is provided herein and illustrated by the accompanying figures. In one example, an oxygen concentrator is provided with a single adsorption bed that uses the pressure swing adsorption process to provide oxygen enriched gas to a user. In this example, the pressure swing adsorption system uses a cyclical adsorption process where inlet gas, from atmospheric gases, is pressurized and separated to produce a raffinate product. Specifically, the inlet gas can be atmospheric air and the product produced by the pressure swing adsorption is an enriched oxygen product such that the oxygen concentration of the product gas exceeds that of normal atmospheric air, which is 21%.

Figure 2:
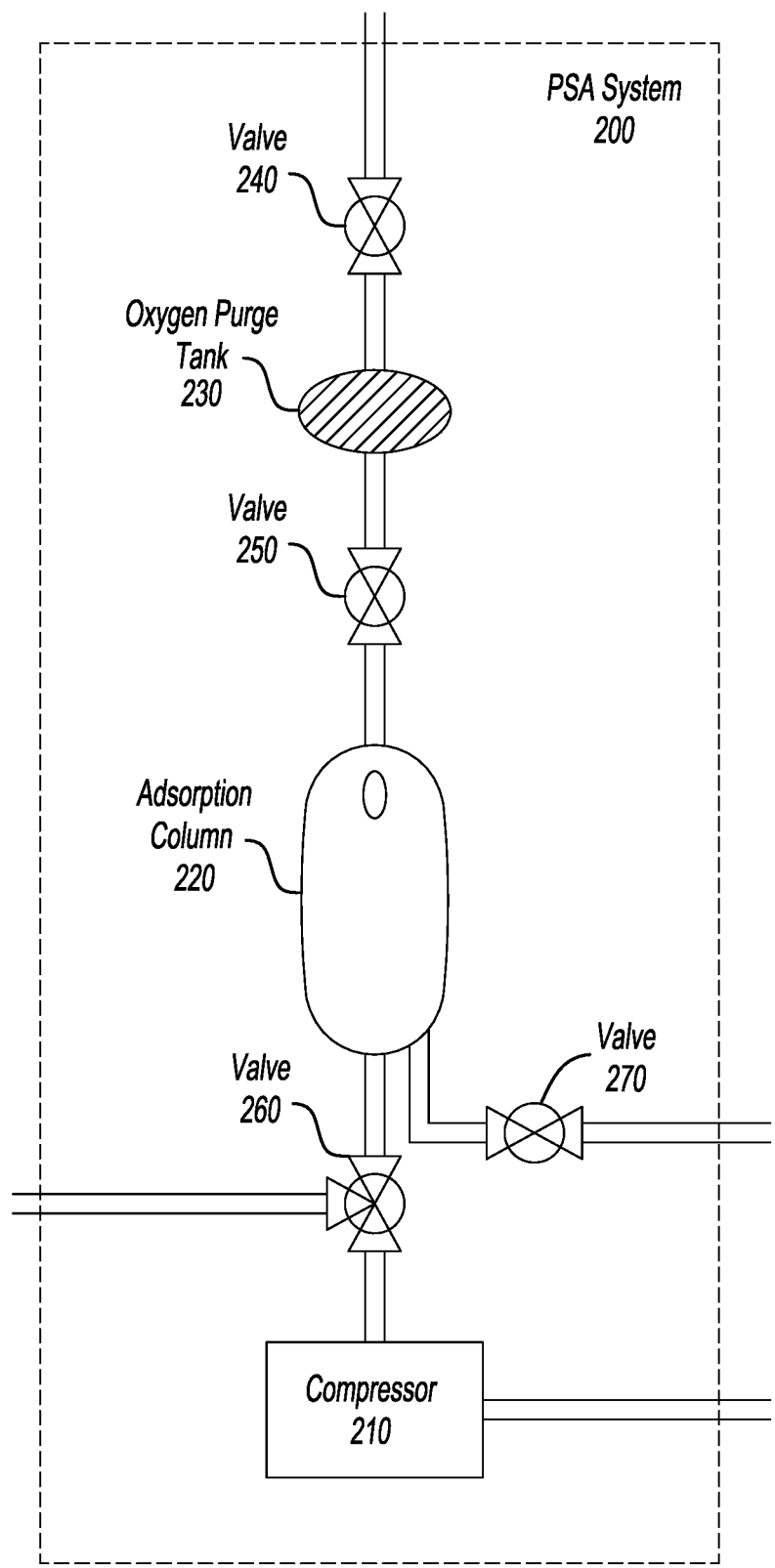
FIG. 2 shows a schematic diagram of a Pressure Swing Adsorption system according to some embodiments.

Referring now to FIG. 2, shown is a first example of a pulsed pressure swing adsorption system. In this example, a pressure swing adsorption (PSA) system 200 comprises a compressor 210, an adsorption column 220, and an oxygen purge tank 230. The compressor 210, adsorption column 220, and oxygen purge tank 230 can be connected to each other in series. A plurality of valves such as valve 240, valve 250, valve 260, and valve 270 operably connect each of the compressor 210, adsorption column 220, and oxygen purge tank 230 and act as gates for either allowing or blocking gas to flow through each of the valves 240, 250, 260, 270.

During an adsorption phase 211 of the PSA system 200, the compressor 210 compresses atmospheric air, also referred to herein as feed air, pressurizes the atmospheric air, and delivers the pressurized air 236 to the adsorption column 220. The atmospheric air is substantially comprised of oxygen and nitrogen gas. Once the pressurized air 236 is delivered to the adsorption column 220, the adsorption column 220 will adsorb the nitrogen gas from the pressurized air 236, such that the remaining pressurized air 236 becomes oxygen enriched, e.g., is comprised of a greater percentage of oxygen as compared to the atmospheric air. As shown in FIG. 2, the oxygen enriched gas 216, also referred to herein as oxygen gas, comprising the remaining pressurized air 236 continues to flow through an open valve 250 to the oxygen purge tank 230. The oxygen gas will continue to flow through the oxygen purge tank 230 and to a user who inhales the oxygen gas 216 generated by, e.g., outputted from, the PSA system 200.

In one example, the adsorption column 220 contains an adsorption bed, such as adsorption bed 755 shown in FIG. 7, comprising molecular sieves such as zeolite or Lithium Type-X zeolite (Li—X zeolite). During the adsorption phase 211, the zeolite will adsorb the atmospheric nitrogen from the pressurized air, allowing oxygen to pass through the adsorption column 220 and into the oxygen purge tank 230.

At a desorption phase 241 of the PSA cycle of the PSA system 200, valve 250 is closed and blocks oxygen from flowing between the adsorption column 220 and the oxygen purge tank 230. During the desorption phase 241, valve 270 is open allowing the adsorption column 220 to desorb, such that pressurized nitrogen gas stored in the adsorption column 220 during the adsorption phase 211 is depressurized from the adsorption bed and exits the PSA system 200 via the open valve 270, back into the atmosphere, therein regenerating the adsorbent bed. Once the nitrogen is released from the adsorption column 220 through the open valve 270, a subsequent adsorption phase 211 is initiated, whereby via the process of adsorption enriched oxygen can be provided to a user, as previously described. The PSA system 200 repeats the alternating desorption and adsorption phases 241, 211 in a PSA cycle, to generate and provide oxygen gas to a user of the oxygen concentrator including the PSA system 200.

IV. Pulsed PSA System

FIGS. 3A-I illustrate examples of a pressure swing adsorption system. In this example, referring to FIG. 3A, a pressure swing adsorption system 300 is described. The pressure swing adsorption system 300 generates raffinate product such as enriched oxygen in a non-continuous manner, in oxygen pulses 216. In one example, the PSA system 300 is a pulsed-pressure swing adsorption system. The PSA system 300 minimizes oxygen output waste by only providing oxygen gas to a user during the portion of the user's breathing cycle 202 where the oxygen gas is physiologically useful to the user. In some embodiments, the PSA system 300 will not release oxygen to the user during the user's exhalation phase, or during the later period of the inhalation phase corresponding to the anatomical dead space period.

In this example, illustrated in FIG. 3A, the PSA system 300 comprises a compressor 310, an adsorption column 320, and an oxygen purge tank 330. The compressor 310, adsorption column 320, and oxygen purge tank 330 can be connected to each other in series as shown in FIG. 2. A plurality of valves such as valve 340, valve 350, valve 360, and valve 370 operably connects each of the compressor 310, adsorption column 320, and oxygen purge tank 330 and acts as gates for either allowing or blocking gas to flow through each of the valves 340, 350, 360 and 370. The PSA system 300 can also include a controller 380 which can monitor and control the amount and direction of flow of the gases by controlling the valves 340, 350, 360, and 370. In one example, the valves 340, 350, and 370 are two-way solenoid valves and valve 360 is a 3-way solenoid valve. The memory of the controller 380 can include, by way of example, sufficient read only memory (ROM), Random Access Memory (RAM), electrically-erasable programmable read only memory (EEPROM), etc., i.e., non-transient/tangible machine memory optical memory, flash or other solid state memory, and the like of a size and speed sufficient to store data received, for example, from sensors 16, 18, and/or an oxygen delivery device 342, and to store one or more algorithms and/or control strategies for selectively actuating the PSA system 300 including one or more of a plurality of valves, to generate oxygen gas, to manipulate data received by the controller, and/or to execute the algorithms and/or control strategies stored thereon. Transitory memory such as random access memory (RAM) and electrically-erasable programmable read-only memory (EEPROM) may also be included, along with other required circuitry (not shown), including but not limited to a high-speed clock, current/voltage/temperature/speed/position sensing circuitry, analog-to-digital (A/D) circuitry, digital-to-analog (D/A) circuitry, a digital signal processor, and any necessary input/output (I/O) devices and other signal conditioning and/or buffer circuitry, as required to execute the methods and processes described herein.

In the present example, valve 360 is a three-position or three-way valve. In one position, valve 360 connects an outlet of compressor 310 output to an inlet of adsorption column 320 while blocking flow to an air release to the atmosphere. In a second position, valve 360 connects the outlet of the compressor 310 to the air release while blocking flow to the adsorption column 320. Valve 370 can be a normally-closed two-way solenoid valve which selectively connects the inlet of adsorption column 320 (or, alternatively, a separate port) to the nitrogen release. Valve 350 can be a normally-closed two-way solenoid valve which selectively connects an outlet of adsorption column 320 to an inlet of an oxygen purge tank 330. An outlet of adsorption column 320 is connected to an inlet of oxygen purge tank 330 through valve 350. Oxygen purge tank 330 provides a volume for storage of concentrated and/or enriched oxygen gas 216. Valve 340 can be a normally-closed two-way solenoid valve which selectively connects an outlet of the oxygen purge tank 330 to a release such that a user can breathe in the oxygen gas 216 from the oxygen purge tank 330. In one example, controller 380 can control and change the state of valves 340, 350, 360, and 370 to switch the system among the several PSA phases 211, 221, 231, 241, described in detail below. The controller 380 synchronizes execution of the PSA phases 211, 221, 231, 241 performed by the PSA system 300 with the user's breathing cycle 202 such that oxygen gas 216 is selectively output during the useful portion of each inhalation phase and such that oxygen gas 216 is not output when not physiologically useful to the user, in accordance with one or more control algorithms executed by the controller 380.

FIGS. 3B-3E show the flow and direction of gases at the different PSA phases 211, 221, 231, 241 of the PSA system 300 occurring during an inhalation phase and subsequent exhalation phase of a user's breathing cycle 202. As illustrated in FIG. 1E, the PSA phases of a PSA cycle of operation of the PSA system 300 are an adsorption phase 211, oxygen purge phase 221, pressure equalization phase 231, and desorption phase 241. As illustrated in FIG. 1E, the phases of the PSA cycle are synchronized with the inhalation and exhalation phases of the user's breathing cycle 202. In the example shown and referring to FIG. 1E, the adsorption phase 211 is synchronized, e.g., in sync, with the portion of the inhalation phase not including the anatomical dead space period. The oxygen purge phase 221 is in sync with the anatomical dead space period. The pressure equalization phase 231 is in sync with a first portion of the user's exhalation period. And the desorption phase 241 is in sync with a second portion of the user's exhalation period.

In an illustrative example, the adsorption phase 211, synced with a user's inhalation period, has a duration of about or approximately 1.5 seconds. The oxygen purge phase 221, synced with a user's anatomical dead space period and the pressure equalization phase 231, synced with the first portion of the user's exhalation period, each have a duration of about or approximately 0.5 seconds. The desorption phase 241, synced with the second portion of the user's exhalation period, has a duration of about or approximately 2.5 seconds. The example breathing cycle 202 and the PSA cycle times provided herein are merely illustrative of that of an average user of the oxygen concentrator, and as such are non-limiting. Breathing rates and inhalation to exhalation time ratios are unique to each user. As further described herein, the oxygen concentrator of the present disclosure can include a control system, executed for example, by a controller 380, 580, designed to detect the length of each inhalation and exhalation phase of an individual user, and utilize data generated from that particular individual user's inhalation and exhalation phases, to control the adsorption and desorption phases 211, 241 of the pulsed PSA process in sync with the breathing cycle 202 of that particular individual user over time, e.g., over a plurality of inhalation and exhalation phases.

A. 4-Phase Pulsed PSA Cycle

The following describes the four phases 211, 221, 231, 241 of the PSA cycle performed by the example PSA system 300 illustrated in FIG. 3A. Each of the four phases 211, 221, 231, 241 is respectively illustrated in each of the FIGS. 3B, 3C, 3D, 3E. The PSA cycle or process executed by the phases 211, 221, 231, 241 illustrated in FIGS. 3A-3E is referred to herein as a 4-Phase Pulsed PSA Cycle. The oxygen concentrator including the PSA system 300 can include a controller 380 and an oxygen delivery device 342 in communication with the controller 380, as illustrated for example, in FIGS. 3G and 3H, where in FIGS. 3A-3E the controller 380 and the oxygen delivery device 342 have been removed for illustrative purposes only. In one example, the PSA system 302 includes an air filter 312 connected to the compressor 310 to filter out particles other than atmospheric air from the atmosphere to the compressor 310.

The example described herein is non-limiting, as PSA systems can however have a different number of steps or phases depending on the configuration.

1. Adsorption

Referring to FIGS. 1E and 3B, FIG. 3B shows the device of FIG. 3A in the adsorption phase 211. The controller 380 can enter the adsorption phase 211 either at the beginning of the inhalation phase, slightly before, or slightly after the beginning of inhalation phase of the user's breathing cycle 202, depending on the control schema and/or algorithm used to control operation of the oxygen concentrator including the PSA system 300. During the adsorption phase 211, valve 360 is set to connect the output of compressor 310 to the inlet of adsorption column 320. Valve 370 is closed. At this point, the compressor receives atmospheric air and pressurizes the atmospheric air to create pressurized air 236 and outputs the pressurized air 236 through the valve 360 to the inlet of adsorption column 320. As this pressurized air 236 flows and diffuses through the adsorption column 320, the nitrogen in the pressurized air 236 is adsorbed, and the oxygen product gas 216 is released at the outlet. In one example, the pressurized air 236 is greater than 1 atmospheric pressure. The adsorption column 320 contains zeolite which adsorbs the nitrogen from the pressurized air 236.

At this point, valve 370 is closed in an "off" position. Valve 350 is open in an "on" position. The oxygen enriched gas 216, absent most of the nitrogen, flows from the adsorption column 320, through valve 350, to the oxygen purge tank 330, resulting in a pressure drop across the adsorption column 320. Pressure in oxygen purge tank 330 is only slightly higher than atmospheric pressure during this phase. Valve 340 is also set to open such that concentrated oxygen gas 216 flows from the oxygen purge tank 330 to the user.

2. Oxygen Purge

Referring to FIGS. 1E and 3C, FIG. 3C shows the device of FIG. 3A in the oxygen purge phase 221. The controller 380 actuates the PSA system 300 to enter this phase at during the dead zone of the inhalation phase, as detected by input received from sensors 16, 18 and/or as determined by one or more algorithms execute by the controller 380. Valve 360 remains set to connect the output of compressor 310 to the inlet of adsorption column 320. Valve 370 remains closed and valve 350 remains open. Valve 340 is now switched to closed in an "off" position, preventing flow of enriched oxygen 216 from the oxygen purge tank 330 to the user. As concentrated oxygen flows from adsorption column 320 into oxygen purge tank 330, pressure in oxygen purge tank 330 increases, although it remains less than the pressure of atmospheric air entering adsorption column 320.

3. Pressure Equalization

Referring to FIGS. 1E and 3D, FIG. 3D shows the device of FIG. 3A in the pressure equalization phase 231. Valve 360 is set to direct the pressurized air from 236 compressor 310 to an air release, such that no more pressurized atmospheric air is being supplied into the adsorption column 320. The inlet of adsorption column 320 is blocked by both valve 360 and valve 370. Valve 350 is closed blocking flow between adsorption column 320 and oxygen purge tank 330. During this phase, the pressure differential across adsorption column 320 dissipates such that the air pressure over the entire adsorption bed in the adsorption column 320 settles at an intermediate value. In the pressure equalization phase 231, adsorption is minimal and/or ceases, such that neither oxygen enriched gas 216 is produced from the pressurized atmospheric air 236 nor is enriched oxygen 216 outputted from the PSA system 300 to the user.

4. Desorption (Nitrogen Release)

Referring to FIGS. 1E and 3E, FIG. 3E shows the device of FIG. 3A in the desorption phase 241. The controller 380 actuates the PSA system 300 to enters this desorption phase 341 during the exhalation phase of the user's breathing cycle 202, at a time determined by the controller 380 based on data received from sensors 16, 18 and/or as determined by the controller 380 and/or one or more algorithms executed by the controller 380. Valve 340 remains closed. Valve 360 remains in the same position as the pressure equalization phase. Valves 350 and 370 are opened in an "on" position allowing flow. Valve 340 remains closed in an "off" position since during exhalation, the user does not need oxygen. During this phase, the pressure gradient through adsorption column 320 reverses, such that the outlet is at higher pressure than at the inlet of the adsorption column 320. As the pressure in adsorption column 320 decreases, nitrogen is desorbed from the adsorption bed, e.g., nitrogen re-enters the gaseous state in the adsorption column 320. The pressure gradient causes the gaseous nitrogen to flow out the inlet of the adsorption column 320, through valve 370, such that the desorbed gaseous nitrogen is released via valve 370 back into the atmosphere. A portion of the concentrated oxygen 216 flows from oxygen purge tank 330 back into adsorption column 320 to balance the nitrogen gas exiting via the valve 370. When the controller 380 senses that the exhalation phase is almost over, it actuates the PSA system 300 return to the adsorption phase 211 of FIG. 3B and the PSA cycle repeats.

B. PPSA with 3-Way Valve and Nitrogen Release Combined

Another example configuration of a PSA system 300 is illustrated by the pulsed PSA (PPSA) system 301 shown in FIG. 3F. The oxygen concentrator including the PSA system 301 can include a controller 380 and an oxygen delivery device 342 in communication with the controller 380, as illustrated for example, in FIGS. 3G and 3H, where in FIG. 3F the controller 380 and the oxygen delivery device 342 have been removed for illustrative purposes only. In this example, a compressor 310 draws in atmospheric air and compresses it, in one example, to a pressure of about 2-4 atmospheres. In some embodiments this pressure output could be lower than 2 atmospheres or higher than 4 atmospheres. The temperature can also increase due to adiabatic compression. In some examples, the compressor 310 can include some storage volume and/or a heat exchanger. In one example, the air can be cooled after leaving the compressor 310 in order to increase the adiabatic efficiency of the adsorption phase 211. In another example, this pressure swing adsorption process can be thermally assisted wherein during the adsorption phase 211 the adsorption column 320 is cooled during the adsorption phase 211 and heated during the desorption phase 241. In another example, the oxygen purge gas 216 in the oxygen purge tank 330 can be heated in order to increase the adiabatic efficiency of the desorption phase 241. In the example shown in in FIG. 3F, valve 372 can be a three-way solenoid valve. In one configuration, for example, the "ON" configuration, valve 372 connects the output from the compressor 310 to an inlet of adsorption column 320 while blocking flow to the nitrogen release. In another configuration, valve 372 connects the inlet of the adsorption column 320 to the nitrogen release while blocking flow from the compressor 310. An outlet of the adsorption column 320 is connected to an inlet of the oxygen purge tank 330. The adsorption column 320 contains a selectively adsorbent material, such as zeolite, as previously described herein. The oxygen purge tank 330 provides a volume for storage of concentrated oxygen gas 216. The controller 380 changes the state of valves 372, 340, and 350 to switch the system among the several phases of the PSA cycle as described herein. In one example, the controller 380 is in communication with and receives at least one input from an oxygen delivery device 342 that measures the breathing pattern characteristics of a user using an oxygen concentrator including the PSA system 301, to actuate the PSA system 301 in response to phases of the user's breathing cycle 202 detected by and/or estimated by the controller 380 using the input received from the oxygen delivery device 342. In one example, the oxygen delivery device 342 includes one or more sensors 16, 18 (see FIG. 1M) to sense parameters such as flowrate and/or air pressure of the user's breathing, and to output data to the controller 380 related to these parameters. The oxygen delivery device 342 may include sensor or other measurement devices such as mass air flow sensor(s), pressure transducer(s), oxygen concentration sensor(s), and/or carbon dioxide concentration sensor(s), which may provide data to the controller 380 for use in conjunction with one or more algorithms to determine and/or estimate the exhalation and inhalation phases of the user's breathing cycle 202. The controller 380 synchronizes the PSA phases 211, 241 of operation of the PSA system 301 with the user's breathing cycle 202 such that oxygen enriched gas 216 is produced by and/or outputted from the PSA system 301 during the useful portion of each inhalation phase and during the pre-inhalation period of each exhalation phase of the individual user's breathing cycle 202. In one example, the controller 380 synchronization between the different sensor or data outputs could be performed using a synchronization algorithm, comprising one or more control methods such as time-based control, pressure-based control, and/or gas composition-based control. In one example, delivery of the oxygen gas 216 is initiated near the end of each user exhalation phase, e.g., during a pre-inhalation period of the exhalation phase, to allow oxygen pooling at the beginning of each user inhalation phase, improving user oxygenation.

In one example, the compressor 310 in the PSA system 302 does not have to receive and compress air constantly. The compressor 310 can be variably controlled by the controller 380 such that the compressor 310 can be in an "ON" or "OFF" state where only the adsorption and oxygen purge phases 211, 221 will allow the compressor 310 to deliver pressurized air 236 to the adsorption column 320. This way, instead of the compressor 310 always providing pressurized air 236 and having a valve to direct air into or away from the adsorption column 320 depending on the phase of the PSA system 300, the compressor 310 can provide air by turning on or off. In one example, the controller 380 includes a pulse width modulation (PWM) control that controls the power of the compressor 310. In another example, the controller 380 can include at least one MOSFET switch (see 812 in FIG. 8) to regulate the power of the compressor 310 by turning it on or off. Powering the compressor 310 on and off also dissipates heat more effectively from the PSA system 301. In one example, an air pressure tank 332 (see FIG. 3H, for example) can be combined with a pressure switch in order to turn off the compressor once the pressure inside the air pressure tank 332 reaches a certain pressure value. In one example, a brushless DC electric motor is used to power the air compressor 310, wherein higher intermittent loading allows for a more compact PSA system 10 as compared to continuously loaded/operated motors used in prior art PSA systems. Further, DC motor control can be used to regulate and dynamically adjust air compressor flowrate and pressure, allowing for changes in oxygen output 216 from the PSA system 10 on a breath by breath basis, e.g., adjustments to the oxygen output 216 can be made for every exhalation/inhalation phase pair of the user's breathing cycle 202 such that the oxygen concentrator dynamically responds to changes and/or irregularities in the individual user's breathing pattern. This DC motor control could also be used in conjunction with proportional valve control and a surge tank, wherein oxygen accumulates in the surge tank and is produced by a pulsed PSA system 10 that utilizes one or more adsorbent columns 320, wherein the PSA cycle times of the pulsed PSA system 10 in the present invention are not the same as user breathing and/or could be constant values.

During operation of the PSA system 301 shown in FIG. 3F, at the adsorption phase 211, similar to that of the adsorption phase 211 of the PSA system 300 shown in FIG. 3B, the controller 380 of the PSA system 301 actuates the beginning of the adsorption phase 211 at the beginning of the user's inhalation phase or slightly before the beginning of the user's inhalation phase, e.g., toward the end of the user's exhalation phase. During the adsorption phase 211, valve 372 is set to connect the output of compressor 310 to the inlet of adsorption column 320. As the compressed air flows into the adsorption column 320, nitrogen in the compressed air is adsorbed into the zeolite of the adsorption bed, increasing the relative oxygen content of the compressed air in the adsorbent column 320. The air, absent most of the nitrogen, flows from the adsorption column 320 to oxygen purge tank 330 through valve 350 at an "on" configuration, with a resultant pressure drop across the adsorption column 320. In one example, the pressure drop is lower than the pressure provided from the compressor 310 and hence oxygen enriched product 216 flows out from the adsorbent column 320. Pressure in the oxygen purge tank 330 is only slightly higher than atmospheric pressure during this phase. Valve 340 is at an "on" configuration such that concentrated oxygen 216 flows from oxygen purge tank 330 to the user.

At the oxygen purge phase 221, similar to that of the oxygen purge phase 221 of FIG. 3C, the controller 380 of FIG. 3F initiates actuation of the oxygen purge phase 221 at the during the dead zone of the inhalation phase of the user's breathing phase 221. Valve 372 remains set to connect the output of compressor 310 to the inlet of adsorption column 320. Valve 340 is closed, preventing the flow of oxygen gas from the oxygen purge tank 330 to the user. As concentrated oxygen flows from adsorption column 320 into oxygen purge tank 330, pressure in oxygen purge tank 330 increases, although it remains less than the pressure of air entering adsorption column 320.

During operation of the desorption phase 241 of the PSA system 301, similar to that of desorption phase 241 of PSA system 300, the controller 380 of PSA system 301 actuates the PSA system 301 to enter the desorption phase 241 during the user's exhalation phase as detected and/or determined by the controller 380. During the desorption phase 241, the valve 340 remains closed. Valve 372 is switched to connect the inlet of adsorption column 320 to a nitrogen release. During the desorption phase 241, the pressure gradient through the adsorption column 320 reverses such that the pressure at the outlet is at higher pressure than at the pressure at the inlet. As the pressure in adsorption column 320 decreases, nitrogen desorbs from the adsorption bed, e.g., is released in a gaseous form from the adsorption bed and into the adsorption column 320. The pressure gradient causes the nitrogen to flow out the inlet of the adsorption column 320, through valve 372, to the nitrogen release. During release of the nitrogen gas, some concentrated oxygen flows from oxygen purge tank 330 back into adsorption column 320. When the controller 380 senses that the user's exhalation phase is almost over, it returns operation of the PSA system 301 to the adsorption phase 211 and the PSA cycle repeats.

C. PPSA with Oxygen Delivery Device with Pressure Sensor

In another example configuration of the PSA system 300, a pulsed PSA (PPSA) system 302 is shown in FIG. 3G and includes an oxygen delivery device 342 in communication with the controller 380. The oxygen delivery device 342 is connected to the oxygen purge tank 330 through the valve 340 such that the oxygen delivery device 342 is the physical interface that delivers the enriched oxygen 216 from the oxygen purge tank 330 to the user. In one example, the oxygen delivery device 342 comprises a cannula and/or airline 12 (see FIG. 1M) that can engage the user for delivery of the oxygen enriched gas 216 to the user's respiratory system, for example, via the nasal passages of the user. In one example, the oxygen delivery device 342 comprises at least one pressure sensor 16 (see FIG. 1M) that can sense and detect the beginning of each inhalation phase and the beginning of each exhalation phase of the breathing cycle 202 of a user of an oxygen concentrator including the PSA system 302 and oxygen delivery device 342. In some examples, the oxygen delivery device 342 can include one or more user breathing cycle sensors 18, as described related to FIG. 1M, which can be in communication with the controller 380, such that the controller 380 receives data from the pressure and breathing cycle sensors 16, 18 and can utilize the received data to dynamically determine and/or estimate the exhalation and inhalation phases of the user's breathing cycle 202 in real time, and to dynamically synchronize the PSA valve actuation sequences that control the adsorption, oxygen purge, pressure equalization, and desorption phases 211, 221, 231, 241 of the PSA cycle with that the breathing cycle 202 of the user in real time. In one example, the oxygen delivery device 342 measures flowrate or air pressure of the user's breathing, for example, using sensors 18. The controller 380 synchronizes actuation and/or duration of each of the 211, 221, 231, 241 phases of the PSA system 302 with the user's breathing such that oxygen enriched gas 216 is produced and/or outputted to the user during the physiologically useful portions of respiration, e.g., during the useful period of the user's inhalation phase prior to the anatomical dead space period, and during the pre-inhalation period of the user's exhalation phase.

In one example, the controller 380 can be configured to include a default setting for the oxygen flow cycle. The default setting can be set, for example, at 15 breaths per minute when the PSA system 10 is initially turned on, e.g., powered up by a user of the oxygen concentrator. The controller 380 can be configured to actuate the PSA system 10 to start the adsorption phase 211 only when the breathing pressure sensor 16 reaches a defined threshold indicating a point in time within an inhalation phase and/or exhalation phase of the breathing cycle 202 of the user. In one example, the pressure threshold can be based on a negative threshold pressure, such as −0.06 centimeter of water (cmH2O). The controller 380, for subsequent breaths, e.g., for inhalation and exhalation phases succeeding the user's initial breaths, can use the data collection from the breathing pressure sensor 16 during the initial breaths to change the oxygen flow cycle of the oxygen concentrator for each succeeding breath, which can include changing one or more of the oxygen production volume, the oxygen flowrate, and the time at which oxygen output 216 is initiated for each succeeding breathing phase, depending on the breathing pattern of the user sensed by pressure sensor 16. Alternatively, the controller 380 can also configure the PSA system 300 to not deliver oxygen when the breathing pressure sensor 16 detects and/or the controller 380 determines that the user is not breathing in air or there are other failed triggers that do not justify outputting the enriched oxygen gas 216 from the PSA system 300. The default setting for a particular user can also change based on the user's specific breathing pattern using control algorithms including but not limited to one or a combination of multi-predictive, PI, PID, feedback, and/or feedforward controls which may be stored in and executed by the controller 380.

In one embodiment, the compressor 310 can be operated intermittently in order to reduce energy consumption when not utilized during the adsorption phase for a pulsed pressure swing adsorption system 303. In one embodiment, this is accomplished using a MOSFET switch 812 to turn the air compressor 310 ON or OFF. Ina different embodiment, wherein the compressor 310 utilizes an electric motor, pulsed width modulation (PWM) control could be utilized and synchronized with the adsorption, oxygen purge, and desorption steps of the pulsed PSA cycle. In one embodiment, a pressure switch can be used in conjunction with an air pressure tank 332 to turn off the compressor. Further, when operated intermittently (for example, 1 second ON, 3 seconds OFF, etc.) as compared to continuously, the air compressor or diaphragm pump can more effectively dissipate heat from the PSA system 10. This increases thermodynamic efficiency and allows the electric motor to utilize higher voltages or loading when powered on, without causing overheating. In this example, higher air flowrates and pressure outputs can be obtained from a relatively smaller compressor 310, with the advantage of a decreased packaging space requirements for the smaller compressor 310, and an associated decrease in the size of the PSA system 10.

D. PPSA with $2^{nd}$ Air Pressure Tank after Compressor

In an alternate example of the PSA system 300, a PSA system 303 is shown in FIG. 3H which includes the addition of an air pressure tank 332. The PSA system 303 can include a controller, such as the controller 380 illustrated in FIGS. 3A-G, where the controller 380 is not shown in FIG. 3H for illustrative purposes only. In this example, pressurized air 236 that is not used during the desorption phase 241 can be stored and utilized when the pulsed PSA system 303 switches to the adsorption phase 211 and/or to the oxygen purge phase 221. This configuration is contrasted with that of PSA system 300 of FIG. 3A. In this example, a two-way valve 390 is provided instead of the three-way valve 360 included in PSA system 300, which releases the pressurized air 236 back into the atmosphere. In the example shown in FIG. 3H, the air pressure tank 332 can be utilized as an energy storage device, where pressurized air 236 is stored for periods of higher than normal oxygen demand and released to the adsorption column 320 to produce larger volumes of oxygen enriched gas 216 during the higher demand inhalation phases. Alternatively, the air pressure tank 332 can be utilized as an energy storage device at specific times during the inhalation phase, such as during the useful period, e.g., the productive portion, of the inhalation phase. In one example, the PSA system 303 can include an additional valve (not shown) in which waste air from a continuous flow air compressor can be output.

E. PPSA without 2-Way Valve Between Oxygen Purge Tank and Adsorption Column

In an alternate example of the PSA system 300, a PSA system 304 is illustrated in FIG. 3I and described herein. The oxygen concentrator including the PSA system 304 can include one or more breathing cycle sensors 16, 18 and/or an oxygen delivery device 342 in communication with the controller 380, as illustrated for example, in FIGS. 3G and 3H, where in FIG. 3I the oxygen delivery device 342 has been removed for illustrative purposes only. Similar to the PSA system 300 shown in FIG. 3A, the PSA system 304 of FIG. 3I does not include a two-way valve between the adsorption column 320 and oxygen purge tank 330. The PSA system 304 comprises a compressor 310, an adsorption column 320, and an oxygen purge tank 330. The compressor 310, adsorption column 320, and oxygen purge tank 330 can be connected to each other in series, as shown in FIG. 3I. A plurality of valves such as valve 340, valve 360, and valve 370 operably connect each of the compressor 310, the adsorption column 320, and the oxygen purge tank 330 and act as gates for either allowing or blocking gas to flow through each of the valves, where the valves 340, 360, 370 can be selectively actuated by the controller 380 to operate the PSA system 304 in the various PSA phases, as described in detail herein. The controller 380 is configured to monitor and control the amount, direction, and timing of the flow of the gases into and out from the PSA system 304 by controlling the valves 340, 360, and 370. In one example, the valves 340, and 370 are two-way solenoid valves and valve 360 is a 3-way solenoid valve. The three-way valve 360, when actuated in a first position, e.g., in a first valve state, connects the output of the compressor 310 to an inlet of the adsorption column 320 while blocking flow to an air release which when open, e.g., unblocked, vents to the atmosphere. In a second position, e.g., in a second valve state, the valve 360 connects the outlet of the compressor to the air release while blocking flow to the adsorption column 320. Valve 370 can be a normally-closed two-way solenoid valve which selectively connects the inlet of the adsorption column 320 (or, alternatively, a separate port) to the nitrogen release. Oxygen purge tank 330 provides a volume for storage of concentrated and/or enriched oxygen gas 216. Valve 340 can be a normally-closed two-way solenoid valve which selectively connects an outlet of the oxygen purge tank 330 to a release such that a user can breathe in the oxygen enriched gas 216 from the oxygen purge tank 330 when the valve 340 is released, e.g., in an open position. In one example, the controller 380 can control and change the state of valves 340, 360, and 370 to switch the system among the several PSA phases, as described herein. The controller 380 uses one or more algorithms to synchronize each PSA phase of operation of the PSA system 304 with the each breathing phase of the user's breathing cycle, e.g., with each breath taken by the user, to control the operation of the PSA system 304 such that oxygen enriched gas 216 is outputted during the productive portion of the inhalation phase and/or during the productive portion of the exhalation phase of each user breath, and such that the output of oxygen enriched gas 216 is minimized or ceased during the non-productive portions of the user's breathing cycle 202, such as during the anatomical dead space period of the inhalation phase and during the non-useful period of the exhalation phase of each breath of the user's breathing cycle 202. The productive portion of the user's inhalation phase can also be referred to herein as the useful period of the inhalation phase. The exhalation phase of the user's breathing cycle 202 can be characterized as including a non-useful period followed by a pre-inhalation period, where in an illustrative example shown in FIG. 1F the pre-inhalation period occurs between the non-useful period and a succeeding inhalation phase of the user's breathing cycle 202.

In this example, the PSA System 304 of FIG. 3I differs from that of PSA system 300 such that the PSA system 304 does not include a two-way valve (see valve 350 in PSA system 300) between the adsorption column 320 and oxygen purge tank 330. Effectively, the steps of the PSA system 304 are similar to that of the 4-Phase Pulsed PSA cycle but instead do not include the pressure equalization phase 231. The functions of the pressure equalization phase 231 are, in the example PSA system 304 shown in FIG. 3I, combined with that of the oxygen purge phase 221. In one example, the PSA cycle of the PSA system 304 is consistent with that of FIG. 1G. Effectively, the configuration of the Pulsed PSA system 304 can be applied to that of any of the other PSA systems 10.

F. Vacuum PPSA

FIGS. 3J, 3K, and 3L illustrate an alternate examples of a single bed oxygen concentrator, including, respectively, a vacuum pulsed PSA (PPSA) system 305, 306, 307. The PSA systems 305, 306, 307 each include a controller 380, as illustrated for example, in FIGS. 3A-G, where in FIGS. 3J, 3K, and 3L the controller 380 has been removed for illustrative purposes only. The oxygen concentrators including the PSA systems 305, 306, 307 can each include one or more breathing cycle sensors 16, 18 and/or an oxygen delivery device 342 in communication with the controller 380, as illustrated for example, in FIGS. 3G and 3H, where in FIGS. 3J, 3K, and 3L the oxygen delivery device 342 has been removed for illustrative purposes only. As illustrated in FIG. 3J, a single bed oxygen concentrator is shown including a PSA system 305 which includes both a compressor 310 and a vacuum compressor 312. In the example shown, valve 372 is a three-way solenoid valve. In one valve state of the valve 372, the valve configuration, for example, the "ON" state, the valve 372 connects the outlet of the compressor 310 to an inlet of the adsorption column 320 while blocking flow to the nitrogen release, e.g., where the nitrogen release can occur via the outlet from the compressor 310 when the state of the valve 372 is changed. In another configuration, valve 372 connects the inlet of adsorption column 320 to the nitrogen release while blocking flow of pressurized atmospheric air, for example, from the vacuum compressor 312 and the compressor 310, into the adsorption column 320. In one example, other components, including at least one cooling fan, can be included in the PSA system 10, including the present example PSA system 305, to cool components of the PSA system 10.

One advantage of the Vacuum Pressure Swing Adsorption (VPSA) system shown in FIGS. 3J, 3K, and 3L, is the fact that VPSA allows for a longer adsorbent column lifecycle and higher adsorbent productivity since adsorbed products are more easily removed using vacuum depressurization as compare with removal of adsorbed products using an oxygen gas purge phase 221. Further, VPSA, in some examples, yields oxygen enriched gas 216 which is characterized by a higher O2 purity than oxygen enriched gas 216 produced from a non-VPSA system 10.

At the adsorption phase 211, similar to that of adsorption phase 211 of the PSA system 300 shown in FIG. 3B, the controller 380 actuates the VPSA system 305 to initiate the adsorption phase 211 at the beginning of the inhalation phase or at a pre-inhalation period of the exhalation phase occurring slightly before the beginning of the inhalation phase. During the adsorption phase 211, valve 372 of the VPSA system 305 connects the output of the compressor 310 to the inlet of adsorption column 320, such that pressurized air 236 flows from the compressor 310 over the adsorption bed of the adsorption column 320, where nitrogen in the compressed air 236 is adsorbed into the zeolite, and the oxygen enriched air 216, absent most of the nitrogen, flows from the adsorption column 320 to oxygen purge tank 330, with a resultant pressure drop occurring across the adsorption column 320. The air pressure at the outlet of adsorption column 320 is only slightly higher than atmospheric pressure during this adsorption phase 211. During the adsorption phase 211, valve 340 is set to open such that the concentrated oxygen gas 216 flows to, e.g., is outputted to, the user, for example, via a cannula 12 (not shown) connected to the output of the valve 340 and VPSA system 305.

When operating in a desorption phase 241, similar to that of desorption phase 241 of FIG. 3E, the controller 380 actuates the VPSA system 305 to enter the desorption phase 241 during the beginning of the exhalation phase of the user's breathing cycle. During the desorption phase, each of the valves 340 and 350 are in the "OFF" configuration, or closed state, and valve 372 is in an open state to connect the inlet of adsorption column 320 to the inlet of the vacuum compressor 312. The vacuum compressor 312 is actuated such that, during the desorption phase 241, the pressure gradient through adsorption column 320 reverses such that the air pressure at the outlet of the adsorption column 320 is at higher pressure than the air pressure at the inlet of the adsorption column 320. Due to the sub-atmospheric pressures created by the operation of the vacuum pump 312, an oxygen purge stage 221 is not needed to remove the adsorbed nitrogen from the adsorbent column 320. Rather, as the pressure in adsorption column 320 decreases, nitrogen desorbs from the adsorbent bed into a gaseous state in the adsorption column 320 and the desorbed nitrogen gas is released via an exhaust outlet 317 of the vacuum compressor 312 back into the atmosphere. The pressure gradient created by the vacuum compressor 312 causes the nitrogen gas to flow out the inlet of the adsorption column 320, through valve 372 and vacuum compressor 312, to the nitrogen release outlet. In some embodiments, the controller 380 actuates valve 350 to an opened state, to release a volume or flowrate of concentrated oxygen from the oxygen purge tank 330, which flows back into desorbed adsorption column 320. When the controller 380 determines, for example, using data received from one or more sensors 14, 16, that the exhalation phase of the user is almost over, e.g., is approaching a pre-inhalation period in the exhalation phase, the controller 380 actuates the VPSA system 305 to return to the adsorption phase 211, and repeats the PSA cycle.

FIG. 3K illustrates another example PSA system 306 which utilizes a vacuum during the desorption phase 241, such that the PSA system 306 can be described as a VPSA system 306. In the example shown in FIG. 3K, the VPSA system 306 includes a combined vacuum pump and compressor 314, also referred to herein as a dual compressor 314, instead of a separate compressor 310 and vacuum compressor 312. By using a dual compressor 314, less packaging space is required within the oxygen concentrator, such that this configuration is advantaged by a more compact design which may be more convenient and portable for a user. In the example shown, valve 373 connects the dual compressor 314 and the adsorption column 320. In one example, the valve 373 is configured as a two-way valve, where in a first valve state, for example, an "ON" configuration, valve 373 connects an outlet of the dual compressor 314 output to an inlet of adsorption column 320 while blocking flow to a nitrogen release outlet. The dual compressor 314 is selectively actuable by the controller 380 to operate in one of a compressor mode and a vacuum mode, where in the compressor mode the dual compressor 314 operates to input pressurized air 236 from the atmosphere into the adsorption column 320, and in a vacuum mode operates to extract gas from the inlet of the adsorption column 320 and to pump the extracted gas toward the nitrogen outlet, creating a volume of air having substantially lower pressure than the atmospheric pressure of the air at the inlet. During operation of the VPSA system 306, the controller 380, in response to data inputs received from an oxygen delivery device 342 and/or sensors 16, 18 measuring flowrate or air pressure of the user's breathing cycle, synchronizes actuation of the PSA phases of operation with the user's breathing cycle such that enriched oxygen gas 216 is produced by the VPSA system 306 and collected in the oxygen purge tank 330, and is released, e.g., outputted, to the user during the productive portion of the user's breathing cycle. As previously described herein, the controller 380 dynamically controls the VPSA system 306 such that each PSA cycle is synchronized to each breath (exhalation/inhalation phase pair) of the user, and such that the actuation timing, PSA phase duration, flowrate, volume and/or timing of output gas released to the user can be varied from one PSA cycle to the next, in response to variation in one user breath to the next, as sensed or otherwise determined by the controller 380.

FIG. 3L illustrates an example PSA system 306 which is advantaged by being configured such that the VPSA system 306 includes the continuous operation of one single compressor 316 with no surge tanks, while generating intermittent raffinate product, wherein the raffinate product is an oxygen rich gas 216. During the desorption phase 241 when no raffinate product is being produced, pressurized air supply 236 being output from the continuous air compressor 316 is routed to a venturi vacuum generator 318 in order to utilize the pressurized air supply 236 as a vacuum source, without requiring a separate vacuum pump. This venturi vacuum generator 318 relies on the movement of the pressurized air 236 into a constricting nozzle. This movement creates an area of low pressure at the expanding side of the nozzle, also known as the vacuum chamber connection, which pulls nitrogen gas molecules into the flow during desorption from the vacuum chamber connection, allowing the nitrogen to be exhausted into the atmosphere. This venturi vacuum generator 318, which may also be referred to herein as a venturi vacuum chamber 318, may be single stage or multi-stage, and could be utilized to generate extremely low vacuum pressures. Most molecular sieves for air separation applications such as Lithium X-type zeolite have Type II isotherms, such that, by creating an extremely low vacuum pressure during the desorption step 241, a larger portion of the nitrogen adsorption isotherm can be utilized, improving the productivity per gram of adsorbent material and increasing the energy efficiency of the PSA system 10. In one example, the venturi vacuum generator 318 is a dual-headed diaphragm pump. In one example, other components, including at least one cooling fan, can be included in a PSA system 10 such as the PSA system 307, to cool components of the PSA system 10.

Referring to the example shown in FIG. 3L, for the adsorption phase 211 and similar to that of adsorption phase 211 of the PSA system 300 shown in FIG. 3B, the controller 380 actuates the adsorption phase 211 of the PSA system 307 at the beginning of the inhalation phase and/or at the beginning of a pre-inhalation period of the exhalation phase preceding the onset of the inhalation phase, where in one example, the controller 380 detects and/or determines the inhalation phase and/or the exhalation phase of the user's breathing cycle using inputs received from one or more breathing sensors 16, 18. During the adsorption phase 211, valve 364 is actuated to connect the output of the continuous compressor 316 to the inlet of adsorption column 320 such that compressed air 236 is flowed into the adsorption column 320, where nitrogen in the compressed air 236 is adsorbed into the zeolite material included in the adsorption bed. The oxygen enriched gas 216, absent most of the nitrogen, flows from the adsorption column 320 to oxygen purge tank 330, resulting in a pressure drop across the adsorption column 320. As such, the air pressure at the outlet of adsorption column 320 is higher than atmospheric pressure during this adsorption phase 211. During the adsorption phase 211, valve 340 is set to an open position, such that concentrated oxygen gas 216 flows to the user during the productive portion of the user's breathing cycle 202.

For the desorption phase 241, and similar to that of desorption phase 241 of the PSA system 300 illustrated in FIG. 3E, the controller 380 actuates the PSA system 307 to enter the desorption phase 241 during the non-productive portion of the user's breathing cycle, for example, at the beginning of the exhalation phase of the user's breath, as detected and/or determined by the controller 380 on a breath by breath basis. During the desorption phase 241, valves 340 and 364 are each in the "OFF" configuration. In one example, only valve 340 is configured in the "OFF" configuration. Valve 374 connects the inlet of adsorption column 320 to the inlet of venturi vacuum generator 318. During the desorption phase 241, the pressure gradient through adsorption column 320 reverses such that the outlet is at higher pressure than at the inlet. Due to the sub-atmospheric pressures created by the vacuum generator 318, an oxygen purge stage is not needed to remove nitrogen from the adsorbent column 320. As the pressure in adsorption column 320 decreases, nitrogen desorbs from the adsorbent material in the adsorption column 320, into a gaseous state. The pressure gradient causes the gaseous desorbed nitrogen to flow out the inlet of the adsorption column 320, through valve 374 and the venturi vacuum generator 318, to the nitrogen release outlet, to be exhausted from the PSA system 307. When the controller 380 senses that the exhalation phase of the user's breathing cycle 202 is almost completed, the controller 380 returns operation of the PSA system 307 to the adsorption phase 211 and the cycle repeats.

V. Method

FIG. 4 shows an example illustration of a method 400 for controlling an oxygen concentrator including a PSA system 10, as described herein and illustrated by the figures, to output enriched oxygen gas 216 from the oxygen concentrator to a user, where outputting of the enriched oxygen gas 216 is synchronized, on a breath by breath basis, with the individual user's breathing cycle 202. As previously described herein, the breathing cycle 202 of an individual user of an oxygen concentrator is comprised of a series of sequential breaths, such that each breath is preceded by a preceding breath and followed by a succeeding breath, and such that each breath includes an inhalation phase and an exhalation phase. The duration, breathing pressure pattern, oxygen flow rate and volume, carbon dioxide flow rate and volume, etc. can vary from one breath to another, such that a normal breathing cycle 202 includes variation from one breath to another. The method 400 described herein controls the operation of a PSA system 10 during each breath of a user using the oxygen concentrator including the PSA system 10, to synchronize, for each breath, the output of oxygen enriched gas 216 with the inhalation and exhalation phases of that breath. As such, each PSA cycle performed by the PSA system can vary from another PSA cycle, for example, in the duration of each PSA phase 211, 221,231, 241 of the PSA cycle, the volume and/or flowrate of the gases outputted from the PSA system to the user during the PSA cycle, which can include, in the various example configurations described herein, outputted enriched oxygen gas 216 and/or outputted pressurized air 236, etc., where it would be understood that variation of each PSA cycle from another PSA cycle is an essential feature of the control method 400 to enable synchronization of each PSA cycle with a corresponding breath of the user's breathing cycle 202.

Referring to the illustrative method 400 shown in FIG. 4, during steps 401 to 405 of the control method 400, the oxygen concentrator is in use by the user, e.g., a gas outlet of the PSA system 10 is in fluid communication with the user's respiratory system, for example, via a nasal cannula 12 connected to the gas outlet of the PSA system 10. As previously described herein, one or more breathing cycle sensors, which can include a breathing pressure sensor 16 and/or one or more breathing cycle sensors 18, are operatively connected to the cannula 12 to detect changes in at least one of the breathing cycle parameters sensed by the breathing cycle sensors 16, 18. The oxygen concentrator can include, in an illustrative example, an oxygen delivery device 342 which can include the breather cycle sensors 16, 18 and/or the cannula 12. The data is collected by the breathing cycle sensors 16, 18, also referred to herein as breathing cycle parameter data or breathing parameter data, is received by a controller 380 of the oxygen concentrator, and used by the controller 380, for example, in conjunction with one or more algorithms further described herein, to detect, predict, estimate and/or otherwise determine various breathing parameters during each breath of the user's breathing cycle, including, for example, the breathing pressure pattern of each breath, the time at which the inhalation phase of each breath begins and the exhalation phase of that breath ends, the volume and flow rate of gases inhaled and exhaled by the user during the breath, the O2 and CO2 concentration of the inhaled and exhaled gases, etc. In one example, parameter data is collected continuously by the sensors 16, 18, and the controller 380 is configured to continuously received the parameter data and to determine the breathing parameters in real time or near real time, such that the controller 380 can dynamically control the operation of the PSA system 10 to synchronize each PSA cycle performed by the PSA system 10 with the corresponding breath of the user in real time, and on a breath by breath basis. In one example, the controller 380 is configured to predict and/or estimate the breathing parameters for a succeeding breath, such that the controller 380 can control the operation of the PSA system 10 to synchronize the succeeding PSA cycle performed by the PSA system 10 with the user's succeeding breath, on a breath by breath basis. In this example, the controller 380 can receive additional data from the breathing cycle sensors 16, 18 and/or other sensors in the PSA system 10 which can be used by the controller 380 to increase the accuracy of the predicted and/or estimated breath parameters determined by the controller 380, for example, via a learning algorithm, feedforward control, or a combination of these.

At step 401, the controller 380 detects, predicts, and/or otherwise determines the beginning time of the next inhalation phase of a user's breathing cycle 202. In one example, the controller 380 may determine the ending time of the a current exhalation phase, which would determine the beginning time of the succeeding inhalation breath of the user.

At Step 402, an adsorption phase 211 of the PSA cycle for the PSA system 10 included in the oxygen concentrator is initiated at a time synchronized with the beginning of the user's inhalation phase determined at step 401. In one example, the PSA system 10 is actuated to begin the adsorption phase 211 and to output oxygen enriched gas 216 to the user at the beginning of the user's inhalation phase determined at step 401. In one example, the PSA system 10 is actuated to being the adsorption phase 211 and to output oxygen enriched gas 216 to the user at the end of the exhalation phase of the breath preceding the beginning of the inhalation phase determined at step 401, for example, the adsorption phase 211 is initiated at the beginning of a pre-inhalation period of the exhalation phase, as shown in FIG. 1D. In one example, the adsorption phase 211 is actuated by the controller 380, by actuating one or more valves and/or an air pressurizing device, such as a compressor 210, 310, 312, 316 included in the PSA system 10, to deliver pressurized, e.g., compressed air to an adsorption column 320 of the PSA system 10.

At Step 403, the adsorption cycle 211 is synchronized to the user's breath, to continue to produce oxygen enriched gas 216 at least through the productive portion of that breath. In one example, the adsorption cycle 211 continues until the beginning of an anatomical dead space period of the inhalation phase of the user's breath is detected. In one example, the adsorption cycle 211 continues until the beginning of the exhalation phase of the user's breath is detected. The adsorption cycle 211 is ceased at either the beginning of the anatomical dead space period or the beginning of the exhalation phase, as determined by the controller 380 for the specific configuration of PSA system 10 of the user's oxygen concentrator, such that minimal or no waste oxygen enriched gas is produced during the non-production portion of the user's breath, thus providing an advantage of increased operating efficiency of the PSA system 10.

At Step 404, concurrent with ceasing the operation of the adsorption cycle 211, and depending on the configuration of the PSA system 10 of the user's oxygen concentrator, the PSA system 10 initiates an oxygen purge phase 221 and/or a desorption phase 241, to remove adsorbed nitrogen from the adsorption column 320, where the desorbed nitrogen is evacuated as nitrogen gas from the PSA system 10, rejuvenating the adsorption column 320 in preparation for the next adsorption phase 211. The desorption phase 241 continues through the non-productive portion of the user's breath, which in one example includes at least the non-useful period of the exhalation phase, and can further include the dead space period of the inhalation phase. In one example, cessation of the desorption phase 241 is synchronized with the user's breath, via the controller 380, to occur at the beginning of the pre-inhalation period of the user's exhalation phase.

At Step 405, in some example PSA systems 10, during the time period from the cessation of the adsorption cycle 211 during the current breath of the user, and until the beginning of the adsorption cycle 211 synchronized to the succeeding breath of the user, the PSA system 10 can be actuated, for example, via the controller 380, to deliver pressurized air 236 to the user.

The method 400 is performed in a continuous loop, returning to step 401, where the controller 380 determines the breath parameters of the succeeding breath of the user, including, for example, the time at which inhalation of the succeeding breath will begin, and at step 402, synchronized with the succeeding breath of the user, actuates the PSA system 10 to perform the adsorption cycle 211 to provide oxygen enriched gas 216 to the user during the productive portion of the succeeding breath. In this manner, the steps 401-405 and method 400 is repeated for each successive breath of the user, using breathing parameters which are determined for each of the successive breaths by the controller 380, such that the PSA cycle can be dynamically varied for each breath as determined by the breathing parameters detected for that breath by the controller 380. As such, the method 400 is advantaged by synchronizing production and delivery of oxygen enriched gas 216 to the user on a breath by breath basis, such that the adsorption and desorption phases 211, 241 of each PSA cycle can be varied in sync with the variation detected in the particular user breath occurring during the PSA cycle, thereby providing oxygen enriched gas 216 only during the productive portion of each breath, and not providing, e.g., ceasing production of or conserving oxygen enriched gas 216 in the PSA system 10 during the non-productive portion of each breath, increasing the efficiency of the operation of the PSA system 10, and optimizing desorption of nitrogen from the adsorption column 320 during the PSA cycle associated with each breath.

VI. Control System

By way of illustration, a typical, e.g., average or expected, breath of a user includes an inhalation phase having a duration of around 2.0 seconds, which includes a useful period of around 1.5 seconds followed by an anatomical dead space period of around 0.5 seconds, and an exhalation phase having a duration of around 2.5 seconds, such that each breath of a user is around 4.5 seconds in total duration. As such, a typical, e.g., average or expected user breathing cycle 202 would be characterized by approximately 13 breaths per minute, corresponding to a user breathing rate of approximately 13 breaths per minute. However, because not all humans have the same breathing cycle 202, and exhibit variability in breathing rate resulting from variations in the duration of each breath and variation in the duration of each inhalation phase and exhalation phase of each breath, the PSA system 10 described herein provides the user with the advantage of PSA cycle times which are dynamically varied on a breath by breath basis, to synchronize oxygen gas output 216 to each breath of the individual user. Also, external conditions such as altitude, weather, temperature of the individual user's environment, or specific physical activity or physical condition of the user, may dynamically vary the oxygen requirements of the individual user, such that the PSA system 10 described herein would also benefit the individual user by dynamically varying the PSA cycle on a breath by breath basis, responsive to changes in the user's environment and/or changes in the user's oxygen requirements due to, for example, the user's then current physical condition and/or activity level, to synchronize the oxygen output 216 provided to the user during each PSA cycle to the user's then current oxygen requirements and breath parameters, in real time.

In one example, the PSA system 10 is provided comprising a controller 380 that can detect, monitor, and regulate each of the adsorption 211, oxygen purge 221, pressure equalization 231, and desorption 241 phases of each PSA cycle performed by the PSA system 10, in sync with the user's breath, even when the breathing parameters of that user's breath varies from a preceding breath and/or is irregular as compared with an average breath of that user's breathing cycle 202. The controller 380, in an illustrative example, can be configured as a microprocessor 814 (see FIG. 8) with a memory or a programmable logic control system that can regulate each PSA cycle and the oxygen output 216 delivered to the user from that PSA cycle, according to the real time breathing pattern of the user, such that the oxygen output 216 for each PSA cycle is matched with, e.g., synchronized to, the particular user breath occurring during the that PSA cycle, to dynamically response to changes and/or breath to breath variation in the user's breathing pattern. In one example, the microprocessor 814 and memory can collect data from the user's breathing patterns and predict the next breath and/or the breathing cycle 202 of the user, where the cumulative data can be used to increase the accuracy of the predictive algorithms used by the controller 380 overtime. The control system comprises a microprocessor-based control system or programmable logic control system 380 wherein oxygen output 216 and user breathing patterns are matched. In one example, a continuous flow of the enriched oxygen gas 216 is provided to the user only during the useful period of the inhalation phase of the user's breath, where the adsorption phase 211 is actuated by the PSA system 10 during the inhalation phase to provide the continuous flow oxygen gas, and the oxygen gas 216 is conserved during the anatomical dead space period of the inhalation phase and the exhalation phase, wherein during this conservation period the oxygen purge phase 221 and/or the desorption phase 241 of the PSA cycle is actuated.

One exemplary method of monitoring, regulating, and matching oxygen output 216 in real time with that of a user's individual breathing cycle 202 can include having pressure sensors configured within the PSA system 10 to measure and record each pressure swing period during the inhalation and exhalation phases of each user breath. The data obtained from the pressure swing period cycles can be aggregated and used to predict the average cycling time of a user's breathing cycle 202, e.g., the user's average breathing rate. In one example, the PSA system 10 can include a plurality of pressure sensors, each configured as a mass airflow meter (MAF), such that a pressure sensor can be located at each valve of the PSA system 10 to sense the pressure variation at the valve over time, to determine each pressure swing period during operation of the PSA system 10.

In one example, one or more pressure sensors are connected to the adsorption column 320 to determine the pressure delta caused by the change in pressure from the adsorption phase 211 of each PSA cycle to the desorption phase 241 of that PSA cycle. The data obtained from the pressure delta cycles can also be aggregated and used to predict and the average cycling time of a user's breathing cycle 202 based on the pressure delta.

In one example, at least one valve in the PSA system 10 can be a proportional control valve such that a tidal volume of a user requirement can be predicted based on feedback and data gathered about previous breaths from the user. In this example, the controller 380 of the PSA system 10 can control the orifice size of the oxygen output valve 340, 540, 640 to change the rate at which oxygen enriched gas 216 is output to the user. This proportional control valve can also be combined with a ON-OFF solenoid in order to vary output time the oxygen enriched gas 216 is delivered to the user during the adsorption phase 211.

In one example, to initiate performance of the adsorption phase 211 by the PSA system 10, the user's inhalation pressure can be detected by the controller 380 using inputs received from the breathing pressure sensor 16, and the PSA system 10 can be actuated by the controller 380 to start the adsorption phase 211 when the breathing pressure caused by the user's inhalation reaches a certain threshold or represents a certain mathematical pattern based on signal conditioning. The threshold does not necessarily need to a be a positive threshold value but could also be a negative pressure value (i.e., a value of −0.05 cm H2O pressure). To prevent false positives, the time derivative of the pressure versus time graph can also be calculated. In such case, if the time derivative valve is positive, such that when the inhalation pressure reaches a certain threshold pressure value close to zero, the adsorption phase 211 is actuated by the controller 380. The desorption phase 241 can be triggered by the controller 380 similarly, by detecting a certain pressure threshold associated with the beginning of a dead space period of the inhalation phase and/or associated with the beginning of the exhalation phase of the user's breath, which could be determined, for example, using an algorithm which calculates the time derivative of the breathing pressure versus time graph. Thus, each PSA cycle of the of the PSA system and the oxygen output flow from each PSA cycle can be different from a previous PSA cycle, where learning algorithms and the accumulated data collected during operation of the PSA cycle during preceding breaths can be used to predict the optimal PSA cycle times for the next PSA cycle, based on previous cycles. In one example, the data and feedback used by the controller 380 can be lag time, adsorption kinetics or valve hysteresis that cause time variations in syncing the PSA cycle and oxygen output 216 with each breath of the user and/or the user's breathing cycle 202.

In one example, the controller 380 can utilize the pressure sensors 16, 18 of the oxygen delivery device 342, for example, to detect the user's inhalation phase based on a negative trigger pressure threshold. For example, the threshold can be 0.6 cm H2O pressure. In one embodiment, unless more than the threshold amount of pressure difference is reached, the controller 380 will not trigger an adsorption 211 or desorption 241 phase to prevent accidental oxygen bursts or false positives, as such false positives could comprise a pneumatic oxygen delivery system or conserver. In another embodiment, no pressure thresholds are used, but rather time based control with error compensation is employed in the control strategy, configured as an electronic oxygen delivery system or conserver.

In another example, the rate and volume of enriched oxygen output 216 that leaves the oxygen purge tank 330 can be adjusted in real time by adjusting the power delivery to the compressor 310. The power adjustment can be controlled by the controller 380. In an alternate embodiment, valve 340 can be a variable and/or proportional control valve such that valve 340 can be adjusted to allow oxygen output 216 from the oxygen purge tank 330 at various flowrates.

In one example, the control system for regulating and executing the pressure swing adsorption cycles could mature, e.g., evolve and/or improve in predictive accuracy over time and with feedback on each breath of the user's breathing cycle 202. The feedback can be aggregated via the controller 380 to build a time derivative pressure curve defined by the cumulative preceding breaths of the user and measurements of the PSA cycles associated therewith. In one example, the control strategy developed using the feedback data can include the PSA system 10 controlling each PSA cycle to switch from the adsorption phase 211 to the oxygen purge phase 221 at a time when the derivative of the pressure curve reaches a certain negative value. In a non-limiting example, this negative value will be defined by the anatomical dead space period of the user's inhalation phase, where the negative value may correspond to the beginning time of the anatomical dead space period, or another time defined by the anatomical dead space period. Similarly, control strategy developed using the feedback data can include the PSA system 10 controlling each PSA cycle to trigger the desorption phase 241 when a time derivative of a pressure curve reaches a certain positive value. In one example, the certain positive value can be defined by the exhalation phase of the user's breath, where the certain positive value corresponds to the start of the exhalation period in one example, and to another time defined by the exhalation period in another example. The use of time derivative pressure curves can allow near instantaneous, e.g., near real time, cycle time adjustments for the cycle times of each phase 211, 221, 231, 241 of the PSA cycle. In some embodiments, feedforward control can be used to compensate for error in oxygen output and delivery over the course of a user's breathing cycle 202 consisting of a plurality of breaths.

Referring to the PSA system 303 shown in FIG. 3H, in an illustrative example, when this initial pressure value is reached, the adsorption phase 211 is actuated by opening valve 360 (two-way valve) to allow compressed air 236 to flow to the adsorbent column 320. During this adsorption phase 211 the nitrogen purge valve at the inlet, valve 370, is closed. In one embodiment, valves 360 and 370 may be combined into a three-way solenoid. During this adsorption phase 211, valves 340 and 350 are open. Valve 340 can be a proportional control exhaust valve such that a tidal volume of the user can be predicted, and oxygen output 216 can be precisely output to the oxygen delivery device 342 throughout the user's inhalation phase in, for example, a sinusoidal manner by utilizing the proportional control exhaust valve 340 such that the orifice size adjusts in order to change the rate at which oxygen is output to the user. This proportional control exhaust value could also be combined with an ON-OFF solenoid in order to vary different periods of the adsorption phase 211. In one example, the valve 340 can be replaced by a two-way solenoid valve in which oxygen can be output in a constant continuous flow manner during the user inhalation phase.

In the example, the control schema implements feedback control such that oxygen output volume can be precisely metered per breath by adjusting compressor 310 airflow output. Proportional-integral-derivative control (PID control) can also be used as a form of feedback control to reduce steady state error associated with precisely delivering oxygen during the useful period of the user inhalation phase and conserving oxygen during the anatomical dead space period of the inhalation phase and the exhalation phase. In one example, PID control of the orifice size of the valve is adjusted every 1-5 milliseconds using a stepper motor to actuate the proportional control exhaust valve 340. This feedback or PID control can have adjustment times shorter or longer than 1 millisecond depending on the sampling rate or frequency of the valve or sensors included in the control schema. This proportional control valve 340 outputs the oxygen linearly. The orifice size changes the rate at which the oxygen gas 216 is output causing the changing the slope of the line 206 as illustrated in FIGS. 1G and 1H. The time derivative of the inhalation pressure versus time graph can be used to determine the instantaneous rate of oxygen output required during inhalation at a certain moment in time. This positive time derivative valve can be corresponded with the slope of the proportional control valve 340 output. By adjusting this orifice size every few milliseconds during inhalation, creating a sum of linear equations, the actual oxygen output from the proportional control valve 340 can accurately approximate the pressure versus time graph. PID control can be used to continuously calculate the steady state error and adjust the linear equations to reduce the steady state error over time and with each succeeding breath of the user's breathing cycle 202.

In another example, the controller 380 can use a sinusoidal function to approximate a user's breathing pattern. While the computations can be intensive in creating the exact mathematical function, sinusoidal functions can be approximated computationally faster with low percent error using a Taylor polynomial expansion such that the degree of the polynomial n can be determined based on lag time and accuracy required for the PSA systems 10 described in FIGS. 3A-3K. As the degree of the polynomial n increases, the accuracy increases. In one example, the feedback control involves using pulse width modulation (PWM) control such that the compressor 310 airflow output can be changed per PSA cycle, e.g., on a breath by breath frequency, by adjusting the duty cycle or frequency of the pulse wave.

Using pressure sensor data, a pressure versus time graph can be generated. The time derivative of this pressure versus time graph can be calculated and, once a certain negative time derivative value is reached and the pressure detected is positive, valve 340 will fully close, and the PSA cycle will enter the oxygen purge phase 221. During this step, valves 350 and 360 will still be open and valve 370 will still be closed.

Referring again to the example PSA system 202 shown in FIG. 3H, during the desorption phase 241, the control system 380 determines that the actual pressure values are negative, and when the time derivative of the pressure versus time graph reaches a certain negative value, actuates valves 360 and 340 to close and actuates valves 350 and 370 to open. In one example, the controller can be configured to have default setting for the oxygen flow cycles. The setting can be set, for example, at 15 breaths per minute when the PSA system is turned on. The controller can be configured to start the inhalation period and adsorption phase only when the pressure sensor reaches a certain threshold. In one example, the pressure threshold can be based on a negative threshold pressure, such as −0.06 centimetre of water ($cmH_2O$). The controller 380 can dynamically change the rate of each PSA cycle time and as well as the time for each PSA phase 211, 221, 231, 241, depending on the breathing pattern of the user, on a breath by breath basis. Alternatively, the controller 380 can also configure the PSA system to not deliver oxygen when pressure sensor detects that the user is not inhaling air or there are other failed triggers that do not justify delivering the enriched oxygen gas 216 to the user. The default setting for a particular user can also change based on the user's specific breathing pattern using multi-predictive controls executed by the controller 380.

VII. Rapid Pulsed Pressure Swing Adsorption System

In one example, a rapid type pulsed pressure swing adsorption system (RPPSA system) is provided. The RPPSA system is an example of a pulsed pressure swing adsorption system 10. As illustrated by the phase graph 20F shown in FIG. 1J, an RPPSA system 10 can operate using one adsorbent column 320 and a pressurized air source 310, such that the cycle times of the PSA cycle of the RPPSA system 10 are faster than, e.g., of shorter duration than, the physiologically useful phases of respiration (generally less than 2 seconds). In this embodiment, oxygen pulses are produced one or more times during the physiologically useful phases of respiration, e.g., during the useful period of the inhalation phase and, in some embodiments, during the pre-inhalation period of the exhalation phase, of a user's breath. In some embodiments, and as shown in the example phase graph 20F, during the inhalation and exhalation phases, at times when oxygen enriched gas 216 is not being output during, pressurized air 236 can be output to the user, in order to increase $FiO_2$ levels in the user, as compared to natural aspiration with no pressurized air 236 being provided to the user. Further, in some embodiments, a positive end expiratory pressure (PEEP) can be provided by a pressurized air source 310 during the phases of user breathing which are not physiologically useful and/or when no oxygen gas 216 is being output to the user, such as during the non-useful period of the exhalation phase and during the anatomical dead space period of the inhalation phase of a user's breath.

In one example, the RPPSA system 10 includes one or more adsorbent beds in a pulsed PSA system 10 that generates raffinate product, such as enriched oxygen, non-continuously, e.g., in discrete pulses of enriched oxygen gas 216. These non-continuous oxygen pulses 216 are outputted during the adsorption phase 211, when pressurized air 236 enters the molecular sieve adsorbent bed and is separated by adsorption of the nitrogen by the adsorbent, resulting in production of a raffinate product, e.g., producing a raffinate product, which in the example of an oxygen concentrator disclosed herein, is an oxygen concentrated gas 216. This RPPSA system 10 alternates in operation between the adsorption phase 211 (also indicated as "A" in FIG. 1J), and a desorption phase 241 (also indicated as "D" in FIG. 1J), wherein during the desorption phase 241, oxygen enriched gas 216 is not being output and nitrogen is being desorbed from the molecular sieve adsorbent bed 955. The PSA cycle times of this rapid pulsed pressure swing adsorption system 10 are variable and defined in real time on a breath by breath basis, by the user's breathing rate to determine the inhalation and exhalation cycles of the user. In this example, the output of oxygen enriched gas 236 to the user can be precisely adjusted to the user's requirements and breath flow phases individually for each breath taken by the user, e.g., on a breath by breath basis, using one or more of adjustments made to the PSA cycle times for the various PSA phases 211, 221, 231, 241, the user's measured breathing pressure 16 and/or breath rate, and a blower flowrate output, which in one example can be adjusted by varying the level of power supplied to the blower 14 or microblowers 816.

The RPPSA system 10 can incorporate components such as thin adsorbent beds 755, 955 to limit kinetic resistance, high volumetric flow low pressure changes blowers that allow higher product gas flow and maintain product gas purity, and ultra-rapid cycle times greater than 2 Hz to improve the productivity of the thin adsorbent bed 755, 955. In one example, microblowers 816 are used to create an ultra-thin oxygen concentrator device wherein cycle times of above 10,000 Hz are possible, as illustrated by the example shown in FIGS. 7A-12. The URPSA system configuration 700, 900 can be utilized with different adsorbent materials to provide a PSA system 10 which is advantaged by compact size and packaging, user convenience and portability, and efficiency of operation, This ultra-rapid pressure swing adsorption (URPSA) system 700, 900 can be used not just for producing an oxygen enriched gas 216, but also with different adsorbent materials. pressure swing adsorption systems 10 for the production of gas species such as nitrogen, hydrogen, methane, etc.

In the examples shown in FIGS. 7A-12, the RPPSA system 700, 900 is a single bed ultra-rapid pressure swing adsorption (URPSA) system that has ultra-rapid PSA cycle times, in some cases greater than 2 Hz. The use of ultra-rapid PSA cycle times allows for the PSA system 700, 900 to be reduced in size and increases the energy efficiency by the reducing the total amount of zeolite adsorbent required to create the same amount of product gas as compared to a PSA system operated with slower PSA cycle times. Further, by using ultra-rapid PSA cycle times, it is possible to generate "quasi-continuous" raffinate product, eliminating the need for multiple adsorbent beds in pressure swing adsorption applications where continuous product output is necessary.

In this example, a pancake-like thin zeolite adsorbent bed 755, 955 with a length to diameter ratio, or L/D, of less than 1:1 is utilized. This allows the pressurized inlet gas 236 to linearly diffuse through the adsorbent column faster than high L/D adsorbent beds while also limiting axial diffusion and reducing pressure drop across the adsorbent bed 755, 955.

In this example, by allowing the RPPSA system to utilize lower pressure ratios, i.e. 1.2:1, with thin adsorbent beds 755, 955, higher volume and/or higher purity product gas can be produced at lower incoming air pressures. This oxygen product gas 216 can be produced at a purity level such the oxygen product gas 216 having an oxygen output pressure potentially as low as 4 cmH2O, nearly matches a user's breathing pressure demand. This allows low pressure, higher volume oxygen output to be produced from a PSA system 10 using centrifugal air blowers such as those used in CPAP machines, which produce less than 100 cmH2O air pressure, rather than prior art oxygen concentrator air compressors where the pressurization is over 1000 cmH2O air pressure. This lower O2 pressure output is useful since mass flow of O2 is much more important than pressure for gas exchange and PaO2 saturation during respiration, especially given that emphysema (COPD) patients have lower lung compliance than normal people, and hence the elastic forces required to open alveoli to create useful gas exchange in lungs is much less than the higher pressure oxygen output from prior art oxygen concentrators. Further, lower pressurization ratios in some embodiments of RPPSA allow for much higher energy efficiencies compared to prior art PSA systems, since less energy is required to compress the input air, hence watts of power consumption per liter per minute of oxygen produced is decreased substantially, potentially to one-tenth the power consumption of prior art PSA systems.

Further, the velocity of the compressed air 236 is related to the pressure ratios utilized, and the velocity of air is inversely proportional to the time exposure to the adsorbent material. Hence, with thin adsorbents 755, 955, where the mass transfer constant k is a large value, it is undesirable to utilize high pressures since that would limit the time exposure of the air to the adsorbent material, hence reduce product gas (in this example, O2 gas) purity and output. The present disclosure seeks to solve this problem through the creation of an RPPSA system that can facilitate ultra-rapid pressurizations and depressurizations in a thin profile package, with the use of lower pressure ratios in conjunction with thin adsorbent beds 755, 955. Further, since pressure and volume are fundamental tradeoffs in compressor design and/or selection, with lower pressure ratios it is possible to utilize compressors and/or blowers that have high input gas volume flowrates, increasing product gas output.

The example of a thin-bed structure of the adsorbent material is non-limiting. For example, in one embodiment, structured adsorbents with low pressure drop could be utilized. These structured adsorbents could comprise foams, laminates, 3D printed adsorbents, honeycombs, and/or highly spherical or patterned adsorbent beads. Further, these adsorbents can be a thin layer of LiX zeolite pellets or a monolithic structure with a length to diameter, or L/D ratio, of less than 0.1 for example, to facilitate rapid mass transfer, improve adsorption kinetics, and minimize pressure drop during ultra-fast adsorption and desorption cycles. The activated alumina or silica gel is meant to adsorb water vapor and carbon dioxide, which in small concentrations can over time reduce the nitrogen adsorption performance of the LiX zeolite adsorbent.

In one example, a very thin ultra-rapid pressure swing adsorption system 700, 900 can be built using microblowers or micropumps 816, which in one example are arranged in a microblower array 810. In one embodiment, the feed air is pressurized using piezoelectric microblower(s) 810. These piezoelectric microblowers 816 have a thin profile and utilize ultrasonic 26 kHz vibration of a piezoelectric ceramic material, for example, to discharge air from the microblower 816 at a gauge pressure above 1.9 kPa. Further, the ultra-rapid low-pressure swing adsorption system 10 utilizes one or more rapid actuating valves such as piezoelectric or solenoid valves to produce rapid adsorption and desorption cycles, having ultra-rapid cycle times which in some embodiments range from about 10 Hz to about 10,000 Hz. The piezoelectric microblowers 816 are positioned in the URPSA system 700, 900 next to the monolithic adsorbent material and blow pressurized air toward the adsorbent material, with the one or more valves on one side of the adsorbent, rapidly actuating to depressurize the system via an atmospheric purge, and micro-sized air blowers 816 on the opposite side of the absorbent material to evenly distribute the pressure from the piezoelectric microblowers 816 across the entire adsorbent monolith.

In one embodiment, this ultra-rapid pressure swing adsorption could be used to produce medical oxygen. In one example, the single adsorption bed and pulsed pressure swing adsorption process allows the PSA system to quasi-continuously produce oxygen product gas during inhalation via the ultra-rapid cycle times and then conserve oxygen during exhalation by implementing a longer purge cycle time or longer desorption phase cycle time.

A. RPPSA with Multiple Valves and Oxygen Purge Tank

Figure 5:
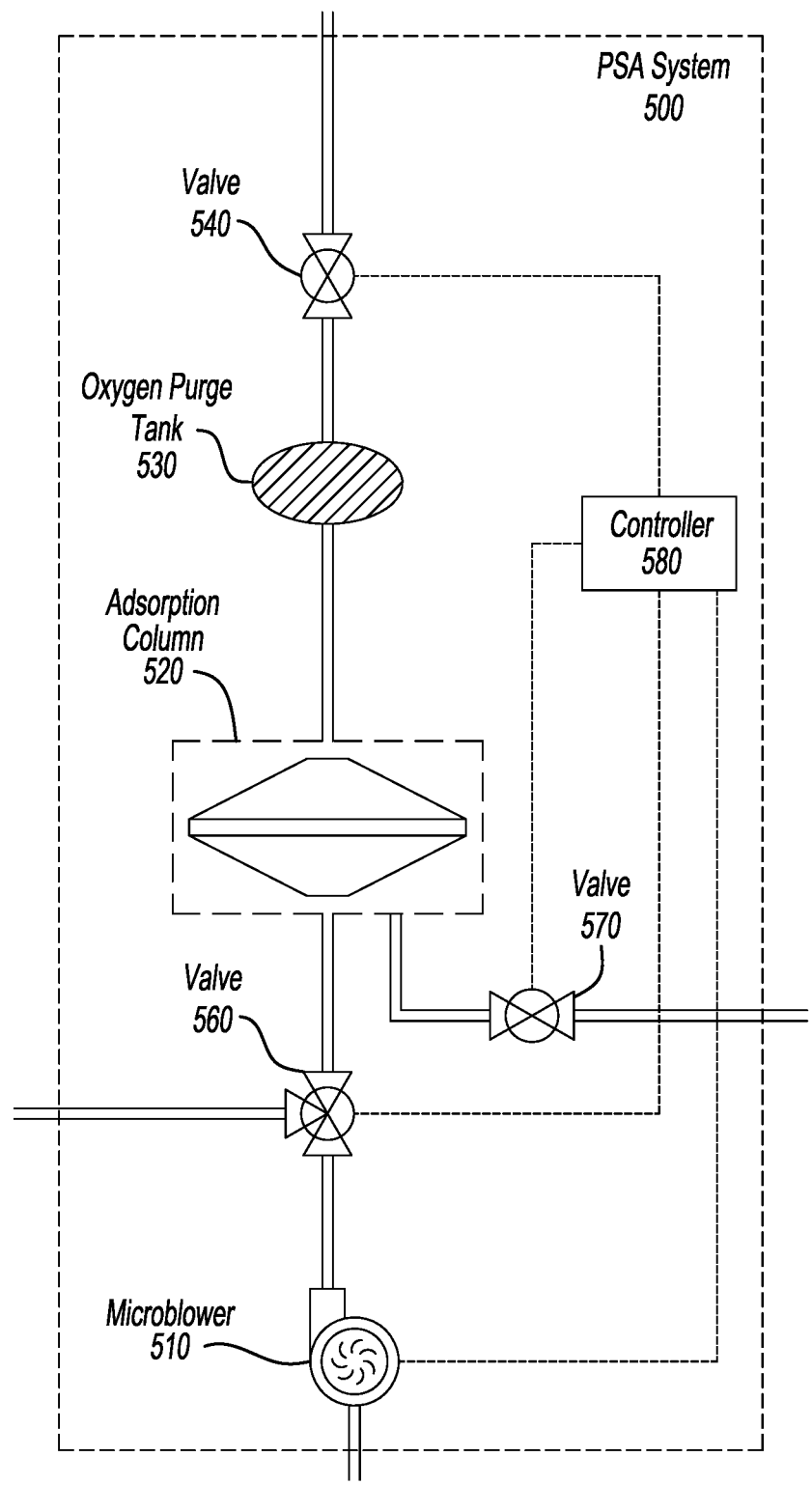
FIG. 5 shows a schematic diagram of a Pressure Swing Adsorption system according to some embodiments.
Figure 6:
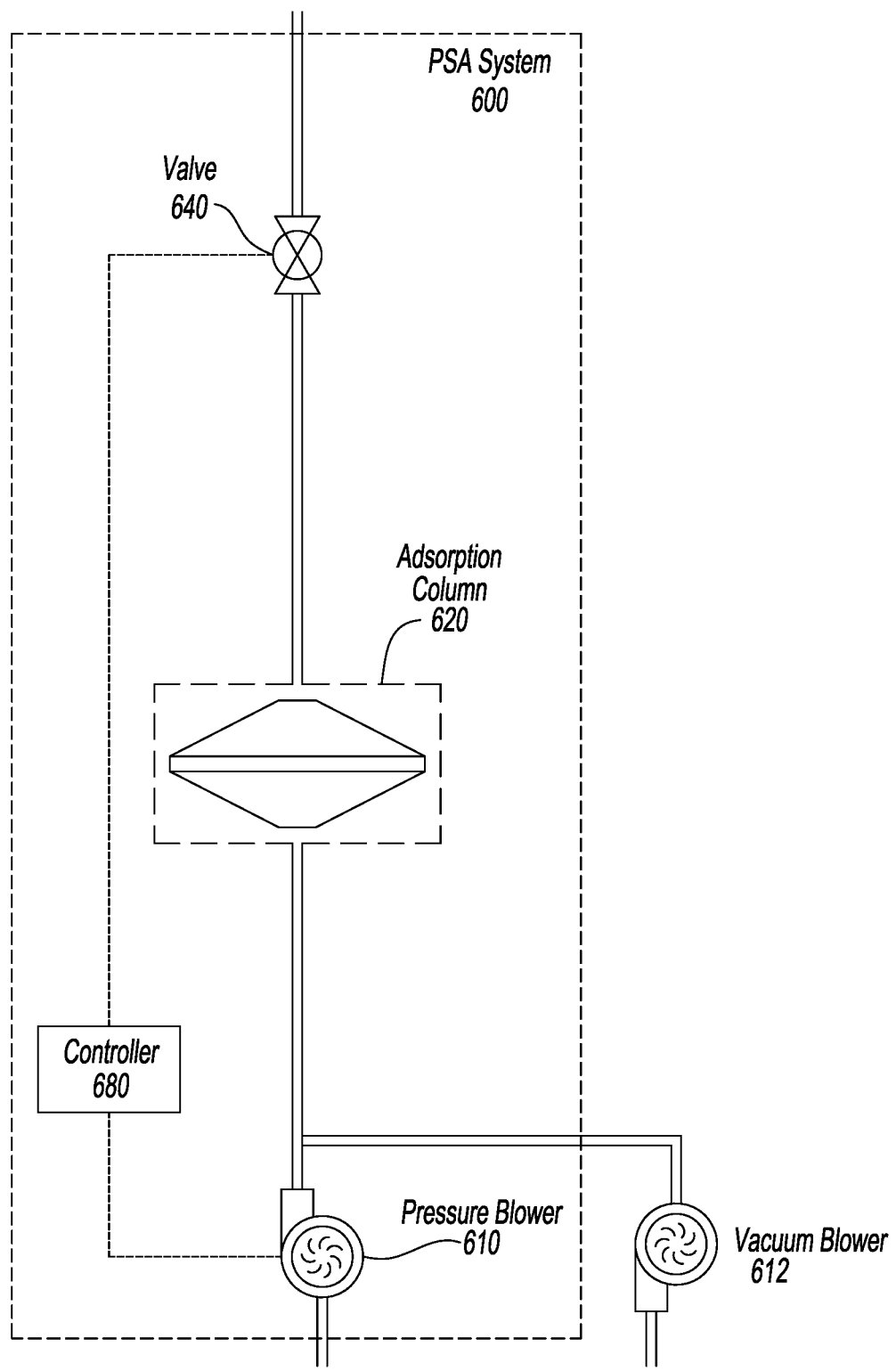
FIG. 6 shows a schematic diagram of a Pressure Swing Adsorption system according to some embodiments.

Referring to FIG. 5, shown is an example pressure swing adsorption (PSA) system 500 which generates raffinate product such as enriched oxygen gas 216 non-continuously, in rapid pulses, such that the PSA system 500 can be characterized as a rapid pulse PSA (RPPSA) system 500. The microblowers 510, 610 described in both FIGS. 5 and 6 are used to facilitate ultra-rapid type pressurization and vacuum depressurization of gas and air in the RPPSA system 500. In this configuration, the microblowers can cause cycle times of 10,000 Hz with a low-pressure gradient which allow for rapid PSA cycles. This process allows for a faster oxygen purge 221 and desorption 241 phases in the pressure swing adsorption cycle.

In this example, the PSA system 500 comprises at least one microblower 510, an adsorption column 520, and an oxygen purge tank 530. The compressor 510, adsorption column 520, and oxygen purge tank 530 can be connected to each other in series, and shown in FIG. 5. A valve 560 operably connects the microblower 510 to the adsorption column 320 and acts as a gate for either allowing or blocking gas to flow from the microblower 510 to the adsorption column 520. The PSA system 500 can also include a controller 580 which can monitor and control the amount and direction of flow of the gases by selectively controlling the power delivered to the microblower 510, valve 560, and/or valve 540. In one example, valve 540 is a two-way solenoid valves and valve 560 is a 3-way solenoid valve. In this example, the adsorption column 520 can include a thin, pancake-like, zeolite adsorbent with a length to diameter (L/d) ratio of less than 1:1. In this example, the microblower 510 can be an array of piezoelectric microblowers embedded on a printed circuit board (PCB), such as the array 810 of microblowers 816 shown embedded on a printed circuit board 800 shown in FIGS. 8 and 11.

In one example, the controller 580 can actuate the PSA system 500 to enter into the adsorption phase 211 at a selected one of the beginning of the user's inhalation phase, slightly before the beginning of the user's inhalation phase such as during a pre-inhalation period of the exhalation phase preceding the inhalation phase, or slightly after the beginning of the user's inhalation phase depending on the control schema used. During this adsorption phase 211, valve 560 is set open, to connect the output of microblower 510 to the inlet of adsorption column 520, and valve 570 is closed. At this point, the microblower 510 receives atmospheric air, pressurizes the atmospheric air to create pressurized air 236, and outputs the pressurized air 236 through the valve 560 to the inlet of adsorption column 520. In one example, the pressurized air 236 has an air pressure which is greater than 1 atmospheric pressure. The adsorption column 520 contains zeolite which adsorbs the nitrogen from the pressurized air 236 to produce a raffinate which is an oxygen enriched gas 216. At this point, valve 570 is closed in an "OFF" position. The oxygen enriched air 216, absent most of the nitrogen, flows from the adsorption column 520 to the oxygen purge tank 530, with a resultant pressure drop across the adsorption column 520. Pressure in oxygen purge tank 530 is only slightly higher than atmospheric pressure during this adsorption phase 211. Valve 540 is also set to open such that the oxygen enriched gas 216 flows from oxygen purge tank 530 to the user.

In one example, the microblower 510 is not set to output a constant amount of pressure. Rather, the controller 580 dynamically adjusts the air pressure and flowrate output from the microblower 510 in order to change the oxygen output 216, on demand as needed to meet the user requirements for oxygen output 216 defined by the breath flow phases of the user's breath. The adjustment in air pressure and flowrate output of the microblower 510 can occur on a breath by breath basis, to adjust to breath to breath variations in the user's breathing cycle 202. Adjustment of the microblower 510 air pressure and/or flowrate output may be required because the pressure difference required to perform the adsorption phase 211 is variant upon the breathing pressure from a user's inhalation phase as well as the porosity (adsorption capability of the filter) of the filter, which can change from breath to breath and/or over time, for example, based on the condition of the adsorbent. The controller 580 can adjust the microblower 510 using feedback control such that the microblower 510 operation may be adjustable ever millisecond or less, depending on the sampling frequency utilized by analog or digital control sensors in the PSA system 500 and/or an oxygen delivery device 342 connected to the PSA system in use.

In a next step, the controller 580 actuates the PSA system 500 to enter an oxygen purge phase 221, during the dead space period of the inhalation phase. Valve 560 remains set to open, to connect the output of the microblower 510 to the inlet of adsorption column 520. Valve 540 is now switched to closed in an "OFF" position, preventing flow of enriched oxygen gas 216 from the oxygen purge tank 530 to the user. As concentrated oxygen 216 flows from the adsorption column 520 into the oxygen purge tank 530, pressure in oxygen purge tank 530 increases, although it remains less than the pressure of air entering adsorption column 520.

In one example, the microblower 510 can be set to an always "ON" position such that the microblower 510 is constantly outputting pressurized atmospheric air 236 through its outlet. During the oxygen purge phase 221, the pressurized air 236 from the microblower 510 will flow out of the PSA system 500 back into the atmosphere without first entering the adsorption column 520.

Following the oxygen purge phase 221, the controller 580 actuates the PSA system 500 to enter the desorption phase 241 during the user's exhalation phase. During the desorption phase 241, valve 540 remains closed. Valve 560 is configured to allow the pressurized air 236 from the microblower 510 to directly release out of the PSA system 500, back into the atmosphere. Valve 570 is opened in an "ON" position allowing flow of gas from the adsorption column 520 to the atmosphere. Valve 340 remains closed in an "OFF" position since during the exhalation phase, the user does not have a requirement for enriched oxygen gas 216. During the desorption phase 241, the pressure gradient through the adsorption column 520 reverses such that the outlet is at higher pressure than at the inlet of the adsorption column 520. As the pressure in the adsorption column 520 decreases, nitrogen desorbs from the zeolite adsorbent, e.g., re-enters the gaseous state. The pressure gradient causes the air in the adsorption column 520, including the desorbed gaseous nitrogen, to flow out the inlet of the adsorption column 520, through valve 570, to release the desorbed nitrogen gas from the PSA system 500 and back into the atmosphere. Some concentrated oxygen flows from oxygen purge tank 530 back into adsorption column 520 through pressure equalization. When the controller 580 senses that the user's exhalation phase is almost completed, the controller 580 actuates the PSA system 500 to return to the adsorption phase 211 and the PSA cycle repeats.

B. RPPSA with Single Valve

FIG. 6 illustrates a rapid pulse PSA (RPPSA) system 600 similar to that of PSA system 500 of FIG. 5. As illustrated in FIG. 6, the RPPSA system 600 comprises at least one microblower 610 and an adsorption column 620. The microblower 610 and adsorption column 620 can be connected to each other in series. The PSA system 600 can also include a controller 680 which can monitor and control the amount and direction of flow of the gases by controlling the microblower 610 and a two-way valve 640. In this example, the adsorption column 620 can include a thin, pancake-like, zeolite adsorbent with a length to diameter (L/d) ratio of less than 1:1. In this example, the microblower 610 can be an array of piezoelectric microblowers, such as the array 810 of microblowers 816 shown embedded on a printed circuit board 800 shown in FIGS. 8 and 11.

In one example, microblower 610 is not set to a constant amount of pressure, as the pressure difference required at a given time is variant upon the breathing pressure from a user's inhalation phase at that time, as well as the porosity (adsorption capability of the filter) of the filter, which can change from one PSA unit to another due, for example, manufacturing variation of the filter. In one example, the controller 680 can adjust the air pressure and flowrate output from the microblower 610 in order to change the oxygen output 216, depending on user requirements and/or the user's breath flows and/or breathing cycle 202 detected by the controller 680. In one example, the controller 680 can adjust the microblower 610 pressure and/or flowrate output using feedback control, such that the microblower 610 pressure and/or flowrate output is adjustable every millisecond or less.

In one example, the microblower 610 is bidirectional such that the microblower 610 can be configured to deliver atmospheric and pump pressurized air 236 into the adsorption column 620 in one direction, and in the other direction operate to draw air from the adsorption column 620 during the desorption phase 241 of the PSA cycle. In one example, this microblower 610 could comprise a singular or array of fans, blowers, centrifugal, or diaphragm pumps such that high volumetric air flow and low pressurization are produced. For example, using this configuration, less than 1.4 atmospheres of pressurization can be generated from the blower 610. In one example, these changes in pressure could be ultra-low wherein 2.1 mmH2O of gauge pressure is produced, allowing for high volumetric flowrates and with ultra-low pressure drop adsorbent materials. In another example, the microblower 610 comprises an array 810 of microblowers 816 such that some of the microblower are configured to intake atmospheric air, pressurize the air, and deliver the pressurized air to the adsorption column 620 to actuate adsorption of nitrogen from the air 236, thus producing an oxygen enriched gas 216, and some of the microblowers 816, shown collectively in FIG. 6 as a vacuum blower 612, are configured in the reverse direction to flow air from the adsorbent such that nitrogen is desorbed from the adsorbent and vented as gaseous nitrogen back into the atmosphere during a desorption phase 241 of the PSA cycle. In this case, during the oxygen purge phase 221 and the desorption phase 241, the reverse microblowers 816 of the microblower array 810 are actuated, e.g., powered on and intake the nitrogen and excess oxygen from the adsorption column 620 and release the gases back into the atmosphere back in the direction from where the atmospheric air came from in the adsorption phase 211. In one example, during the oxygen purge 221 and desorption 241 phases, the microblowers 810 shut off and the solenoid valve shuts off. In one example, the internal pressure of the zeolite adsorbent pushes nitrogen back out, causing the nitrogen to desorb as a gas. In one example, the reverse microblowers 810 are selectively turned on to speed up the pressure equalization phase 231, e.g., decrease the pressure equalization phase cycle time, in addition to the flow of air from the internal pressure of the zeolite.

In one example, the microblowers 610, array 810 are controlled by a MOSFET switch 812 or some other type of microcontroller 814 that can regulate voltage of the MOSFET 812. In this example, only one solenoid or piezoelectric valve is required in order to facilitate depressurization and pressurization, along with production of output gas 216. With piezoelectric microblowers 816, it is possible to shut each individual microblower 816 or microblower array 810 ON or OFF extremely rapidly using MOSFET switches 812. For example, a pulse width modulation control can simulate a 26 kHz square wave form of the piezoelectric microblowers 816, precisely controlling the piezoelectric oscillations in order to turn the microblowers 816 ON or OFF without any partial oscillations, thus allowing full depressurization and pressurization cycles within the PSA system 600, even at extremely rapid cycle times.

VIII. Exemplary Ultra-Rapid Pressure Swing Adsorption System

In one example, provided is an example PSA system 700 similar to that of the PSA system 600 of FIG. 6. In this example, as illustrated in FIGS. 7A-B, a small form factor PSA system 700 is configured to provide enriched oxygen 216 to a user, where the small form of the PSA system 700 is advantaged by being lightweight and portable for the convenient of the user.

Figure 7A:
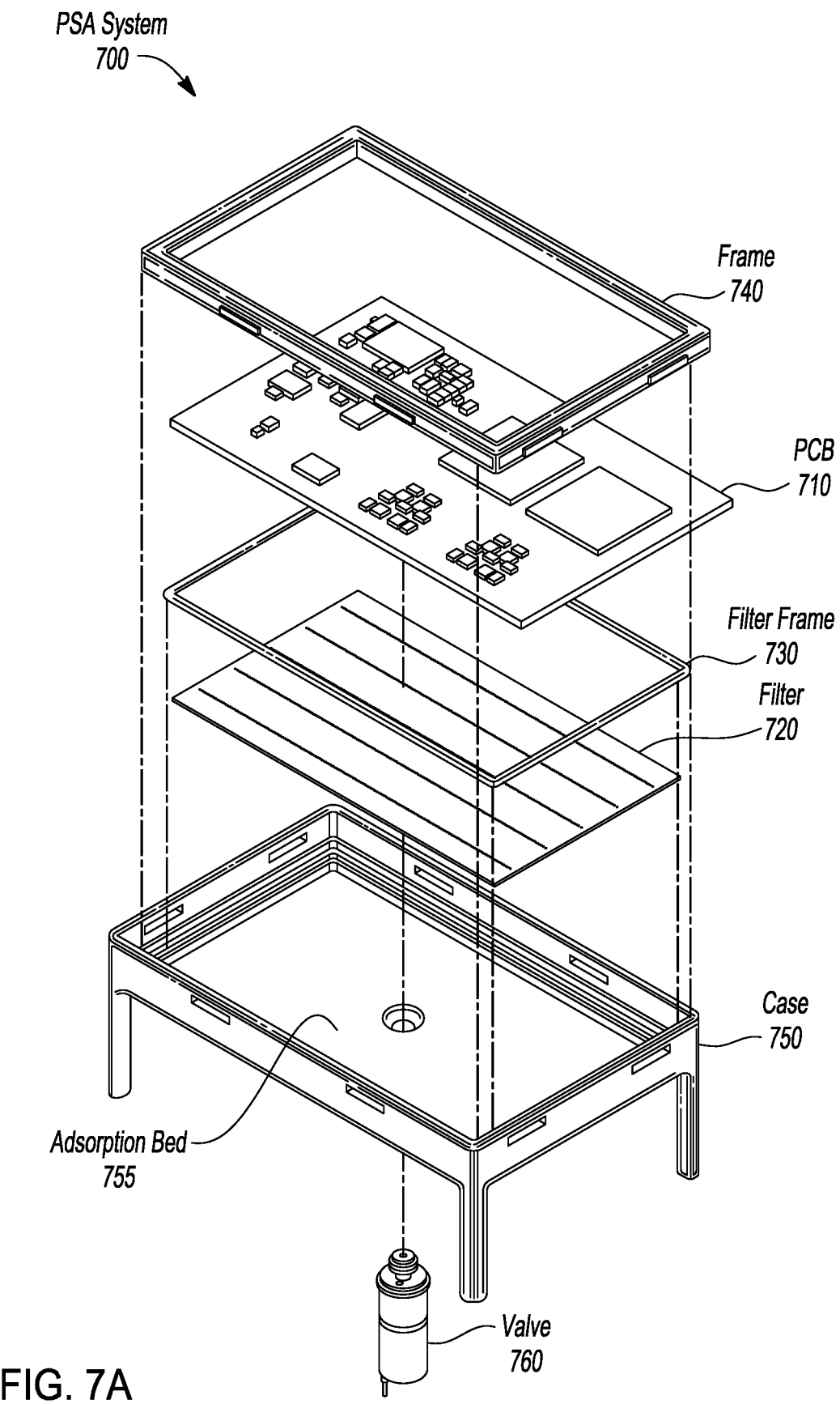
FIGS. 7A-B show schematic diagrams of an exemplary Pressure Swing Adsorption system according to some embodiments.
Figure 7B:
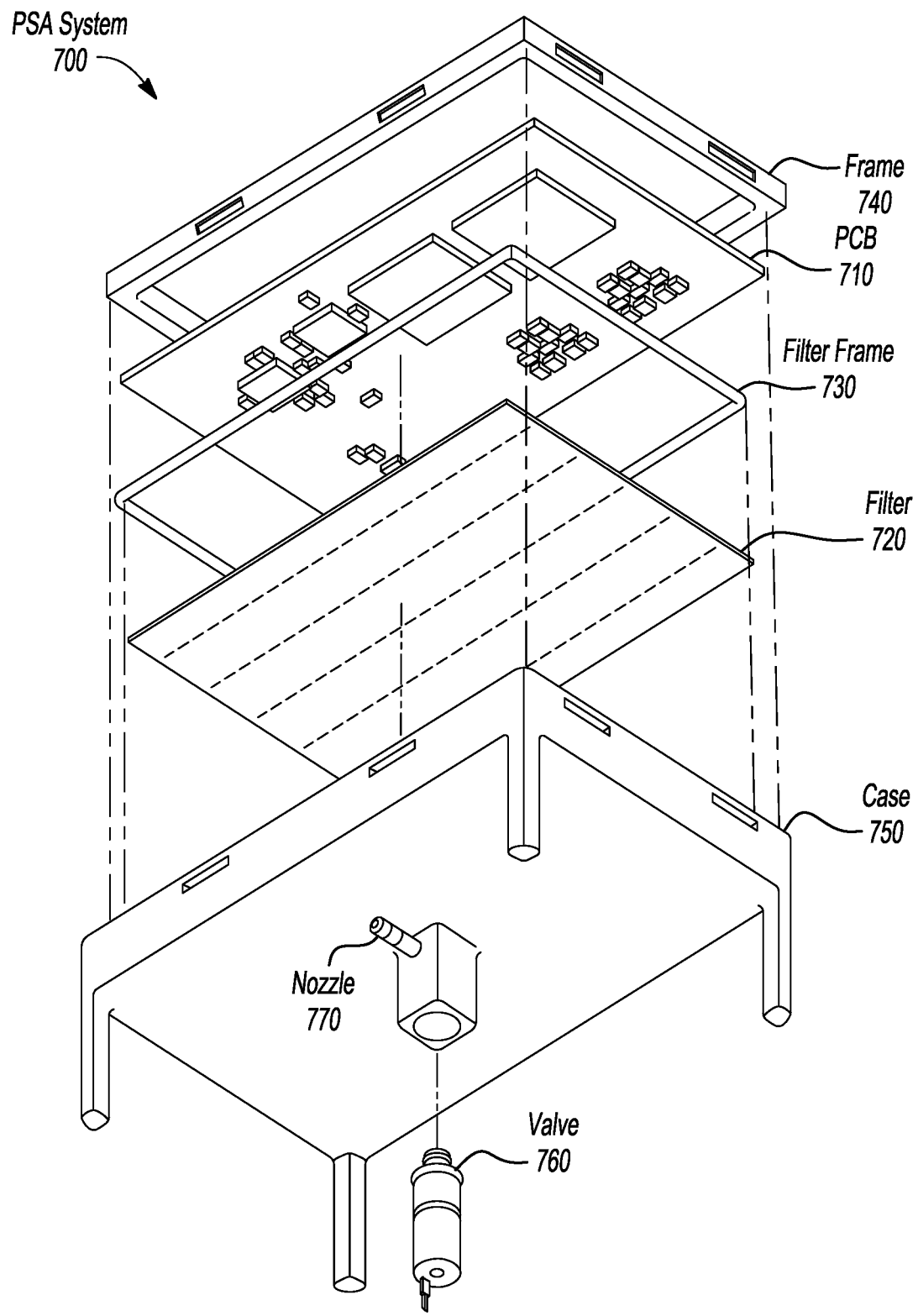

As illustrated in FIGS. 7A-7B, provided is a PSA system 700 shown in an exploded perspective view. FIG. 7A illustrates the PSA system 700 in an exploded perspective top view and FIG. 7B illustrates the PSA system 700 in an exploded bottom view. As illustrated in FIGS. 7A-7B, a number of layers of components are combined to form the PSA system 700. In one example, provided is a Printed Circuit Board (PCB) 710 including a microblower array 810 comprised of a plurality of microblowers 816 embedded on the PCB 710. The PSA system 700 also includes a filter 720 and a filter frame 730 configured to separate the PCB 710 from contact of the adsorbents, which in the present example are configured as a bed 755 of zeolite pellets. In one example, the filter 720 is a mesh or sheet metal to protect the PCB 710 from contact with the zeolite bed 755 and to prevent any particles other than air from reaching the zeolite bed 755. In an example shown in FIG. 10, the filter 720 is supported in the PSA case 750 by a plurality of rails 732, spaced so as to not interfere with air flow through the adsorption cavity defined by the PSA case 750. The filter 720 is in a mesh shape to allow pressurized air from the PCB 710 to diffuse through the filter 720 and reach the zeolite comprising the adsorption bed 755. Further, in another example, an electrostatic filter can be placed on one or more portions of the PCB 710 to reduce dust accumulation in the PSA system 700 and hence increase the lifecycle of the microblower array 810. Below the filter 720 is a case 750 for the PSA system 700. A cavity defined by the case 750 houses an adsorption bed 755 configured to store adsorbent material such as zeolite pellets. The adsorption bed 755 is thin and has a length to diameter ratio of about 1:1. The adsorption bed 755 and support rails 732 (see FIGS. 10-12) are configured to allow the filter 720 and PCB 710 to rest above the adsorption bed 755 such that the zeolite in the adsorption bed 755 is prevented from coming in contact with either of the filter 720 and the PCB 710. A top frame 740 is configured to fit snugly inside an outer portion of the case 750. The frame 740 and case 750 is configured in a way that the frame 740 and case 750 will sandwich the PCB 710 and filter 720 in a fixed position so that PCB 710, filter 720, and any zeolite pellets in the adsorption bed 755 are in a locked position relative to each other.

At a bottom portion of the case 750 is a circular shaped divot comprising a nozzle 770 configured to receive a valve 760, such as a solenoid valve. The nozzle 770 is configured to connect the valve 760 to the PSA system 700. The solenoid valve can receive and release enriched oxygen 216 that is filtered in the PSA system 700 through the thin zeolite mesh bed 755. The valve 760, similar to that of valve 640 of FIG. 6, is configured to regulate the flow of oxygen enriched gas 216 from the PSA system 700 to the user. The nozzle 770 also comprises a release portion for oxygen to flow from the PSA system 700 to the user when the valve 760 is configured in an "ON" position.

Figure 8:
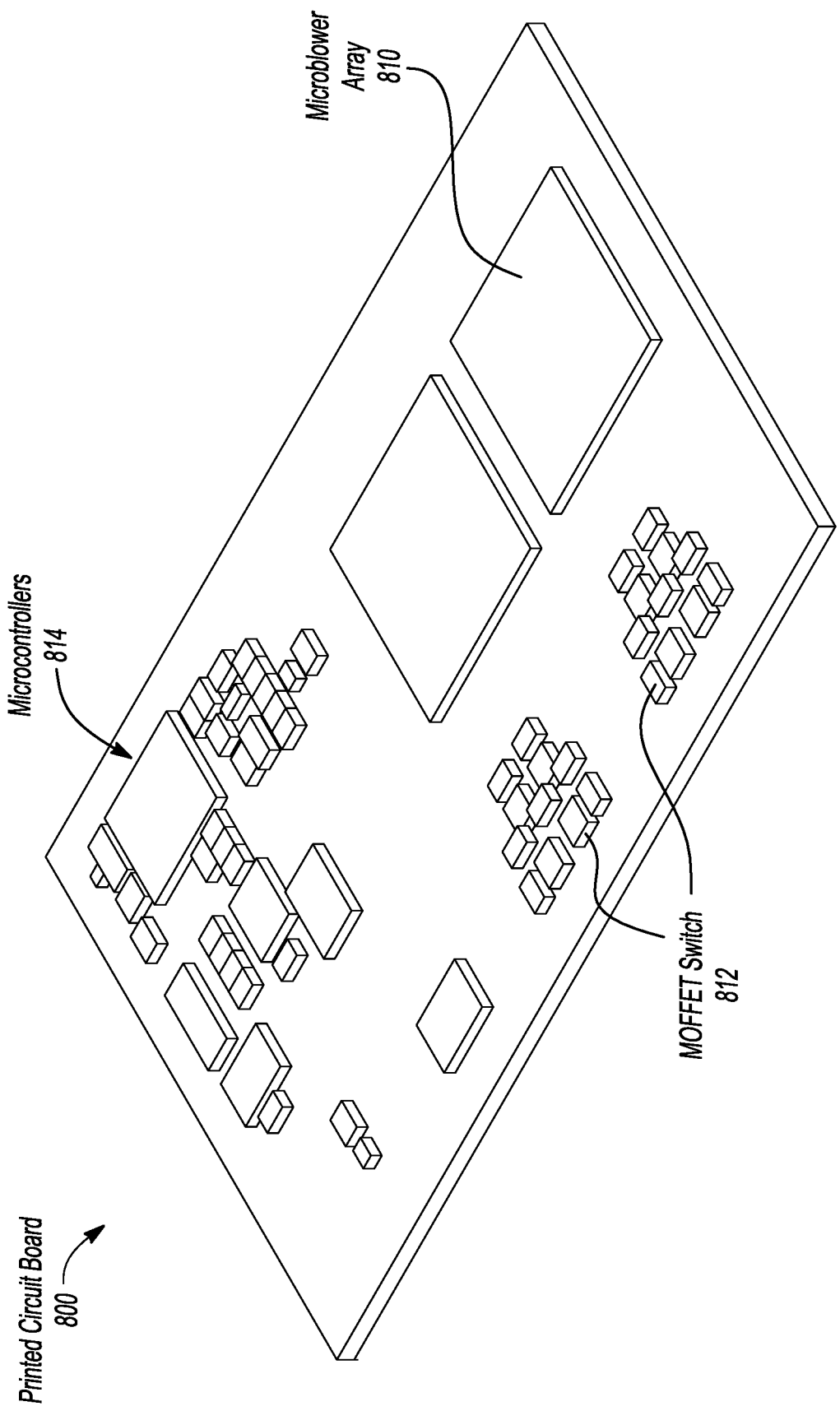
FIG. 8 shows a schematic diagram of an exemplary component of the Pressure Swing Adsorption system according to the Pressure Swing Adsorption system of FIGS. 7A-B.

FIG. 8 illustrates a more detailed view of the PCB 710 of FIGS. 7A and 7B, where in the example illustrated in FIG. 8, the PCB 710 is configured as a Printed Circuit Board (PCB). The PCB 800 includes a microblower array 810, a MOSFET switch 812 configured to regulate the voltages of the microblower array 810, effectively regulating the amount of pressurized air flowing in and out of the piezoelectric microblowers 816 of microblower array 810. The PCB 800 also includes microcontrollers 814 and microprocessors to regulate the valve 760, microblowers 816, MOSFET 812, and to provide power to the other components of the PCB 800.

In this example, there can be any number of microblowers 816 in the microblower array 810. In one example, the microblowers 816 are configured in a grid pattern. In one example, USB power supply (not shown) can be configured to power the PCB 800 and its components including the microprocessors 814 and microblower array 810. In one example, on the reverse side of PCB 800 (see FIG. 7B) are another set of microblower arrays 810 facing the opposite direction. The reverse set of microblowers 810 serve the purpose of moving air, particularly nitrogen from the zeolite chamber bed 755 back into the atmosphere during a desorption phase 241, where the nitrogen rich air is moved in a direction opposite the air flow generated by the microblower array 810 operating during the adsorption phase 211. In one example, both sets of microblower arrays 810 are on mounted on the same side of the PCB 800, with at least one array 810 operable to move desorbed air away from the adsorbent bed 755, and at least one array 810 810 operable to move atmospheric air to the adsorbent bed 755 during an absorption phase 211.

In this example, the microcontroller 814 synchronizes actuation of the desorption phase 241 of the PSA system 700 with the exhalation phase of the user's breathing cycle, such that during the desorption phase 241 the microblowers 816 will blow in a reverse direction, e.g., will blow air away from the adsorption bed 755, causing a vacuum-type desorption of the adsorption bed 755, during which nitrogen desorbed from the adsorption bed 755 and any excess enriched oxygen gas 216 will flow in the opposite direction of the air flow from the adsorption phase 211, through the filter 720 and through the PCB 710 via the microblower array 810, to be released back into the atmosphere.

Figure 9A:
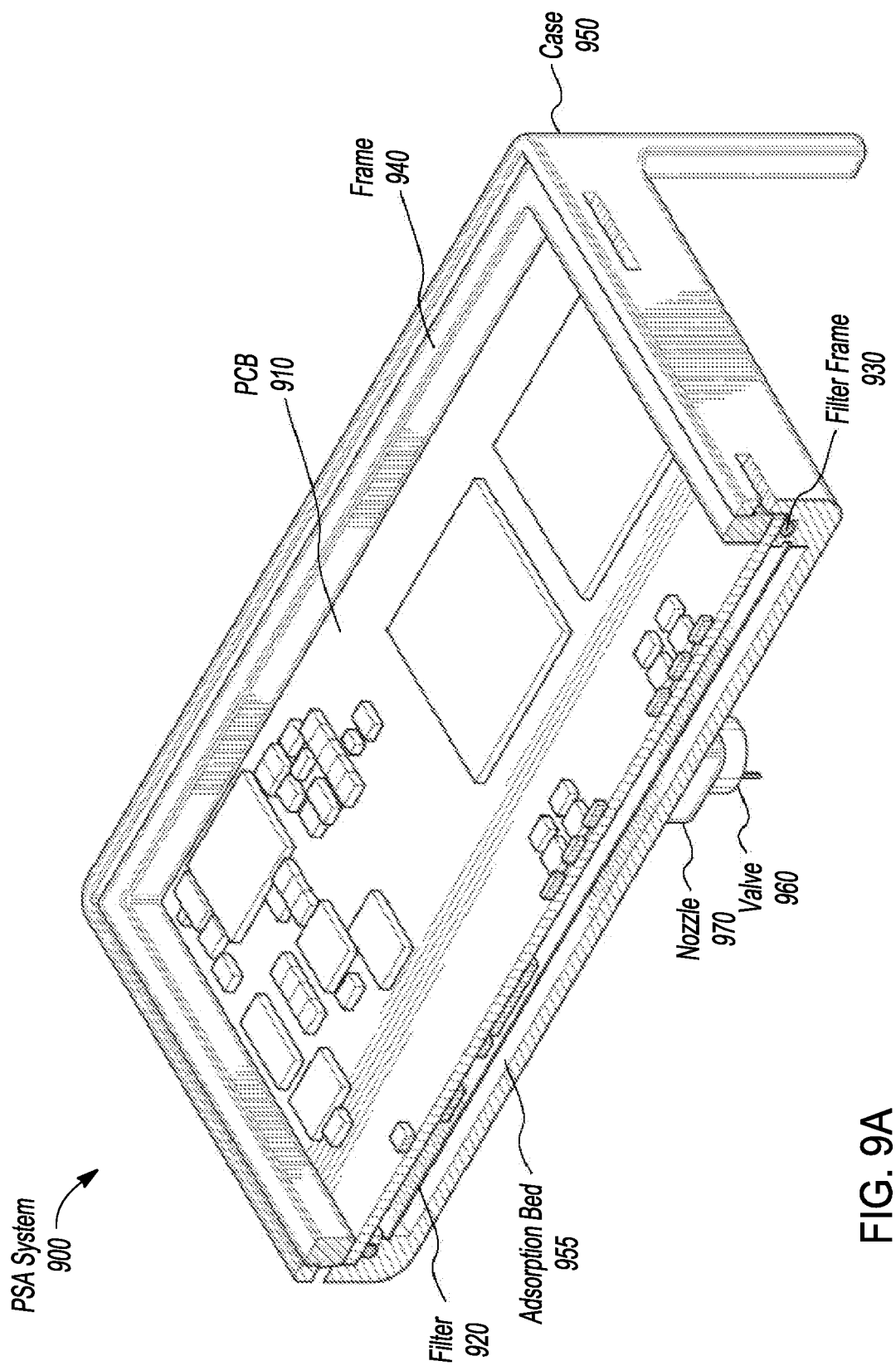

FIGS. 9A-9D illustrate an example PSA system 900 similar to that of the example PSA system 700 of FIGS. 7A-B. FIG. 9A shows a partial sectional perspective view of the PSA system 900 in an assembled state, illustrating the thin profile and compact packaging of the PSA systems 700, 900 and including a filter frame 930, a filter 920 and a printed circuit board (PCB) 910 layered in a case 950 and retained in the case 950 in the layered arrangement by a frame 940. The filter 920 functions as described for the filter 720 of the PSA system 700 shown in FIGS. 7A-7B, to prevent particles other than air from migrating from the adsorbent bed 955 to the PCB 910 and/or the microblower arrays 810, and to prevent particles other than air from migrating from the atmosphere, via the microblower arrays 810, to the adsorbent bed 955. As shown in FIG. 9A, the adsorbent bed 955 is positioned in a cavity defined by the case 950 such that atmospheric air blown by the microblower arrays 810 onto the adsorbent bed 955 during an adsorption phase 211 can react with the adsorbent bed 955, to absorb nitrogen from the atmospheric air and to produce oxygen enriched gas 216 which can be released from the cavity of the PSA case 950 via a release nozzle 970 and/or a valve 960. In one example, the microblower array 810 is bidirectional such that the microblower array 810 can be configured to operate in a first direction to intake atmospheric and pump pressurized air 236 into the adsorption bed 955 via the filter 920 during an adsorption phase 211, and to operate in a second direction to draw nitrogen gas desorbed from the adsorption bed 955 during a desorption phase 241 out of the case 950 via the microblower array 810. As previously described herein the microcontroller 814 of the PSA system 900 can be configured to detect the inhalation and exhalation phases of a user's breathing cycle 202, and can be further configured to synchronize actuation of one or more of the various phases 211, 221, 231, 241 of the PSA cycle with the user's inhalation and exhalation phases, on a breath by breath basis.

In one example, the microblower array 810 could comprise a singular fan or array of fans, blowers, centrifugal pumps, diaphragm pumps or a combination of these, wherein high volumetric air flow and relatively low pressurization of the air moved by the microblower array 810 is produced. This could mean, for example, less than 1.4 atmospheres of pressurization from the blower array 810. These changes in pressure could be ultra-low, such that about 2.1 mmH2O of gauge pressure is produced, allowing for high volumetric flowrates and the use of ultra-low pressure drop adsorbent materials. In another example, a microblower array 810 can comprise a plurality of microblowers 816 such that some of the microblowers are configured to intake atmospheric air, pressurize the air, and deliver the pressurized air 236 to the adsorption bed 955 and some of the microblowers are configured to move air in the reverse direction to intake the nitrogen desorbed from the adsorbent bed 955 and release the gaseous desorbed nitrogen back into the atmosphere during a desorption phase 241 of the PSA cycle performed by the PSA system 900. In one example, a solenoid valve or series of solenoid valves could be used to replace the microblowers 816 to facilitate vacuum depressurization, as illustrated in the PSA system 700 shown in FIG. 10. In this example, during the oxygen purge phase 221 and the desorption phase 241, the reverse microblowers 816 of microblower array 810 are turned on and intake the nitrogen and excess oxygen from the adsorption bed 755 and releases the gases back into the atmosphere in a direction opposite from the where the atmospheric air was taken in during the adsorption phase 211.

In one example, during performance of the oxygen purge 221 and desorption 241 phases of the PSA cycle, the microblowers 816 shut off and the solenoid valve 760 shuts off. In one example, the internal pressure of the zeolite pushes nitrogen back out, e.g. causes adsorbed nitrogen to desorb from the adsorption bed 755, 955 in a gaseous form. In one example, the reverse microblowers 816 can be powered on to speed up the pressure equalization phase 231, in addition to flowing air from the adsorption bed 755, 955 during the desorption phase 241.

Figure 9B:
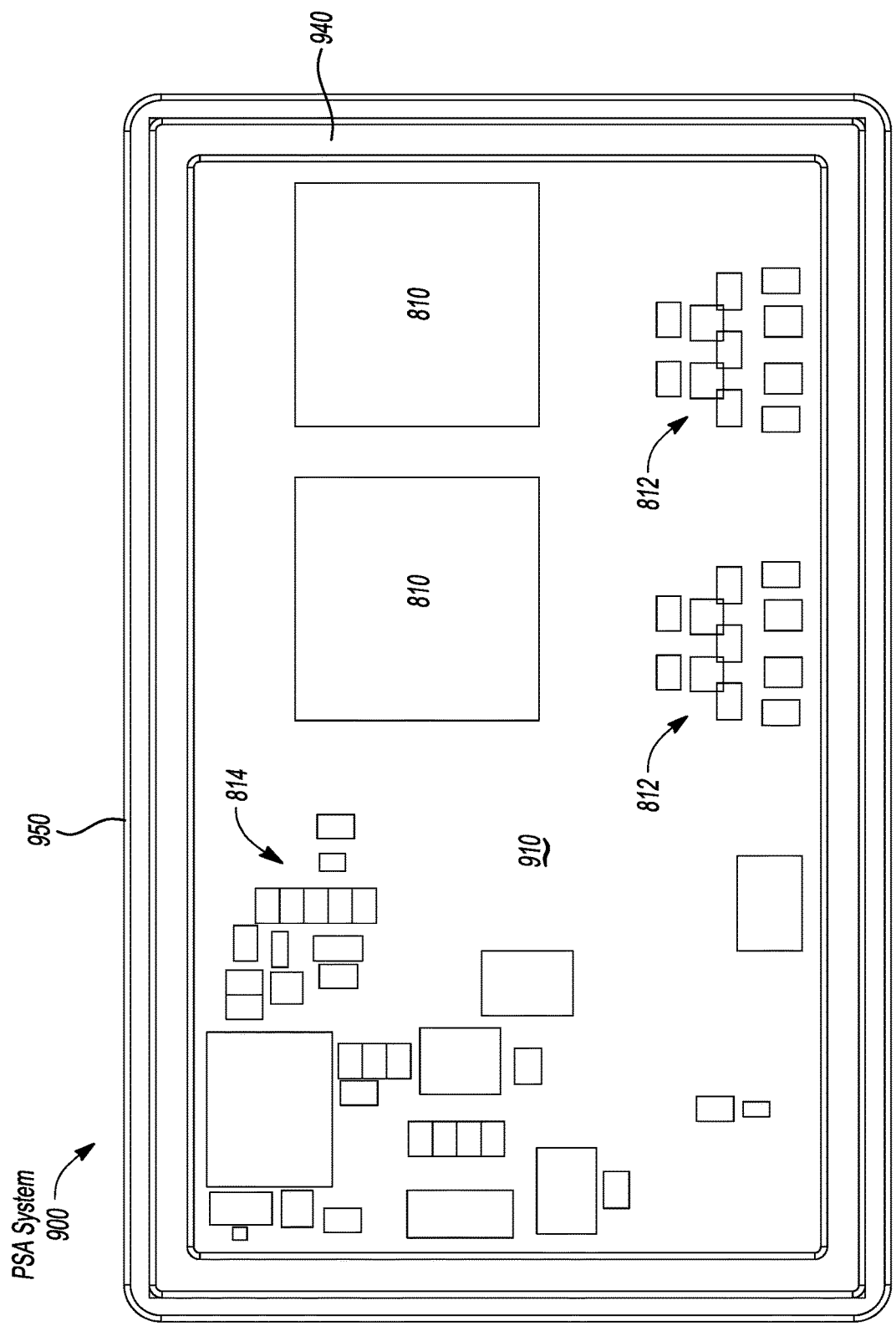
Figure 10:
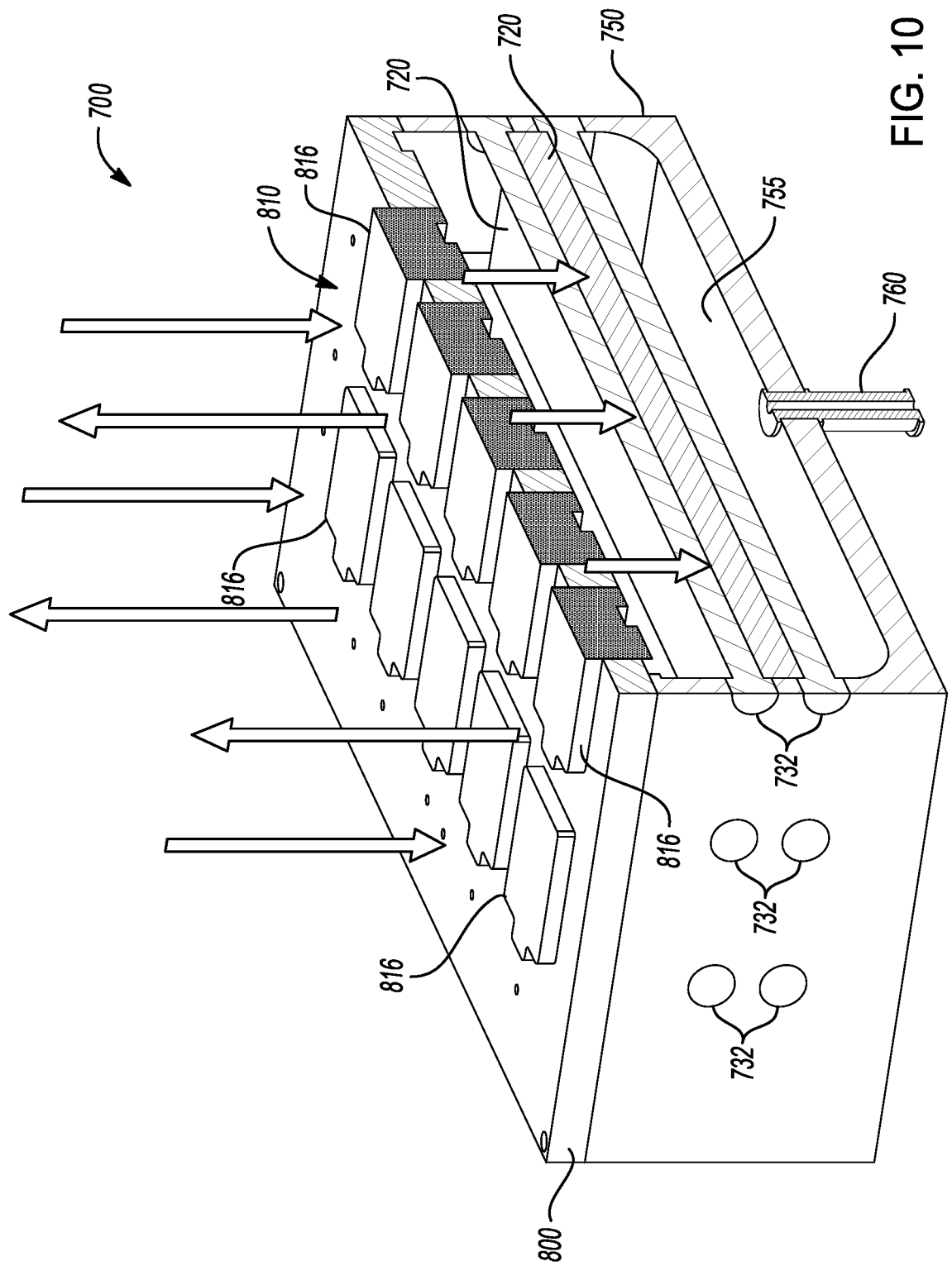
FIG. 10 shows a schematic diagram of an additional exemplary Pressure Swing Adsorption system according to the Pressure Swing Adsorption system of FIGS. 7A-B.
Figure 11:
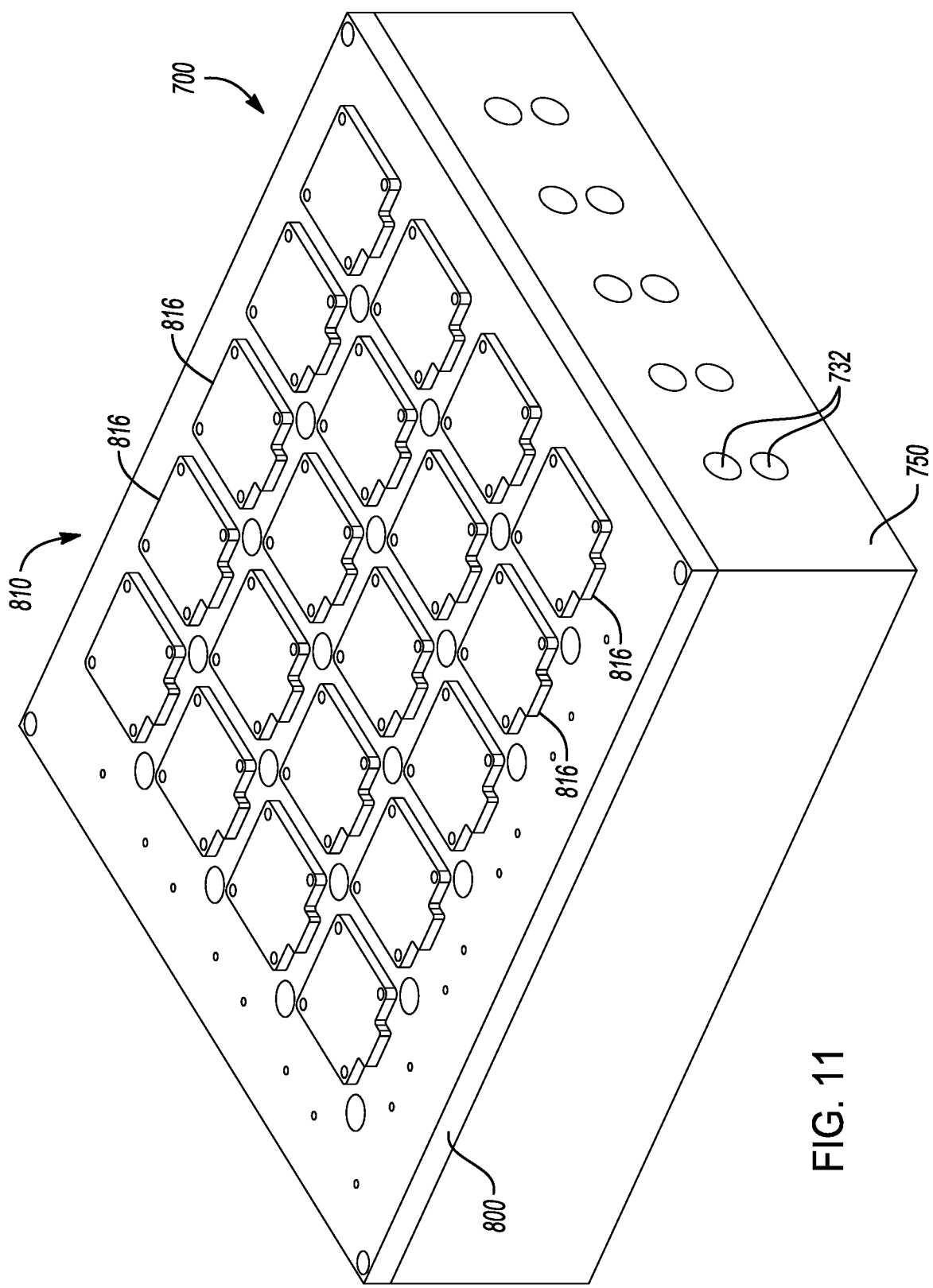
FIG. 11 shows a schematic diagram of an exemplary component of the Pressure Swing Adsorption system according to the Pressure Swing Adsorption system of FIG. 10.
Figure 12:
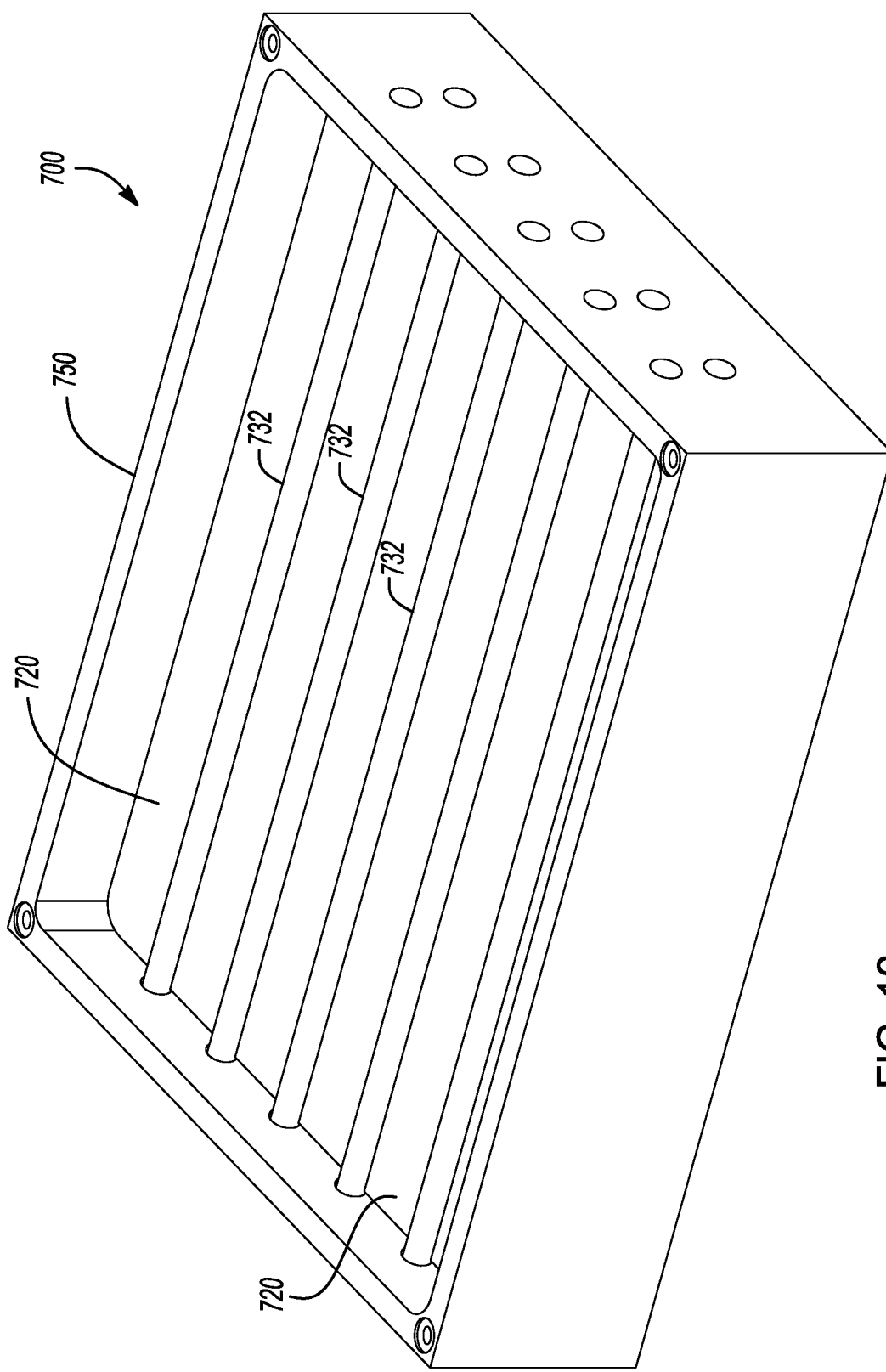
FIG. 12 shows a schematic diagram of an exemplary component of the Pressure Swing Adsorption system according to the Pressure Swing Adsorption system of FIG. 10.

In one example, as shown in FIGS. 8 and 9B, the microblowers 816 and/or the microblower arrays 810 are controlled by MOSFET switches 812 or some other type of microcontroller(s) 814 that can regulate voltage of the MOSFET 812. In this example, one solenoid or piezoelectric valve 760, 960 is required to facilitate depressurization and pressurization of the gas within the PSA case 950, and to output the oxygen enriched gas 216 from the PSA system 700, 900 to the user. By using piezoelectric microblowers 816, the PSA system 900 can transition each individual microblower 816 or microblower array 810 between ON or OFF states extremely rapidly using MOSFET switches 812. For example, a pulse width modulation control can simulate a 26 kHz square wave form of the piezoelectric microblowers 816, precisely controlling the piezoelectric oscillations in order to power the microblowers ON or OFF without any partial oscillations, and as such, producing full depressurization and pressurization cycles even at extremely rapid PSA cycle times.

Further, the opposing set or array 810 of piezoelectric microblowers 816 can be placed on a printed circuit board (PCB) 910 to facilitate the cyclical pressurization and depressurization. With an opposed set of piezoelectric microblowers, it is possible to construct an ultra-rapid vacuum pressure swing adsorption system 10 while reducing the number of valves required, improving separative performance based on the adsorption isotherm.

IX. Oxygen Concentrator Functioning as CPAP or BIPAP Device

In one embodiment, a PSA system 10, such as the PSA system 300 shown in FIG. 3A, can be configured such that a user patient using the PSA system 300 may exhale through an exhalation outlet (not shown) that may function separately or in conjunction with the valve 340, for example in a wye-type configuration, such that carbon dioxide (CO2) rich gas outputted from the user during the user's exhalation phase is not re-inhaled by the user with enriched oxygen gas 216 produced during an adsorption phase 211 for the PSA cycle and outputted to the user during the user's inhalation phase. In some instances, such as for those users with obstructive sleep apnea, it may be advantageous to provide above-atmospheric pressure during the exhalation phase, also known in prior art as positive end expiratory pressure (PEEP). In one embodiment, this positive pressure could be provided by the compressor 310 as shown in FIG. 3A, where valve 340 can be configured as a 3-way valve or a separate valve (not shown) can be added to the PSA system 300, such that compressed air 236 can be routed via the valve 360 configured as a 3-way valve, to the user during the desorption phase 241 of the PSA cycle. During the desorption phase 241 of a PSA cycle, oxygen enriched gas 216 from the oxygen purge tank 330 flows through the adsorption column 320 such that nitrogen is removed (desorbed) from the adsorption column 320 and flushed as gaseous nitrogen to the atmosphere via the nitrogen release valve 370. During the PSA cycle desorption phase 241, valve 340 is closed and valve 370 is open, such that no output gas is delivered to the user during the desorption phase 241. In this embodiment, where the PSA cycle is modified to provide above-atmospheric pressure to the user during the user's exhalation phase, the compressor 310 would be operated continuously or in a manner such that positive end expiratory pressure could be provided to the user. In this instance, the 3-way valve 360 would be opened such that the compressed air 236 generated by the continuously operating compressor 310 is routed to the user output gas outlet after the closed valve 340, and valve 360 would be selectively closed such that the compressed air 236 could not flow through the valve 360 to the adsorption column 320. In this configuration, the desorption of the adsorption column 320 continues in a closed circuit comprising the oxygen purge tank 330, the valve 330 and 370, and the adsorption column 320, while concurrently the pressurized air 236 produced by the compressor is routed through valve 360 to the user output gas outlet to provide pressurized air 236 to the user during the user's exhalation phase, as illustrated by the phase graph 20E shown in FIG. 1I.

Further, in one embodiment, the motor speed of the blower or compressor 310 can be adjusted by the controller 380, using one or more algorithms and/or feedback control such that the pressure and flowrate characteristics of the pressurized air 236 outputted by the compressor 310 to provide PEEP to the user can be altered using data from breathing cycle sensors 16, 18, including, for example, pressure sensors or mass air flowrate sensors. In one embodiment, a compressor 310 with >30 cmH2O pressure, similar to prior art oxygen concentrators, could be utilized for the PSA oxygen generating process, wherein air could be accumulated in an air pressure tank 332 (see FIG. 3H) during the desorption phase 241, and a separate blower (not shown) could be utilized to provide PEEP between 0.1-30 cmH2O pressure to the user during the user's exhalation phase, allowing an oxygen concentrator including a pulsed PSA system 10 to function as a continuous positive airway pressure (CPAP) device or as a bilevel positive airway pressure (BiPAP) device.

Figure 13A:
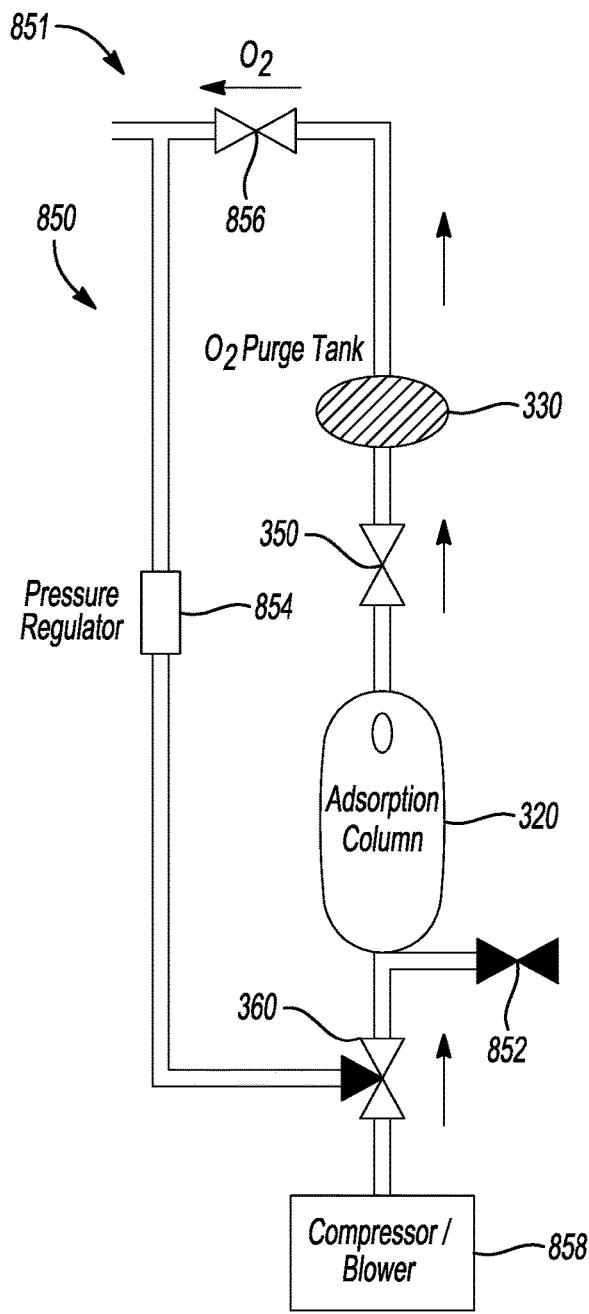
FIGS. 13A-C shows a schematic diagram of an exemplary Pressure Swing Adsorption system according to some embodiments.
Figure 13B:
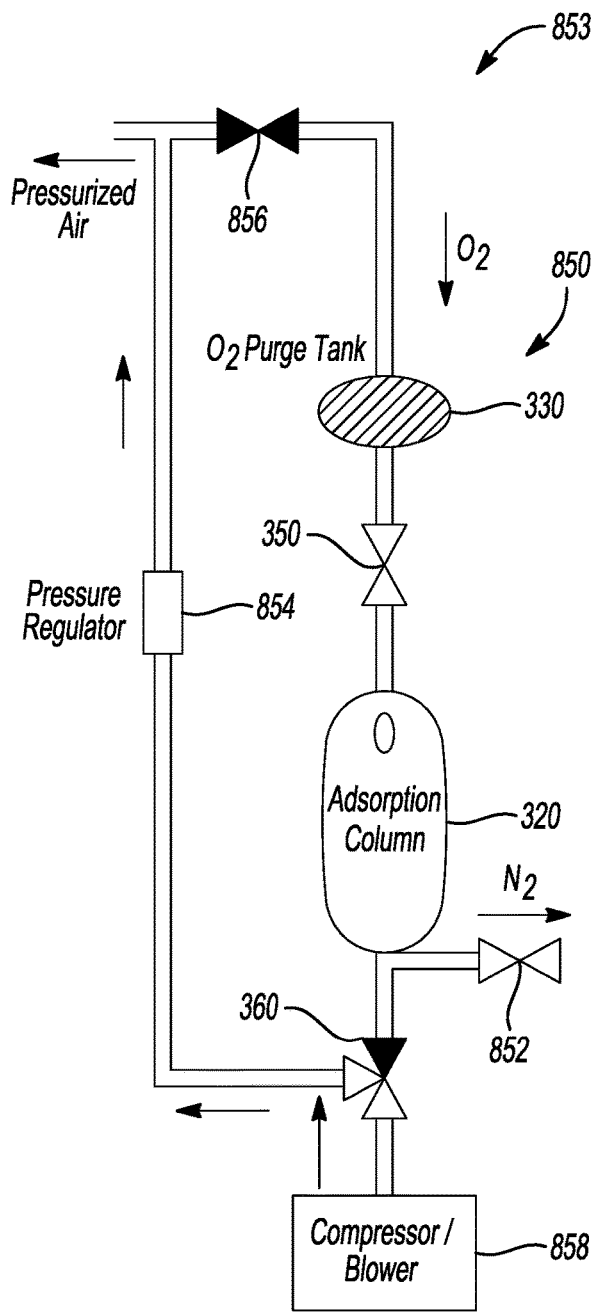

In another example configuration is shown FIGS. 13A-13B, a PSA system 850 operable to function as a CPAP device or as a BiPAP device is illustrated. FIG. 13A illustrates the valve configuration 851 of the PSA system 850 during an adsorption phase 211, where enriched oxygen gas 216 is outputted to the user via valve 858. FIG. 13B illustrates the valve configuration 853 of the PSA system 850 during a desorption phase 241, where pressurized air 236 is outputted to the user via a pressure regulator while concurrently, desorption of the adsorption column 320 is conducted.

Referring to FIG. 13A, during the adsorption phase 211, a first position of valve 360 is closed, and a second position of valve 360 is open, such that compressed air 236 flows from the compressor/blower 858 to the adsorption column 320, where nitrogen is adsorbed from the air and oxygen enriched gas 216 is output via open valve 350, the oxygen purge tank 330 and open valve 856 to a user, in sync with the inhalation phase of the user's breathing cycle 202. Valve 852 is closed during the adsorption phase 211.

During the oxygen purge phase 221 following the adsorption phase 211, the first position of valve 360 is closed, and the second position of valve 360 is open to flow compressed air 236 through the adsorption column 320. Valve 852 is closed. Valve 350 is open and valve 856 is closed, such that enriched oxygen gas 216 accumulates in the O2 purge tank 330, however is not outputted to the user. The first position of valve 360 is opened, such that pressurized air 236 flows to user from the compressor 858. In one example a pressure regulator 854 can be included in the PSA system 850, as shown in FIG. 13A, to regulate the pressure level of the compressed air 236 being outputted from the blower 858 to the user as PEEP. In one example, the controller 380 (not shown) can be configured to actuate the oxygen purge phase 211 at the beginning of the dead space period of the user's inhalation phase. In another example shown in FIG. 15, the oxygen purge phase 221 can be eliminated from the PSA cycle by the use of a vacuum desorption process, such that the PSA cycle transitions directly to the desorption phase 241 from the adsorption phase 211.

During the desorption phase 241, as shown in FIG. 13B, the first position of valve 360 is open such that pressurized air 236 outputted from the compressor/blower 858 flows to the user, via a pressure regulator 854 in the example shown, as PEEP. The desorption phase 241 is synchronized with the user's breath flow phases such that the desorption phase 241 and the flow of PEEP to the user is initiated during a non-productive portion of the user's breathing cycle 202, for example, as shown in FIG. 1I, during the dead space period of the inhalation phase, or during the exhalation phase. Concurrently with flowing pressurized air 236 as PEEP to the user, the desorption phase 241 of the PSA cycle is actuated, where during the desorption phase 241, the second position of valve 360 is closed to prevent compressed air 236 from flowing to the adsorption column 320 from the compressor/blower Position 1 for Valve 260 open, Position 2 for Valve 260 closed. Valve 240 closed. Valve 250 and Valve 270 open. Enriched O2 from O2 purge tank 230 flows back through adsorption column 220. N2 flows out through Valve 270 to atmosphere.

Figure 13C:
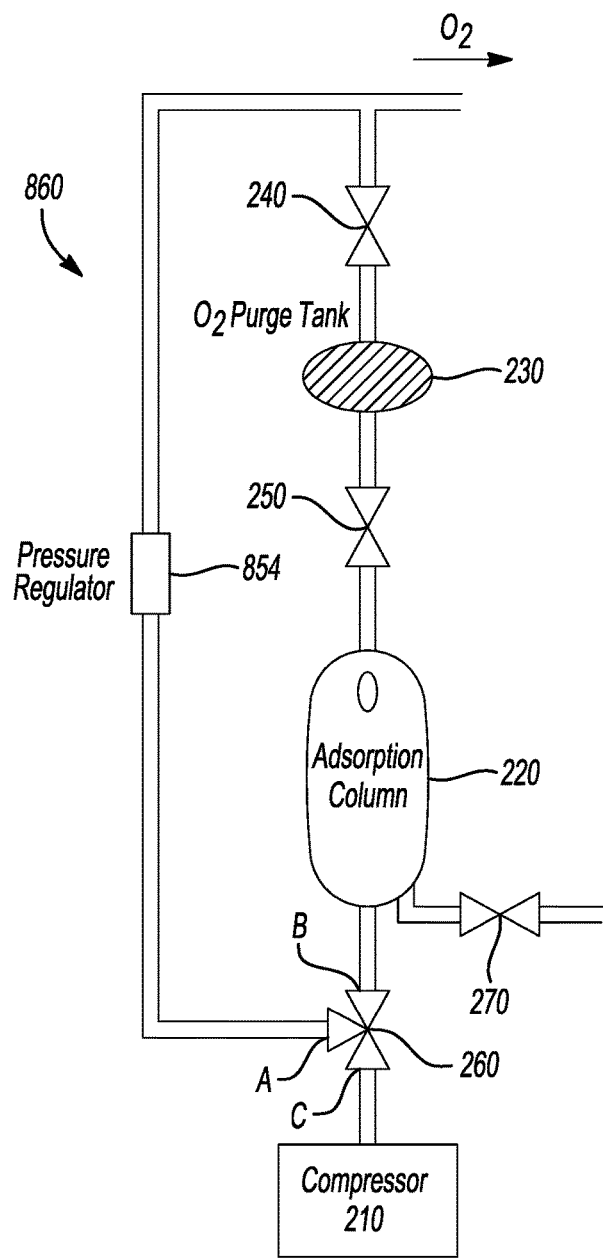

Referring to FIG. 13C, shown is another example configuration of a pulsed PSA (PPSA) system 860 which can be controlled to output pressurized air 236 to a user during the desorption phase 241 of the PSA cycle. In the example shown in FIG. 13C, during the adsorption phase 211, position A for valve 260 is closed and position B for valve 260 is open, such that compressed air 236 flows from the compressor 210 through the adsorption column 220. During the adsorption phase 211, valve 270 closed, valves 250 and 240 are open, such that the enriched oxygen gas 261 generated in the adsorption column 220 by absorption of nitrogen from the incoming air 236 is outputted to the user. In one example, the PSA system 860 includes a controller 380 which synchronizes actuation of the adsorption phase 211 with a production portion of the user's breath flow phases, such that, for example, the adsorption phase 211 is initiated at the beginning of a pre-inhalation period of the user's exhalation phase or at the beginning of a user inhalation phase.

An O2 purge phase 221 of the PSA cycle is actuated, for example, at the beginning of a dead space period of the user's inhalation phase, where during the O2 purge phase 221, position A for valve 260 is closed and position B for valve 260 is opened such that compressed air flows from the compressor 210 through the adsorption column 220. Valves 240 and 270 are closed and valve 250 is open during the O2 purge phase 221, such that enriched oxygen gas 216 accumulates in the O2 purge tank 230, however no enriched oxygen gas 216 is provided to user. Rather, pressurized air 236 flows to the user from the compressor 210. In one example, the pressure of the pressurized air 236 flowing to the user is regulated by a pressure regulator 854, according to the user's requirements. The O2 purge phase 221 can be eliminated from the PSA cycle, as previously described herein, with the use of vacuum assisted desorption.

A desorption phase 241 of the PSA cycle is actuated, for example, at the beginning of the user's exhalation phase, where during the desorption phase 241, position A for valve 260 is open and position B for valve 260 closed, valve 240 is closed, and valves 250 and 270 are open. During the desorption phase 241, enriched oxygen gas 216 from the O2 purge tank 230 flows back through adsorption column 220 and nitrogen is desorbed in the form of nitrogen gas, which is vented from the PSA system 10 through valve 270 to the atmosphere.

Figure 14:
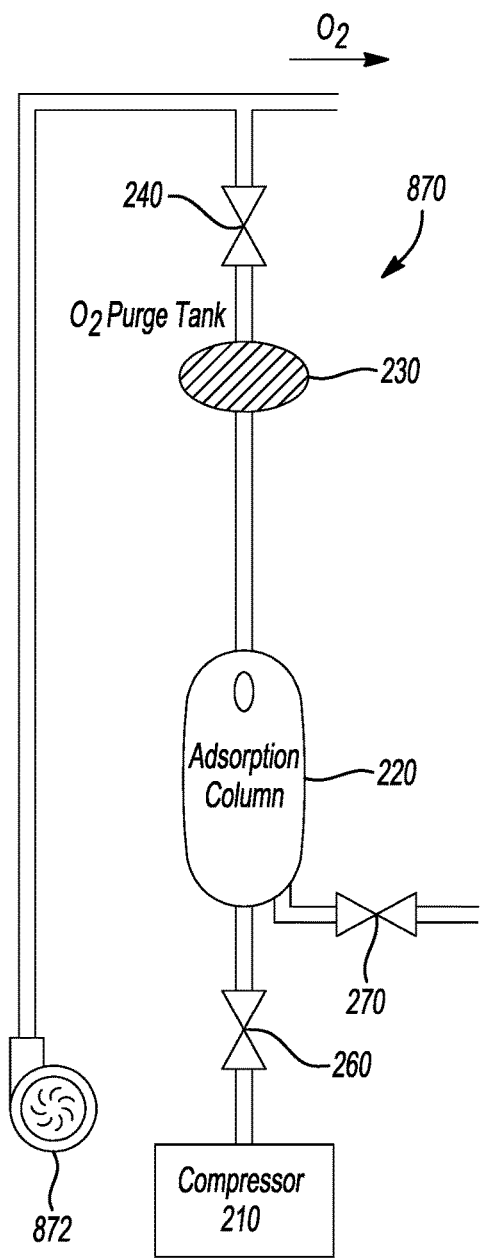
FIG. 14 shows a schematic diagram of an exemplary Pressure Swing Adsorption system according to some embodiments.

In another example configuration illustrated by FIG. 14, a pulsed PSA (PPSA) system 870 including a compressor 210 and a separate blower 872 is shown. In this example, the separate blower is actuated to provide pressurized air 236 to the user during time periods when enriched oxygen gas 216 is not being outputted to the user from the PSA system 870. In an illustrative example, the blower 872 continuously provides pressurized air 236 to the user during the user exhalation phase, and during the O2 purge 221 and desorption 241 phases performed by the PSA system 870. This configuration permits dedicated use of the compressor 210 to support on-demand production of enriched oxygen gas 216 synchronized to the user's breath flow phases, and/or to allow accumulation of compressed air 236 in an air volume tank (not shown) which allows higher flowrates of enriched oxygen gas 216 to be provided to the user during the inhalation phases of user breathing. The blower 872, in the example shown, outputs a lower pressure air flow 236 which can be provided to the user as PEEP during the user exhalation phases.

In the example shown in FIG. 14, the adsorption phase 211 is actuated by opening valve 260 and closing valve 270, and powering on the compressor 210 to flow compressed air through the adsorption column 220. The adsorption phase 211 is synchronized with the user's breathing pattern such that the enriched oxygen gas 216 outputted from the adsorption column 220 flows through open valve 240 to the user during the production portion of the user's breathing cycle, as previously described herein.

In a next step, the blower 872 is actuated concurrent with initiation of the O2 purge phase 221 of the PSA cycle, which could occur, for example, during the anatomical dead space period of the user's inhalation phase or any other phase of the user breathing cycle. During the O2 purge phase 221, the compressor 210 is powered on and flows compressed air 236 through the adsorption column 220. During the O2 purge phase, valve 260 is open and valve 270 and 240 are closed, such that enriched oxygen gas 216 from the adsorption column 220 accumulates in the O2 purge tank 230, while pressurized air from the blower 872 flows to user continuously, such that performance of the PSA cycle and generation of PEEP to the user occur independently of each other in this example embodiment.

In a next step, the desorption phase 241 of the PSA cycle is initiated. During the desorption phase 241, which is synchronized with the user's exhalation phase, the blower 872 continues to independently and continuously output pressurized air 236 to the user during the user's exhalation phase and for the duration of the desorption phase 241. During the desorption phase 241, the compressor 210 can either be powered off to provide an energy savings to the PSA system 870, or air volume tank can be added to the PSA system 870 such that pressurized air outputted from the compressor 210 during the desorption phase can be accumulated for use during a subsequent adsorption phase 211. In this example, with the compressor 210 continuously powered on, valve 260 is closed to prevent the flow of compressor air to the adsorption column 220, allowing desorption of the adsorption column 220 to occur while accumulating pressurized air from the compressor 210 in an air volume tank. Valve 270 is open and valve 240 is closed such that oxygen enriched gas flows from the O2 purge tank 230 back through adsorption column 220 and nitrogen is desorbed from the adsorption bed as nitrogen gas, which flows out through valve 270 to the atmosphere.

Figure 15:
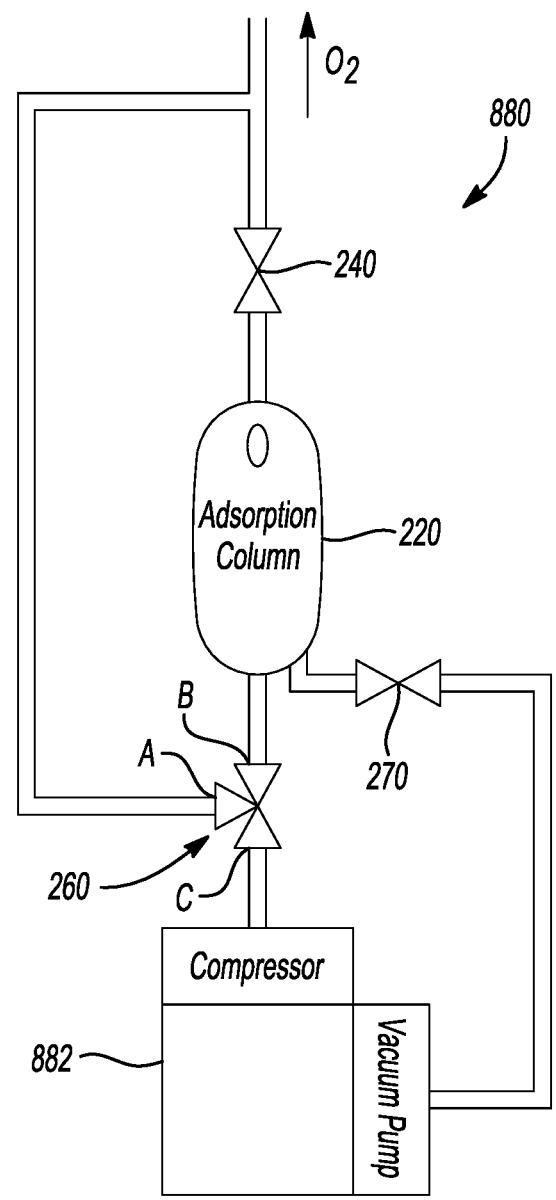
FIG. 15 shows a schematic diagram of an exemplary Vacuum Pressure Swing Adsorption system according to some embodiments.

In another example configuration of a pulsed PSA (PPSA) system 880 shown in FIG. 15, the PPSA system 880 includes a combination compressor and vacuum pump 882, such that an O2 purge tank is not required, and the PSA cycle is performed without an O2 purge phase 221. In one embodiment, the combination compressor and vacuum pump 882 could be enabled either using a dual-head compressor or having separate pressure and vacuum pumps. During the absorption phase 221, the valve 260 is open for position B and valve 270 is closed. Pressurized air 236 flows through the adsorption column 220 to generate enriched oxygen gas 216 which is flowed to user via the open valve 240. Valve 260 in position A is closed, and the vacuum pump portion of pump 882 is powered off.

During the vacuum assisted desorption phase 241, valve 260 is closed for position B and open for position A. Valve 270 is open and valve 240 is closed. Both the compressor and vacuum of pump 882 are powered on, such that nitrogen is desorbed from the adsorption column 220 using vacuum pressurized air from the vacuum portion of pump 882, while concurrently, the compressor function of pump 882 outputs pressurized air 236 to the user via position A of valve 260.

The example shown in FIG. 15 is non-limiting, and variations of this configuration could be used. For example, a two-way valve can be substituted for the three-way valve 260, and a separate blower can be added to deliver pressurized air 236 to the user during the exhalation phase.

X. Additional Configurations

The illustrative configurations of the PSA system 10 described herein are non-limiting examples of PSA system 10, such that other configurations of the PSA system 10 can be included within the scope of the description. For example, an ultra-rapid pressure swing adsorption (URPSA) system using piezoelectric microblowers 816 regulated by MOSFET 812 can be reduced in size even further through the incorporation of microfabrication and microelectromechanical system (MEMS) components into the PSA system 10. As used herein, the term "MEMS" refers to components and/or devices that range in size from 1 micron to 1000 microns (1 mm). By way of illustrative example, MEMS components and/or devices which can be incorporated into the PSA system 10 to shrink the packaging size of the oxygen concentrator including the PSA system 10 can include microfabricated wafer thin zeolite adsorbents, micro-scale MEMS air blowers, and ultra-fast actuating MEMS microvalves. In another example, NEMS devices can be utilized to create microchip and transistor scale pressure swing adsorption systems and can be fabricated using semiconductor manufacturing techniques found in optoelectronics and photolithography. As used herein, the term "NEMS" refers to components and/or devices that are less than 1 micron in size.

In one example of the invention described above, a microphone and amplifier can be incorporated into the PSA system 10 and/or into the oxygen delivery device 342, instead of or in addition to the pressure sensor 16 of the PSA system 10. In this configuration, a respiration sensing microphone and/or an amplifier detect sound from a user when the user begins respiration, e.g., begins an inhalation phase. The controller 380 receives an amplified signal from the microphone indicating the onset of the user's inhalation phase, and activates the adsorption phase 211 of the PSA cycle. The dosage of the enriched oxygen gas 216 provided to the user, in this example, could be in proportion to the signal strength of the respiration sensor. Like that of the pressure sensor, the controller 380 of the PSA system 10 can also configure settings such that a threshold signal must be detected for the adsorption and/or desorption phases 211, 241 to begin and/or end. The location of the microphone and amplifier in this example can be non-invasive to the user, located at the portion of the PSA system 10 where the user physically engages the PSA system, via a nasal cannula 12 for example.

In one example of the pulsed pressure swing adsorption (PPSA) system, a multi-bed pressure swing adsorption system 10 can also be utilized, where the adsorption phase 211 of each adsorption bed of the multi-bed system is synchronized with different flow phases of the user's breath, and/or with different periods within the flow phases of the user's breath. For example, asynchronous cycle times can be achieved utilizing the two adsorbent beds with a similar control system described in previous configurations herein.

In one example of an ultra-rapid pressure swing adsorption (URPSA) system, a macro scale variant can be created such that low pressure change, high volumetric flow blowers, ultra-rapid cycle times, and low length to diameter (L:D) ratio adsorbent materials are utilized. Further, the flow blowers do not need to be microblowers 816. Instead, the flow blowers can include larger macroscale fan blowers or centrifugal pumps. Other air compressor types or blowers can also be utilized including but not limited to thermoelectric blowers, Tesla turbine type air compressors, bellows air compressors, scroll type air compressors, wobble type compressors, and reciprocating compressors.

In other embodiments, particularly in ultra-rapid pressure swing adsorption (USPSA) systems 10, passive check valves with low cracking pressures can be utilized instead of actively controlled solenoid valves or proportional control valves. Further, Tesla valvular conduits could also be utilized to simultaneously allow flow in one direction with no cracking pressure constraints and also allow a small percentage of oxygen to flow backwards during the purge or vacuum desorption phases of the PSA cycle.

In one embodiment, the pulsed pressure swing adsorption system could function as a mechanical ventilator wherein a ventilator circuit can be added to assist a user who cannot spontaneously breathe and may also require supplemental oxygen.

In some embodiments of the invention, the PSA cycle times of the PSA cycles and/or PSA cycle phases may be fixed, which may be advantageous due to programming simplicity, especially in cases where the cycle times are rapid or ultra-rapid. Advantageously, this can provide continuous flow output oxygen conservation described herein as being based not on variable cycle times, but rather based on proportional valve control and/or the sensor control system described herein.

In this specification, reference is made in detail to specific embodiments of the invention. Some of the embodiments or their aspects are illustrated in the drawings. For clarity in explanation, the invention has been described with reference to specific embodiments, however it should be understood that the invention is not limited to the described embodiments. The invention covers alternatives, modifications, and equivalents as may be included within its scope as defined by any patent claims. The preceding embodiments of the invention are set forth without any loss of generality to, and without imposing limitations on, the claimed invention. In the preceding description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. The present invention may be practiced with different combinations of the features in each described configuration.

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

The invention claimed is:

1. An oxygen concentrator system comprising:
a pressure swing adsorption (PSA) system including:
a gas outlet airline configured to flow oxygen enriched gas to a user of the oxygen concentrator;
wherein the PSA system is configured to execute a PSA cycle to produce the oxygen enriched gas;
a cannula configured to receive breathing gas from the user;
a sensor in communication with the cannula and the PSA system; wherein the sensor is configured to sense a breathing cycle of the user;
wherein:
the breathing cycle includes an inhalation phase and an exhalation phase;
the exhalation phase includes a non-useful period succeeded by a pre-inhalation period;
wherein each respective breath is immediately preceded in the breathing cycle by a preceding breath and is immediately succeeded in the breathing cycle by a succeeding breath;
wherein the cannula is configured such that carbon dioxide ($CO_2$) rich gas output from the user during the exhalation phase of the preceding breath is not re-inhaled by the user during the inhalation phase of the succeeding breath; and
wherein the PSA system is configured to actuate a flow of the oxygen enriched gas via the gas outlet airline at the beginning of the pre-inhalation period of the exhalation phase.

2. The oxygen concentrator system of claim 1, wherein:
the PSA cycle includes an adsorption phase and a desorption phase; and
the PSA system is configured to synchronize execution of the PSA cycle with the breathing cycle such that the adsorption phase is actuated at the beginning of the pre-inhalation period.

3. The oxygen concentrator system of claim 1, wherein the gas outlet airline is a unidirectional airline configured to flow the oxygen enriched gas to the user.

4. The oxygen concentrator system of claim 1, wherein the cannula is a bidirectional airline.

5. The oxygen concentrator system of claim 1, wherein the sensor is located in the cannula.

6. The oxygen concentrator system of claim 1, wherein the beginning of the pre-inhalation period is defined by at least one of an actual beginning or a predicted beginning of the pre-inhalation period.

7. The oxygen concentrator system of claim 1, further comprising:
a controller in communication with the sensor, the controller is configured to:
receive breath parameter data from the sensor; and
determine, using the breath parameter data, an actual beginning of the pre-inhalation period; and
wherein the PSA system is configured to actuate the flow of the oxygen enriched gas via the gas outlet airline at the actual beginning of the pre-inhalation period.

8. The oxygen concentrator system of claim 1, further comprising:
a controller in communication with the sensor, the controller is configured to:
receive breath parameter data from the sensor; and
determine, using the breath parameter data, a predicted beginning of the pre-inhalation period;
wherein the PSA system is configured to actuate the flow of the oxygen enriched gas via the gas outlet airline at the predicted beginning of the pre-inhalation period.

9. The oxygen concentrator system of claim 1, wherein the PSA system is configured to output a positive end expiratory pressure (PEEP) to the user during the exhalation phase of the user.

10. The oxygen concentrator system of claim 9, wherein the PSA system includes a plurality of microblowers actuable to output pressurized air via the gas outlet line.

11. An oxygen concentrator system comprising:
a pressure swing adsorption (PSA) system including:
a gas outlet configured to selectively flow oxygen enriched gas or pressurized air to a user of the oxygen concentrator;
wherein the PSA system is configured to execute a PSA cycle to produce the oxygen enriched gas;
a sensor in communication with the gas outlet and the PSA system;

wherein the sensor is configured to sense a breathing cycle of the user;

wherein the breathing cycle includes an inhalation phase and an exhalation phase;

wherein each respective breath is immediately preceded in the breathing cycle by a preceding breath and is immediately succeeded in the breathing cycle by a succeeding breath;

wherein:
- the inhalation phase includes a useful period and a dead space period;
- the dead space period occurs between the useful period and the exhalation phase;
- wherein the PSA system is further configured to actuate a flow of the pressurized air via the gas outlet at the beginning of the dead space period of the inhalation phase; and a cannula configured such that carbon dioxide (CO2) rich gas output from the user during the exhalation phase of the preceding breath is not re-inhaled by the user during the inhalation phase of the succeeding breath.

12. The oxygen concentrator system of claim 11, wherein the PSA system is configured to flow oxygen enriched gas via the gas outlet at an actual beginning or at a predicted beginning of the inhalation phase of the user.

13. The oxygen concentrator system of claim 11, wherein the at least one breathing parameter is the actual beginning or the predicted beginning of the inhalation phase of the user.

14. The oxygen concentrator system of claim 11, wherein:
the PSA cycle includes an adsorption phase and a desorption phase; and
the controller is configured to synchronize execution of the PSA cycle with the at least one breathing parameter.

15. The oxygen concentrator system of claim 12, further comprising:
a controller in communication with the sensor and the PSA system;
the controller configured to:
receive breathing parameter data from the sensor; and
determine at least one breathing parameter of the use in real time.

* * * * *